US008591914B2

(12) United States Patent
Yang et al.

(10) Patent No.: US 8,591,914 B2
(45) Date of Patent: Nov. 26, 2013

(54) INFLUENZA HEMAGGLUTININ AND NEURAMINIDASE VARIANTS

(75) Inventors: Chin-Fen Yang, San Jose, CA (US); George Kemble, Saratoga, CA (US)

(73) Assignee: Medimmune, LLC, Gaithersburg, MD (US)

(*) Notice: Subject to any disclaimer, the term of this patent is extended or adjusted under 35 U.S.C. 154(b) by 0 days.

(21) Appl. No.: 13/003,559

(22) PCT Filed: Jul. 9, 2009

(86) PCT No.: PCT/US2009/050070
§ 371 (c)(1),
(2), (4) Date: Apr. 29, 2011

(87) PCT Pub. No.: WO2010/006144
PCT Pub. Date: Jan. 14, 2010

(65) Prior Publication Data
US 2011/0212117 A1    Sep. 1, 2011

Related U.S. Application Data

(60) Provisional application No. 61/079,894, filed on Jul. 11, 2008, provisional application No. 61/110,702, filed on Nov. 3, 2008, provisional application No. 61/178,592, filed on May 15, 2009.

(51) Int. Cl.
*A61K 39/00* (2006.01)
*A61K 35/00* (2006.01)

(52) U.S. Cl.
USPC .................................. 424/211.1; 424/185.1

(58) Field of Classification Search
None
See application file for complete search history.

(56) References Cited

U.S. PATENT DOCUMENTS

| | | | |
|---|---|---|---|
| 3,992,522 A | 11/1976 | Chanock et al. |
| 4,071,618 A | 1/1978 | Konobe et al. |
| 4,634,666 A | 1/1987 | Engelmann et al. |
| 4,659,569 A | 4/1987 | Mitsuhashi et al. |
| 5,166,057 A | 11/1992 | Palese et al. |
| 5,690,937 A | 11/1997 | Parkin |
| 5,716,821 A | 2/1998 | Wertz et al. |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,922,326 A | 7/1999 | Murphy |
| 6,001,634 A | 12/1999 | Palese et al. |
| 6,033,886 A | 3/2000 | Conzelmann |
| 6,090,391 A | 7/2000 | Parkin |
| 6,146,642 A | 11/2000 | Garcia-Sastre et al. |
| 6,146,873 A | 11/2000 | Kistner et al. |
| 6,168,943 B1 | 1/2001 | Rose |
| 6,951,754 B2 | 10/2005 | Hoffmann |
| 7,037,707 B2 | 5/2006 | Webster et al. |
| 7,459,162 B2 | 12/2008 | Yang |
| 7,566,458 B2 | 7/2009 | Yang |
| 8,048,430 B2 | 11/2011 | Yang |
| 8,333,975 B2 | 12/2012 | Yang |
| 2002/0119445 A1 | 8/2002 | Parkin et al. |
| 2002/0164770 A1 | 11/2002 | Hoffmann |
| 2003/0035814 A1 | 2/2003 | Kawaoka |
| 2003/0147916 A1 | 8/2003 | Ferko |
| 2004/0029251 A1 | 2/2004 | Hoffman et al. |
| 2004/0071734 A1 | 4/2004 | Garcon et al. |
| 2004/0137013 A1 | 7/2004 | Katinger |
| 2005/0042229 A1 | 2/2005 | Yang |
| 2005/0266026 A1 | 12/2005 | Hoffmann |
| 2006/0188977 A1 | 8/2006 | Schwartz et al. |
| 2006/0252132 A1 | 11/2006 | Yang et al. |
| 2007/0253982 A1 | 11/2007 | Song et al. |
| 2009/0004222 A1 | 1/2009 | O'Hagan |
| 2009/0017052 A1* | 1/2009 | Bogoch et al. ............ 424/185.1 |
| 2009/0175898 A1 | 7/2009 | Yang |
| 2009/0175908 A1 | 7/2009 | Yang |
| 2010/0239610 A1* | 9/2010 | D'Aoust et al. ........... 424/210.1 |
| 2011/0002960 A1 | 1/2011 | Yang |
| 2011/0070263 A1 | 3/2011 | Yang |
| 2011/0212117 A1 | 9/2011 | Yang |
| 2012/0135023 A1 | 5/2012 | Yang |
| 2013/0156810 A1 | 6/2013 | Yang et al. |

FOREIGN PATENT DOCUMENTS

| | | |
|---|---|---|
| CN | 1536077 | 10/2004 |
| EP | 0702085 | 3/1996 |
| EP | 0863202 | 9/1998 |
| EP | 0864645 | 9/1998 |
| EP | 0780475 | 6/1999 |
| EP | 1826269 | 8/2007 |
| WO | WO 91/03552 | 3/1991 |
| WO | WO 93/21306 | 10/1993 |
| WO | WO 96/10632 | 4/1996 |
| WO | WO 96/34625 | 11/1996 |
| WO | WO 96/37624 | 11/1996 |

(Continued)

OTHER PUBLICATIONS

Alignment sequence between SEQ 10 No. 53 and 8 of U.S. Appl. No. 10/870,690 and U.S. Appl. No. 60/479,078, respectively—Appendix A (Office Action dated: Mar. 18, 2008 in U.S. Appl. No. 10/870,690).
Anwar et al., "In silico analysis of genes nucleoprotein, neuraminidase and hemagglutinin: A comparative study on different strains of influenza A (Bird Flu) virus sub-type H5N1," in Silico Biology 6, 0015 (2006) 161-168.
Banerjee and Barik, 1992, "Gene expression of vesicular stomatitis virus genome RNA", Virology. 188(2):417-28.
Baron and Barrett, 1997, "Rescue of Rinderpest Virus from Cloned cDNA", J. Virol. 71:1265-1271.
Basler et al., Mutation of Neuraminidase Cysteine Residues Yields Temperature-Sensitive Influenza Viruses, Journal of Virology, Oct. 1999, vol. 73, No. 10, p. 8095-8103.
Beare et al., 1975, "Trials in Man with Live Recombinants Made from A/NPR/8/34 (HO N1) and Wild H3 N2 Influenza Viruses", Lancet 2(7938):729-732.

(Continued)

*Primary Examiner* — Bao Li
(74) *Attorney, Agent, or Firm* — Grant Anderson LLP

(57) ABSTRACT

Polypeptides, polynucleotides, methods, compositions, and vaccines comprising influenza hemagglutinin and neuraminidase variants are provided.

22 Claims, 15 Drawing Sheets

(56) References Cited

FOREIGN PATENT DOCUMENTS

| WO | WO 97/06270 | 2/1997 |
|---|---|---|
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/53786 | 9/2000 |
| WO | WO 00/60050 | 10/2000 |
| WO | WO 2005/018539 | 3/2005 |
| WO | WO 2005/116260 | 12/2005 |
| WO | WO 2006/098901 | 9/2006 |
| WO | WO2006098901 A2 * | 9/2006 |
| WO | WO 2010/006144 | 1/2010 |

OTHER PUBLICATIONS

Belshe, 1995 "A Review of Attenuation of Influenza Viruses by Genetic manipulation," American Journal of Respiratory and Critical Care Medicine 152[4 Pt 2], 572-575. 1995.
Belshe, et al., "The Efficacy of live attenuated, cold-adapted, trivalent intranasal influenza virus vaccine in children," (1998) A128N Eng J Med 338:1405-1412.
Bender et al., 1999, "Characterization of the surface proteins of influenza A (H5NI) yiruses . . . ", Virology 254(1):115-23.
Bergmann, el al., "The relative amount of an influenza A virus segment present in the viral particle is not affected by a reduction in replication of that segment,". Journal of General Virology, 1995,76:3211-3215.
Boyce et al., 2001, "Safety and immunogenicity of adjuvanted and unadjuvanled subunit influenza vaccines administered Intranasally to healthy adults", Vaccine 19:217-226.
Boyer et al., 1994, "Infectious transcripts and cDNA clones of RNA viruses", Virology. 198(2):415-26.
Brandt et al., 2001, "Molecular Determinants of Virulence, Cell Tropism. and Pathogenic Phenotype of Infectious Bursal Disease Virus". Journal of Virology 75(24):11974-11982.
Brigden and Elliott. 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Respiratory Syncytial Virus (BRSV) from cDNA: BRSV NS2 is Not Essential for Virus Replication in Tissue Culture. and the Human RSV Leader Region Acts as a Functional BRSV Genome Promoter". J. Virol. 73:251-259.
Bukreyev et al., 1996, "Recovery of infectious respiratory syncytial virus expressing an additional, foreign gene", J Virol. 70(10):6634-6641.
Castrucci et al., 1995, "Reverse genetics system for generation of an influenza A virus mutant containing a deletion of the carboxyl-terminal residue of M2 protein", J Virol. 69(5):2725-2728.
Caton et al., Dec. 1982, "The antigenic structure of the influenza virus AIPR/8/34 hemagglutinin (HIsubtype)", Cell, 31(2 Pt 1):417-27.
Chen et al., "Generation and evaluation of a high-growth reassortant H9N2 influenza A virus as a pandemic vaccine candidate," Vaccine 21 (2003) pp. 1983-1988.
Chen et al., 1999, "Influenza A virus NS1 protein targets poly (A)-binding protein II of the cellular 3'-end processing machinery", EMBO 18: 2273-2283.
Clarke et al., 2000, "Rescue of mumps virus from cDNAJ", J Virol. 74(10):4831-8.
Clements et al., Evaluation of the infectivity and Efficacy of Live Cold-Adapted Influenza B/Ann Arbor/1/86 Reassortant Virus Vaccine in Adult Volunteers, 1990, Journal of Infectious diseases, vol. 161, No. 5, pp. 869-877.
Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663 9657.

Collins et al., 1995, "Production of infectious human respiratory syncytial virus from cloned cDNA confirms an essential role . . . " PNAS 92: 11563-7.
Collins et al., 1996, "Parainfluenza Viruses", Fields Virology, Lippincott-Raven Publishers, Phila., Chapter 41, pp. 1205-1241.
Conzelmann et al., 1994, "Rescue of synthetic genomic RNA analogs of rabies virus by plasmid-encoded proteins", J Virol. 68(2):713-9.
Conzelmann et al., 1996, "Genetic engineering of animal RNA viruses", Trends Microbiol. 4(10):386-93.
Conzelmann et al., 1996, "Genetic manipulation of non-segmented negative-strand RNA viruses", J Gen Virol. 77 (Pt 3):381-389.
Conzelmann et al., 1998, "Nonsegmented negative-strand RNA viruses: genetics and manipulation of viral genomes", Annu Rev Genet. 32:123-62.
Cox. NJ et al., "Identification of sequence changes in the cold-adapted, live attenuated influenza vaccine strain . . . ". Virology. Dec. 1988; 167(2)554-567.
Database Caplus on NCBI, Accession No. AY553802, Influenza A Virus (A/little grebe/Thailand/Phichit-01/2004(H5N1) hemasslutinin {HA) gene, partial cds. May 21, 2004.
Database Geneseq [Online] Jun. 2, 2005, "Influenza B virus DNA sequence, SEQ ID 4." XP002544304 retrieved from EBI accession No. GSN:ADY93069 Database accession No. ADY93069.
Database UniProt [Online] Nov. 1, 1999, "SubName: Full=Prehemagglutinin;" XP002544292 retrieved from EBI accession No. UNIPROT:Q9WPM8 Database accession No. Q9WPM8.
Database UniProt [Online] Dec. 7, 2004, "SubName: Full=Prehemagglutinin;" XP002544291 retrieved from EBI accession No. UNIPROT:Q5V9D2 Database accession No. Q5V9D2.
Database USPTO Proteins [Online] Sep. 29, 1999, "Sequence 19 from patent US 5858368." XP002544293 retrieved from EBI accession No. USPOP:AAE01218 Database accession No. AAE01218.
Database EMBL [Online] E.B.I. Hinxton U.K.; May 15, 2008, Garten R et al: "Influenza A virus (A/Uruguay/716/2007(H3N2)) segment 4 hemagglutinin (HA) gene, complete cds.", XP002665732, A198Database accession No. EU716426.
Database EMBL [Online] E.B.I. Hinxton U.K.; May 15, 2008, Garten R et al: "Influenza A virus (A/Uruguay/716/2007(H3N2)) segment 6 neuraminidase (NA) gene, complete cds.", XP002665734, Database accession No. EU716427.
Database EMBL [Online] E.B.I. Hinxton U.K.; Jul. 1, 2008, Garten R et al: "Neuraminidase; Influenza A virus (A/Uruguay/716/2007(H3N2).", XP002665733, Database accession No. B2ZV33.
Database UNIPROTKB E.B.I. Hinxton U.K.; Jul. 1, 2008, Garten R et al: "Hemagglutinin; Influenza A virus (A/Uruguay/716/2007(H3N2)).", XP002665731, Database accession No. B2ZV32.
Daum et al., Genetic and Antigenic Analysis of the First AINew Caledonia/20/99-like H1 N1 Influenza Isolates Reported in the Americas, 2002, Emerging Infectious Diseases, vol. 8, No. 4, pp. 408-412.
Daum et al., Influenza A (H3N2) Outbreak, Nepal, 2005, Emerging Infectious Diseases, vol. 11, No. 8, pp. 1186-1191.
De and Banerjee, 1985, "Requirements and Functions of Vesicular Stomatitis Virus Land NS Proteins in the Transcription Process in vitro", Biochem. Biophys. Res. Commun. 126:40-49.
De and Banerjee, 1993, "Rescue of synthetic analogs of genome RNA of human parainfluenza virus type 3", Virology, 96(1 ):344-8.
De and Banerjee, 1994, "Reverse genetics of negative strand RNA viruses", Indian J Biochem Biophys. 31(5):367-76.
De et al., "Complete sequence ofa cDNA clone of the hemagglutinin gene of influenza A/Chicken/Scotland/59 (H5NI) virus: comparison with contemporary North American and European strains," Nucleic Acids Research, 1988. vol. 16, No. 9, pp. 4181-4182.
De et al., "Protection against virulent H5 avian influenza virus infection in chickens by an inactivated vaccine produced with recombinant vaccine virus", Jun. 1988 Vaccine vol. 6, pp. 257-261.
De la Luna et al., 1993. "Influenza virus naked RNA can be expressed upon transfection into cells co-expressing the three subunits of the polymerase and the nucleoprotein from simian virus 40 recombinant viruses", J Gen Virol. 74 (Pt 3):535-9.
De La Luna et al., 1995, "Influenza virus NS1 Protein Enhances the Rate of Translation Initiation of Viral mRNAs", J. of Virol. 69: 2427-2433.

(56) References Cited

OTHER PUBLICATIONS di Bernardi di Valserra et al., An Open Label Comparison of the Immunogenicity and Tolerability if Intranasal and intramuscular Formulations of Virosomal Influenza Vaccine in Healthy Adults, 2002, Clinical Therapeutics, vol. 24, pp. 100-111.
Dimock et al., 1993, Rescue of synthetic analogs of genomic RNA and replicative-intermediate RNA of human parainfluenza virus type 3 . . . J Virol. 67(5):2772-8.
Dreher and Hall, 1988, "Mutational Analysis of the Sequence and Structural Requirements in Brome Mosaic Virus RNA for Minus Strand Promoter Activity", J. Mol. Biol. 201:31-40.
Dreher et al., 1984, "Mutant Viral RNAs Synthesized in vitro Show Altered Aminoacylation and Replicase Template Activities", Nature 311:171-175.
Dunn et al., 1995, "Transcription of a recombinant bunyavirus RNA template by transiently expressed bunyavirus proteins", Virology, 211 (1): 133-43.
Durbin et al., 1997, "Recovery of infectious Human Parainfluenza Virus Type 3 from cDNA", Virol. 235:323-332.
Edwards et al.. 1994. "A randomized controlled trial of cold adapted and inactivated vaccines for the prevention of influenza A disease", J Infect Dis 169:68-76.
Egorov et al., Transfectant Influenza A Viruses with Long Deletions in the NS1 Protein Grow Efficiently in Vero Cells, Journal of Virology, Aug. 1998, vol. 72, No. 8, p. 6437-6441.
Elliot et al., 1997, Abstract # 96 10.sup.th International conference on Negative Strand Viruses.
Elliott et al., 1991, "Some highlights of virus research in 1990", J Gen Virol.72 (Pt 8):1761-79. Review. No abstract available.
Ellis and Zambon, Molecular analysis of an outbreak of influenza in the United Kingdom, 1997, European Journal of Epidemiology, vol. 13, pp. 369-372.
Emerson and Yu, 1975, "Both NS and L Proteins are Required for in vitro RNA SynthesiS by Vosicular Stomatitis Virus", J. Virol. 15:1348-1356.
Enami and Palese, 1991, "High-Efficiency Formation of Influenza Virus Transfectants", J. Virol. 65:2711-2713.
Enami et al., 1991, "An influenza virus containing nine different RNA segments", Virology. 185(1):291-8.
Enami et aL, 1990, "Introduction of Site SpeCific Mutations into the Genome of Influenza Virus", Proc Natl Acad Sci USA 87: 3802-3805.
Enami et al., "Characterization of Influenza Virus NS1 Protein by Using a Novel Helper-Virus-Free Reverse Genetic System" Journal of Virology, 2000, 74(12):5556-5561.
Fahey and Schooley, 1992, "Status of Immune-Based Therapies in HIV Infection and AIDS", Clin. Exp. Immunol. 88:1-5.
Flandorfer et al., 2003, •Chimeric Influenza A Viruses with a Functional Influenza B Virus Neuraminidase or Hemagglutinin, J. of Virology—77(17):9116-9123.
Flick. et al., "Promoter elements in the influenza vRNA terminal structure," RNA, 1996: 2(10):1046-1057.
Fodor et al., "Rescue of Influenza A Virus from Recombinant DNA". J. of Virology, Am. Society for Microbiology. Nov. 1999, vol. 73, No. 11, pp. 9679-9682.
Fortes et al., 1994, "Influenza virus NS 1 protein inhibits pre-mRNA splicing and blocks mRNA nucleocytoplasmic transport", EMBO 13: 704-712.
Furminger, "Vaccine Production," Textbook of Influenza, pp. 324-332 (1996).
Garcia-Sastre A, Palese p, 1993. "Genetic manipulation of negative-strand RNA virus genomes", Annu Rev Microbiol. :47:765-90.
Garcin et al., 1995, A highly recombinogenic system for the recovery of infectious sendai paramyxovirus from cDNA: generation of a novel copy-back nondefeclive interfering virus•, EMBO J. 14: 6087-6094.
GenBank Accession No. AAB63711, Nov. 17, 1999.
GenBank Accession No. AAK70453, Mar. 11, 2003.
GenBank Accession No. AAK70456, Mar. 11, 2003.
GenBank Accession No. AAK70457, Mar. 11, 2003.
GenBank Accession No. AAP34324, Sep. 3, 2003.
GenBank Accession No. AAT12657 Mar. 26, 2005.
GenBank Accession No. AAT12674 Mar. 26, 2005.
GenBank Accession No. AJ344014, Published Apr. 15, 2005.
GenBank Accession No. CAC86622, Apr. 15, 2005.
GenBank Accession No. AAX11495 Oct. 12, 2006.
GeneBank Accession No. CAH04474, Jul. 11, 2005.
GeneBank Accession No. CY000025, Feb. 20, 2005.
GeneBank accession No. CY027571.1, Nov. 27, 2007.
Ghendon, "Cold-Adapted, Live Influenza Vaccines Developed in Russia," Textbook of Influenza, Chapter 29, pp. 391-399 (1998).
Goto et al., 1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-272.
Govorkova, et al., "African Green Monkey Kidney (Vero) Cells Provide an Alternative Host Cell System for Influenza A and B Viruses". Journal of Virology. American Society for Microbiology. Aug. 1996. vol. 70. No. 8, pp. 5519-5524.
Grosfeld et al., 1995, RNA replication by respiratory syncytial virus (RSV) is directed by the N. P. and L proteins: transcription also occurs under these conditions but requires RSV superinfection for efficient synthesis of full-length mRNA. J Virol. 69(9):5677-86.
Guan, Vi, et al., "Molecular Characterization of H9N2 Influenza Viruses: Were They the Donors of the "Internal" Genes of H5N1 Viruses in Hong Kong?"Proc. Nail. Acad. Sci., U.S.A., Aug. 1999, vol. 96, pp. 9363-9367.
Hatada and Fukudo, 1992, "Binding of influenza A virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Herlocher et al., "Sequence Comparisons of AIAAJ6/60 Influenza Viruses: Mutations Which Contribute to Attenuation", Virus Research, 42:11-25; (1996).
Hillman Maurice R., 2000, "Vaccines in historic evolution and perspective: a narrative of vaccine discoveries", Vaccine 18:1436-1447.
Hiromoto et al., 2000,. "Evolutionary characterization of the six internal genes of H5NI human influenza A virus . . . ", J. Gen. Virol. 81(Pt5):1293-303.
Hoffman and Banerjee, 1997. "An Infectious Clone of a Human Parainfluenza Virus Type 3", J. Virol. 71:4272-4277.
Hoffman et al., "A DNA transfection system for generation of influenza A virus from eight plasmids", PNAS, May 23, 2000, vol. 97, No. 11, pp. 6108-6113.
Hoffman et al., 2002, "Rescue of influenza B virus from eight plasmids", PNAS 99: 11411-11416.
Hoffman et al., "Unidirectional RNA polymerase 1-polymerase II transcription system for generation of influenza A virus from eight plasmids", J. of Gen Vir, 2000, 61, 2843-2847.
Hoffman et al.. "Eight-Plasmid Rescue System for Influenza A Virus". International Congress Series. 1219:1007-1013; (2001).
Hoffman et al.. "Eight-Plasmid Rescue System for Rapid Generation of Influenza Virus Vaccines", Vaccine, 20:3165-3170; (2002).
Hoffman et al.. 2000. "Ambisense approach for the generation of influenza A virus: vRNA and mRNA synthesis from one template", Virology 267:310-7.
Hoffmann et al., "Characterization of the Influenza A Virus Gene Pool in Avian Species in Southern China: Was H6N1 a Derivative or a Precursor of H5N1?" J. Virology. 2000. vol. 74. No. 14. pp. 6309-6315.
Hoffmann et al., 2005, "Role of specific hemagglutinin amino acids in the immunogenicity . . . " Proc. Natl. Acad. Sci. U.S.A. 102(36):12915-20. Epub Aug. 23, 2005.
Hoffmann et al., "Universal primer set for the full-length amplification of all Influenza A viruses." Arch Virol. Dec. 2001; 146(12):2275-89.
Hoffmann, Erich, Aufbau eines RNA-Polymerase I-Vektorsystems zur gezielten Mutagenese von Influenza A Vlren, Glessen 1997 (Doctoral Dissertation).With translation (Generation of an RNA-Polymerase Vector System for the Selective Mutagenesis of Influenza A).
Huang et al.. 1990, "Determination of Influenza virus proteins required for genome replication". J Virol. 64( 11 ):5669-5673.
Kaplan et al.. 1985. "In vitro Synthesis of Infectious Poliovirus RNA". Proc. Natl. Acad. Sci. USA 82:8424-8428.

(56) References Cited

OTHER PUBLICATIONS

Katinger et al., "Attenuated Influenza Virus as a Vector for Mucosal Immunization against HIV-1", Vaccines, pp. 315-319, (1997).
Kato et al., 1996, "Initiation of Sendai Virus Multiplication from Transfected cDNA or RNA with Negative or Positive Sense", Genes Cells 1 :569-579.
Keitel. et al., "Live Cold-Adapted, Reassortant Influenza Vaccines (USA)," Textbook of Influenza, Chapter 28, pp. 373-390 (1998).
Kimura et al., 1993, "An in vivo study of the replication origin in the influenza virus complementary RNA". J Biochem (Tokyo) 113(1):88-92.
Kimura et al., 1992, Transcription of a recombinant influenza virus RNA in cells that can express the influenza virus RNA polymerase and nucleoprotein genes•, J Gen Virol. 73 (Pt 6):1321-1328.
Kobayashi, 1992, Reconstitution of influenza virus RNA polymerase from three subunits expressed using recombinant baculovirus system. Virus Res. 22(3):235-245.
Konarska et al., 1990, "Structure of RNAs replicated by the DNA-dependent T7 RNA polymerase", Cell. 63(3):609-18.
Krystal et al., 1986, Expression of the Three Influenza Virus Polymerase Proteins in a Single Cell Allows Growth Complementation of Viral Mutants•, Proc. Nail. Acad. Sci. USA 83:2709-2713.
Kunkel, 1985. "Rapid and Efficient Site-Specific MutagenesiS without Phenotypic Selection", Proc. Natl. Acad. Sci. USA 82:488•492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci U S A.92(1 0):4477-81.
Lee et al., Cross-reactive H1N1 antibody responses to a live attenuated influenza vaccine in children: implication for selection of vaccine strains. J Infect Dis. Nov. 1, 2003;188(9):1362-6. Epub Oct. 16, 2003.
Lehninger, Principles of Biochemistry, 4th Edition, Nelson and Cox, pp. 86 and 87, 2005.
Levis et al., 1986, "Deletion Mapping of Sindbis Virus 01 RNAs Derived from cDNAs Defines the Sequences Essential for Replication and Packaging", Cell 44:137-145.
Li et al.. 1999, "Recombinant influenza A virus vaccines for the pathogenic human A/Hong Kong/97 (H5N1) viruses," J. of Infectious Diseases. 179:1132-8.
Luytjes et al., "Amplification, expression, and packaging of foreign gene by influenza virus," 1989, Cell, 59:1107-1113.
Maassab et al., The Development of Live Attenuated Cold-Adapted Influenza Virus Vaccine for Humans, Reviews in Medical Virology, 1999, vol. 9, pp. 237-244.
Maassab et al.. "Evaluation of a Cold-Recombinant Influenza Virus Vaccine in Ferrets", J. of Infectious Diseases. 146:780-790; (1982).
Maassab, Adaptation and growth characteristics of influenza virus at 25 degrees C Nature. 213:612-614 (1967).
Marozin et al., Antigenic and genetic diversity among swine influenza a HINI and HIN2 viruses in Europ J Gen Virol Apr. 2002;83 (Pt 4):735-745.
Martin at al., 1998, "Studies of the Binding Properties of Influenza Hemagglutinin Receptor-Site Mutants", Virology 241:101-111.
McCullers Jonathan A et al: "Multiple genotypes of influenza B virus circulated between 1979 and 2003" Journal of Virology, vol. 78, No. 23, Dec. 2004, pp. 12817-12828.
McCullers Jonathan A et al: "Reassortment and insertion-deletion are strategies for the evolution of influenza B viruses in nature" Journal of Virology, vol. 73, No. 9, Sep. 1999, pp. 7343-7348.
Mena et al., 1994, "Synthesis of biologically active influenza virus core proteins using a vaccinia virus-T7 RNA polymerase expression system", J Gen Virol. 75 (Pt 8):2109-14.
Mena et al., 1996, "Rescue of a Synthetic Chloramphenicol Acetyltransferase RNA into Influenza Virus-Like Particles Obtained from Recombinant Plasmids", J. Virol. 70: 5015-S024.
Merten at at. "Production of influenza virus in Cell Cultures for Vaccine Preparation", Novel Strategies in Design and Production of Vaccines, pp. 141-151; (1996).

MMWR of Mar. 4, 2005, vol. 54, No. 8, 193-196, Update—Infuenza Activity—United States 2004-2005 Season.
MMWR, Prevention and Control of Influenza Recommendations of the Advisory Committee on Immunization Practices (ACIP), 2004, vol. 53, pp. 1-40.
Moyer et al., 1991, "Assembly and transcription of synthetic vesicular stomatitis virus nucleocapsids", J Virol. 65(5):2170-8.
Murphy & Coelingh, "Principles Underlying the Development and Use of Live Attenuated Cold-Adapted Influenza A and B Virus Vaccines", ViralImmunol. 15:295-323; (2002).
Muster et al., 1991, "An influenza A virus containing influenza B virus 5' and 3' noncoding regions on the neuraminidase gene is attenuated in mice:". Proc Natl Acad Sci U S A.88(12):5177-81.
Naito and Ishihama, 1976, "Function and Structure of RNA Polymerase from Vesicular Stomatitis Virus", J. Biol. Chern. 251 :4307-4314.
Nakajima et al., 2003. "Restriction of Amino Acid Change in Influenza A Virus H3HA: Comparison of Amino Acid Changes Observed . . . "; J, of Virology 77(18):10088-10098.
Nara et al., 1987. "Simple, Rapid, Quantitative, Syncytlum-Fonmlng Mlcorassay for the Detection of Human Immunodeficiency Virus Neutralizing Antibody", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation of Cellular Pre-mRNAs", Mol. Cell1 :991•1000.
Neumann et al., 1994, "RNA Polymerase I-Mediated Expression of Influenza Viral RNA Molecules", Virol, 202:477-479.
Neumann et al. Generation of influenza A viruses entirely from cloned cDNAs, Proc. Natl. Acad. Sci.. Microbiology, Aug. 1999, vol. 96, pp. 9354-9350.
Neumann, et al., "Genetic Engineering of Influenza and Other Negative-Strand RNA Viruses Containing Segmented Genomes," Advances in Virus Research, 1999; 53: 265-300.
Neumann et al., "Reverse Genetics for the Control of Avian Influenza," Avian Diseases, 2003, vol. 47, pp. 882-887.
Nichol et al., "Effectiveness of live, attenuated Intranasal influenza virus vaccine in healthy, working adults: a randomized controlled trial", (1999) JAMA 282:137-144.
Palese et al., 1996, "Negative-Strand RNA Viruses: Genetic Engineering and Applications", Proc. Natl. Acad. Sci. USA 93,11354-11358.
Parkin et al.. "Temperature Sensitive Mutants of Influenza A Virus Generated by Reverse Genetics . . . ". Vir. Res .• 46:31-44; (1996).
Parkin N. et al., "Genetically Engineered Live Attenuated Influenza A Virus Vaccine Candidates", J. Virol., pp. 2772-2778; (1997).
Pattnaik et al., 1991, •Cells that express all fIVe proteins of vesicular stomatitis virus from cloned cDNAs support replication, assembly, and budding of defective Interfering particles, Proc Nail Acad Sci USA. 88(4):1379-83.
Peeters et al., 1999, "Rescue of Newcastle Disease Virus from Cloned cDNA: Evidence that Cleavability of the Fusion Protein is a Major Determinant for Virulence", J. Virol. 73:5001-5009.
Pekosz et al., 1999, "Reverse genetics of negative-strand RNA viruses: closing the circle", Proc Natl Acad Sci USA. 96(16):8804-6.
Percy et al., 1994, "Expression of a foreign protein by influenza A virus", J Virol 68(7):4486-92.
Perez, Daniel R. et al., "The Matrix 1 Protein of Influenza A Virus Inhibits the Transcriptase Activity of a Model Influenza Reporter Genome in Vivo", Article No. VY989318, Virology, 1998. vol. 249. pp. 52-61.
Pleschka et al., 1996, "A Plasmid-Based Reverse Genetics System for Influenza A Virus", J. Virol. 70:4188-4192.
Qiu et. al.. 1994, "The influenza virus NS1 protein is a poly(A)-binding protein that inhibits nuclear export of mRNAs containing poly(A)", J Virol. 68(4):2425-32.
Qiu et.al., 1995. The influenza virus NS1 protein binds to a specific region in human U6 snRNA and inhibits U6-U2 and U6-U4 snRNA . . . , RNA 1:304-316.
Racaniello et al. 1981. "Cloned Poliovirus Complementary DNA is Infectious in Mammalian Cells", Science 214:916-919.
Radecke et al. 1995, "Rescue of measles viruses from cloned DNA". EMBO J. 14(23):5773-84.

(56) References Cited

OTHER PUBLICATIONS

Radecke et al.. "Reverse Genetics Meets the Nonsegmented Negative-Strand RNA Viruses", Medical Virology. vol. 7: 49-63 (1997).
Roberts and Rose. 1998. "Recovery of Negative-Strand RNA Viruses from Plasmid DNAs: a Positive Approach Revitalizes a Negative Field", Virol. 247:1-6.
Rose et al., 1996, "Positive Strands to the Rescue Again: . . . " PNAS USA 94:14998-15000.
Schlesinger et al., 1995. "RNA viruses as vectors for the expression of heterologous proteins", Mol Biotechnol. 3(2):155-165.
Schlicki et al., Plasmid-only rescue of influenza A virus vaccine candidates, Philosophical Transactions of the Royal Society of London Series S, 2001, vol. 356, p. 1965-1973.
Schnell et al.. 1994. "Infectious Rabies Viruses from Cloned eDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
Seong et al.. 1992. A new method for reconstituting influenza polymerase and RNA in vitro: a study of the promoter elements for cRNA and vRNA synthesis in vitro and viral rescue in vivo. Virology. 166(1):247-260.
Sharma et al., "Comparative Sequence Analysis on Different Strains of Swine Influenza Virus Sub-type H1N1 for Neuraminidase and Hemagglutinin," Journal of Proteomics & Bioinformatics, vol. 3(2) : 055-060 (2010).
Shortridge et al., 1998, "Characterization of avian H5NI influenza viruses . . . ", Virology 252(2):331-42.
Sidhu et al., 1995, "Rescue of synthetic measles virus minireplicons: measles genomic termini direct efficient expression and propagation of a reporter gene". Virology, 208(2):600-607.
Snyder et al., Four Viral Genes Independently Contribute to Attenuation of Live Influenza A/Ann Arbor/6/60 (H2N2) Cold-Adapted . . . J, Virol.. 62:488-95; (1988).
Suarez et al., "Comparisons of Highly Virulent H5NI Influenza A Viruses Isolated from Humans and Chickens from Hong Kong", Journal of Virology, vol. 72, No. 8 (1998).
Subbarao et al., The Attenuation Phenotype Conferred by the M Gene of the Influenza A/Ann Arbor/6/60 Cold-Adapted Virud (H2N2) on the . . . Virus. Res., 25:37-50; (1992).
Subbarao et al., "Sequential Addition of Temperature-Sensitive Missense Mutations into the PB2 Gene of Influenza A Transfectanl . . . ". J. of Vir., Am. Society for Microbiology. Oct. 1995. pp. 5969-5977.
Subbarao, K., et al., "Evaluation of Genetically Modified Reassortant H5N1 Influenza A Virus Vaccine Candidate Generated by Plasmid-Based Reverse Genetics." Virology (2003) 305: 192-200.
Suguitan et al., 2006, "Live, attenuated influenza A H5NI candidate vaccines . . . ", PLoS Med. Sep. 2006;3(9):e360.
Szewczyk et al., 1988, •Purification, Thioredoxin Renaturation, and Reconstituted Activity of the Three Subunits of the Influenza A Virus RNA Polymerase. Proc. Nat. Acad. Sci. USA 85:7907-7911.
Taylor et al., 1990, "Newcastle Disease Virus Fusion Protein Expressed in a Fowlpox Virus Recombinant Confers Protection in ChiCkens", J. Viral. 64:1441-1450.
UniProtKB Database <http://www.uniprot.org/uniprot/B2ZV32. txt> Database accession No. B2ZV32_91NFA, Jul. 1, 2008.
Ward et al., 1988, "Direct Measurement of the Poliovirus RNA Polymerase Error Frequency in Vitro", J. Virol. 62:558-562.
Wareing at al., 2001. Immunogenic and Isotype-Specific Responses to Russian and US Cold-Adapted Influenza A Vaccine Donor Strains . . . , J of Medical Virology 65:171-177.
Webby et al., 2004, "Responsiveness to a pandemic alert: use of reverse genetics for rapid development of influenza vaccines", Lancet 363:1099-1103.
Whelan et al., 1995, "Effiecient recovery of infectious vesicular stomatitis virus entirely from cDNA clones", Proc.Natl.Acad.Sci. USA 92: 8388-8392.
Xu et al., 1995 #AAB06964 (abstract only).
Xu et al., 1996, "Genetic Variation in Neuraminidase Genes of Influenza A (H3N2) Viruses", Virology 224:175-183.
Xu, Xiyan et al., "Genetic Characterization of the Pathogenic Influenza A/Goose/Guandong/1/96 (H5N1) Virus: Similarly of its Hemagglutinin Gene to Those of H5N1 Virus form the 1997 Outbreaks in Hong Kong", Article 10 viro., Virology, 1999, vol. 261, pp. 15-19.
Yamanaka et al.. "In vivo analysis of the promoter structure of the influenza virus RNA genome using a transfection system with an engineered RNA." Proc Nail Aced Sci USA 88: 5369-5373. 1991.
Yu et al., 1995, "Functional cDNA clones of the human respiratory syncytial (RS) virus N, P, and L proteins support replication RS virus genomic RNA analogs and define minimal trans-acting requirements for RNA replication", J Virol. 69(4):2412-9.
Yusoff et al.. 1987, "Nucleotide Sequence Analysis of the L Gene of Newcastle Disease Virus: Homologies with Sendi and Vesicular Stomatitis Viruses" Nucleic Acids Res. 15: 3961-3976.
Zaghouani el al., 1991, "Induction of antibodies to the envelope protein of the human immunodeficiency virus by Immunization with monoclonal anti-idiotypes", Proc. Natl. Acad. Sci. USA 88:5645-5649.
Zaghouani et al., 1992. "Cells Expressing an H Chain to Gene Carrying a Viral T Cell Epitope are Lysed by Specific Cytolytic T Cells", J. Immunol. 148:3604-3609.
Zhang and Air, 1994, "Expression of Functional Influenza Virus A Polymerase Proteins and Template from Cloned cDNAs in Recombinant Vaccine Virus Infected Cells", Biochem. Biophys. Res. Commun. 200:95-101.
Zhang et al.. Persistence of four related human immunodeficiency virus subtypes during the course of zidovudine therapy . . . J. Virol. 1994 66: 425-432.
Zhou et al., 1999, "Rapid evolution ofH5Nl influenza viruses . . . ," J. Virol. 73(4):3366-74.
Zhou, Yan, et al., "Membrane-Anchored Incorporation of a Foreign Protein in Recombinant Influenza Virions", Article No. VY989169, Virology, 1998, vol. 246, pp. 83-94.
Zobel et al, 1993, "RNA polymerase I catalysed transcription of insert viral cDNA", Nucleic Acids Res. 21 (16):3607-14.
International Search Report and Written Opinion mailed on: Dec. 29, 2009 in International Application No. PCT/US2009/050070 filed on Jul. 9, 2009 and published as WO 2010/005144 on Jan. 14, 2010.
International Preliminary Report on Patentability mailed on: Jan. 11, 2011 in International Application No. PCT/US2009/050070 filed on Jul. 9, 2009 and published as WO 2010/005144 on Jan. 14, 2010.
Written Opinion mailed on: Jul. 18, 2008 in International Application No. PCT/US2004/19372 filed on Jun. 16, 2004 and published as: WO 2005/018539 on Mar. 3, 2005.
International Preliminary Report on Patentability mailed on: Sep. 9, 2008 in International Application No. PCT/US2004/19372 filed on Jun. 16, 2004 and published as: WO 2005/018539 on Mar. 3, 2005.
International Search Report and Written Opinion mailed on: Aug. 13, 2008, in International Application No. PCT/US2006/007630 filed on Jun. 3, 2006 and published as: WO 2006/098901 on Sep. 21, 2006.
International Preliminary Report on Patentability mailed on: Mar. 10, 2009, in International Application No. PCT/US2006/007630 filed on Jun. 3, 2006 and published as: WO2006/098901 on Sep. 21, 2006.
Supplemental European Search Report dated: Oct. 21, 2009 in European Patent Application No. EP 06736880.3 filed on Mar. 6, 2006 and published as EP1856271 on Sep. 21, 2006.
Extended European Search Report dated: Dec. 29, 2011 in European Patent Application No. EP 09795168 filed on Jul. 9, 2009 based on International Application No. PCT/US2009/050070.
Extended European Search Report dated: Mar. 15, 2012 in European Patent Application No. EP 11008240 filed on Mar. 6, 2006 based on International Application No. PCT/US2009/050070.
Extended European Search Report dated: Jun. 4, 2012 in European Patent Application No. EP 12162668 filed on Mar. 6, 2006 based on International Application No. PCT/US2009/050070.
Office Action mailed on: Dec. 8, 2008 in U.S. Appl. No. 10/870,690, filed Jun. 16, 2004 and issued as 7,566,458 on Jul. 28, 2009.
Office Action mailed on: Mar. 18, 2008 in U.S. Appl. No. 10/870,690, filed Jun. 16, 2004 and issued as 7,566,458 on Jul. 28, 2009.
Office Action mailed on: Aug. 7, 2007 in U.S. Appl. No. 10/870,690, filed Jun. 16, 2004 and issued as 7,566,458 on Jul. 28, 2009.

(56) References Cited

OTHER PUBLICATIONS

Office Action mailed on: Aug. 1, 2008 in U.S. Appl. No. 11/368,246, filed Mar. 6, 2006 and issued as 7,459,162 on Dec. 2, 2008.
Office Action mailed on: Oct. 18, 2007 in U.S. Appl. No. 11/368,246, filed Mar. 6, 2006 and issued as 7,459,162 on Dec. 2, 2008.
Office Action mailed on: Feb. 18, 2010 in U.S. Appl. No. 12/262,215 and published as: 2009-0175898 on Jul. 9, 2009, now abandoned.
Office Action mailed on: Nov. 4, 2009 in U.S. Appl. No. 12/262,215 and published as: 2009-0175898 on Jul. 9, 2009, now abandoned.
Office Action mailed on: Mar. 8, 2010 in U.S. Appl. No. 12/399,077, filed Mar. 6, 2009 and published as 2009/0175908 on Jul. 9, 2009, now abandoned.
Office Action mailed on: Jun. 17, 2011, in U.S. Appl. No. 12/858,386, filed Aug. 17, 2010 and published as 2011/0070263 on Mar. 24, 2011.
Office Action mailed on: Jul. 21, 20121, in U.S. Appl. No. 12/877,000, filed Sep. 7, 2010 and issued as: 8,048,430 on: Nov. 1, 2011.
Office Action mailed on: Nov. 23, 2010, in U.S. Appl. No. 12/877,000, filed Sep. 7, 2010 and issued as: 8,048,430 on: Nov. 1, 2011.
Office Action mailed on: Feb. 2, 2012 in U.S. Appl. No. 13/247,903, filed Sep. 28, 2011 and published as 2012/0034265 on Feb. 9, 2012.
Office Action mailed on: Aug. 16, 2012 in U.S. Appl. No. 13/329,123, filed Dec. 16, 2011.
Office Action mailed on: Apr. 25, 2012 in U.S. Appl. No. 13/329,123 filed Dec. 16, 2011.
Supplemental European Search Report dated: Aug. 27, 2012 in European Patent Application No. EP 04785947 filed on Jul. 9, 2009 based on International Application No. PCT/US2004/019372.
Database UniProt [Online] EBI Nov. 1, 1996 "Influenza A Virus (A/Beijing/32/1992 (H3N2)" Database accession No. Q82525.
Database EMBL [Online] EBI; Nov. 5, 1999 "Influenza A Virus (A/Nagasaki/97/95(H3N2) HA gene for Hemagglutinin", Database accession No. AB019357.
Database EMBL [Online] EBI; Sep. 23, 1997, "Influenza A virus (A/Vienna/47/96v(H3N2) hemagglutinin mRNA," Database accession No. AF017272.
Li et al, Recombinant influenza A virus vaccines for the pathogenic human A/Hong Kong/97 (H5N1) viruses, Journal of Infectious Diseases, vol. 179, no. May 5, 1999, pp. 1132-1138.
Office Action mailed on: Nov. 14, 2012 in U.S. Appl. No. 13/538,972, filed Jun. 29, 2012 and published as: 2012/0301503 on Nov. 12, 2012.
World Health Organization, Weekly epidemiological record 27, Feb. 2004, No. 9, pp. 85-92.
Extended European Search Report dated: Mar. 18, 2013 in European Patent Application No. EP 12193604 filed on Jun. 16, 2004.
Andreas et al., "A host restriction-based selection system for influenza haemagglutinin transfectant viruses," Journal of General Virology, vol. 79, No. 6, Jun. 1998, pp. 1405-1409, & Database UniProt [Online] 1-14 "Influenza A virus (A/Vienna/47/96V(H3N2))" Database accession No. O37162.
Wang et al., "Cloning of the canine RNA polymerase I promoter and establishment of reverse genetics for influenza A and B in MOCK cells", Virology Journal, Biomed Central, London, GB, vol. 4, No. 1, Oct. 23, 2007.
Database EMBL [Online] 1-13 E.B.I. Hinxton U.K.; Sep. 11, 2007, Komadina N and Deed N: "Influenza A virus (A/Solomon Islands/3/2006(HINI)) segment 6 neuraminidase (NA) gene, partial cds.", XP002692397, Database accession No. EU124136.
Database UniProt [Online] 1-13 E.B.I. Hinxton U.K.; Oct. 2, 2007, Garten R et al: "Hemagglutinin; A/Solomon Islands/3/2006 (HINI)", XP002692396, Database accession No. A7UPX0.
Database EMBL [Online] E. B. I. Hinxton U. K. ; May 29, 2007, Li D et al: "Influenza A virus (A/Hanoi/BM344/2006(H1N1)) genomic RNA, segment 6, complete sequence", XP002692398, Database accession No. AB286007.
Chutinimithul et al., "Molecular 1-13 characterization and phylogenetic analysis of H1N1 and H3N2 human influenza A viruses among infants and children in Thailand", Virus Research, Amsterdam, NL, vol. 132, No. 1-2, Dec. 21, 2007, pp. 122-131.
Extended European Search Report dated: Mar. 5, 2013 in European Patent Application No. EP 12177899 filed on Jun. 9, 2009.
Office Action mailed on: Jun. 28, 2013 in U.S. Appl. No. 13/708,743, filed Dec. 7, 2012 and published as: 2013-0156810 on Jun. 20, 2013.
Sasaki et al., Comparison of the Influenza Virus-Specific Effector and Memory B-Cell Responses to Immunization of Children and Adults with Live Attenuated or Inactivated Influenza Virus Vaccines, 2007, Journal of Virology, vol. 81, No. 1, pp. 215-228.

* cited by examiner

SEQ ID NO:1- Nucleotide Sequence of ca A/Uruguay/716/07 HA
Entire molecule length: 1757 bp

```
   1  AAAGCAGGGG ATAATTCTAT TAACCATGAA GACTATCATT GCTTTGAGCT
  51  ACATTCTATG TCTGGTTTTC GCTCAAAAAC TTCCTGGAAA TGACAACAGC
 101  ACGGCAACGC TGTGCCTTGG GCACCATGCA GTACCAAACG GAACGATAGT
 151  GAAAACAATC ACGAATGACC AAATTGAAGT TACTAATGCT ACTGAGCTGG
 201  TTCAGAGTTC CTCAACAGGT GAAATATGCG ACAGTCCTCA TCAGATCCTT
 251  GATGGAGAAA ACTGCACACT AATAGATGCT CTATTGGGAG ACCCTCAGTG
 301  TGATGGCTTC CAAAATAAGA AATGGGACCT TTTTGTTGAA CGCAGCAAAG
 351  CCTACAGCAA CTGTTACCCT TATGATGTGC CGGATTATGC CTCCCTTAGG
 401  TCACTAGTTG CCTCATCCGG CACACTGGAG TTTAACAATG AAAGCTTCAA
 451  TTGGACTGGA GTCACTCAAA ACGGAACAAG CTCTTCTTGC ATAAGGAGAT
 501  CTAATAACAG TTTCTTTAGT AGATTGAATT GGTTGACCCA CTTAAAATTC
 551  AAATACCCAG CATTGAACGT GACTATGCCA AACAATGAAA AATTTGACAA
 601  ATTGTACATT TGGGGGGTTC ACCACCCGGG TACGGACAAT GACCAAATCT
 651  TCCCGTATGC TCAAGCATCA GGAAGAATCA CAGTCTCTAC CAAAAGAAGC
 701  CAACAAACTG TAATCCCGAA TATCGGATCT AGACCCAGAG TAAGGAATAT
 751  CCCCAGCAGA ATAAGCATCT ATTGGACAAT AGTAAAACCG GGAGACATAC
 801  TTTTGATTAA CAGCACAGGG AATCTAATTG CTCCTAGGGG TTACTTCAAA
 851  ATACGAAGTG GGAAAAGCTC AATAATGAGA TCAGATGCAC CCATTGGCAA
 901  ATGCAATTCT GAATGCATCA CTCCAAATGG GAGCATTCCC AATGACAAAC
 951  CATTCCAAAA TGTAAACAGG ATCACATACG GGGCCTGTCC CAGATATGTT
1001  AAGCAAAACA CTCTGAAATT GGCAACAGGG ATGCGAAATG TACCAGAGAA
1051  ACAAACTAGA GGCATATTTG GCGCAATCGC GGGTTTCATA GAAAATGGTT
1101  GGGAGGGAAT GGTGGATGGT TGGTACGGTT TCAGGCATCA AAATTCTGAG
1151  GGAATAGGAC AAGCAGCAGA TCTCAAAAGC ACTCAAGCAG CAATCGATCA
1201  AATCAATGGG AAGCTGAATA GGTTGATCGG GAAAACCAAC GAGAAATTCC
1251  ATCAGATTGA AAAGGAATTC TCAGAAGTCG AAGGGAGGAT TCAGGACCTT
1301  GAGAAATATG TTGAGGACAC CAAAATAGAT CTCTGGTCAT ACAACGCGGA
1351  GCTTCTTGTT GCCCTGGAGA ACCAACATAC AATTGATCTA ACTGACTCAG
1401  AAATGAACAA ACTGTTTGAA AAAACAAAGA AGCAACTGAG GGAAAATGCT
1451  GAGGATATGG GCAATGGTTG TTTCAAAATA TACCACAAAT GTGACAATGC
1501  CTGCATAGGA TCAATCAGAA ATGGAACTTA TGACCACGAT GTATACAGAG
1551  ATGAAGCATT AAACAACCGG TTCCAGATCA AGGGCGTTGA GCTGAAGTCA
1601  GGATACAAAG ATTGGATCCT ATGGATTTCC TTTGCCATAT CATGTTTTTT
1651  GCTTTGTGTT GCTTTGTTGG GGTTCATCAT GTGGGCCTGC CAAAAAGGCA
1701  ACATTAGGTG CAACATTTGC ATTTGAGTGC ATTAATTAAA AACACCCTTG
1751  TTTCTAC
```

SEQ ID NO:2- Amino Acid Sequence of ca A/Uruguay/716/07 HA
Entire molecule length: 566 aa

```
   1  MKTIIALSYI LCLVFAQKLP GNDNSTATLC LGHHAVPNGT IVKTITNDQI
  51  EVTNATELVQ SSSTGEICDS PHQILDGENC TLIDALLGDP QCDGFQNKKW
 101  DLFVERSKAY SNCYPYDVPD YASLRSLVAS SGTLEFNNES FNWTGVTQNG
 151  TSSSCIRRSN NSFFSRLNWL THLKFKYPAL NVTMPNNEKF DKLYIWGVHH
 201  PGTDNDQIFP YAQASGRITV STKRSQQTVI PNIGSRPRVR NIPSRISIYW
 251  TIVKPGDILL INSTGNLIAP RGYFKIRSGK SSIMRSDAPI GKCNSECITP
 301  NGSIPNDKPF QNVNRITYGA CPRYVKQNTL KLATGMRNVP EKQTRGIFGA
 351  IAGFIENGWE GMVDGWYGFR HQNSEGIGQA ADLKSTQAAI DQINGKLNRL
 401  IGKTNEKFHQ IEKEFSEVEG RIQDLEKYVE DTKIDLWSYN AELLVALENQ
 451  HTIDLTDSEM NKLFEKTKKQ LRENAEDMGN GCFKIYHKCD NACIGSIRNG
 501  TYDHDVYRDE ALNNRFQIKG VELKSGYKDW ILWISFAISC FLLCVALLGF
 551  IMWACQKGNI RCNICI*
```

Figure 1A

SEQ ID NO:3- Nucleotide Sequence of ca A/Uruguay/716/07 NA
Entire molecule length: 1458 bp

```
   1    GCAAAAGCAG GAGTAAAGAT GAATCCAAAT CAAAAGATAA TAACGATTGG
  51    CTCTGTTTCT CTCACCATTT CCACAATATG CTTCTTCATG CAAACTGCCA
 101    TCTTGATAAC TACTGTAACA TTGCATTTCA AGCAATATGA ATTCAACTCC
 151    CCCCCAAACA ACCAAGTGAT GCTGTGTGAA CCAACAATAA TAGAAAGAAA
 201    CATAACAGAG ATAGTGTATC TGACCAACAC CACCATAGAG AAGGAAATAT
 251    GCCCCAAACT AGCAGAATAC AGAAATTGGT CAAAGCCGCA ATGTGACATT
 301    ACAGGATTTG CACCTTTTTC TAAGGACAAT TCGATTAGGC TTTCCGCTGG
 351    TGGGGACATC TGGGTGACAA GAGAACCTTA TGTGTCATGC GATCCTGACA
 401    AGTGTTATCA ATTTGCCCTT GGACAGGGAA CAACACTAAA CAACGTGCAT
 451    TCAAATGACA CAGTACATGA TAGGACCCCT TATCGGACCC TATTGATGAA
 501    TGAGTTAGGT GTTCCTTTTC ATCTGGGGAC CAAGCAAGTG TGCATAGCAT
 551    GGTCCAGCTC AAGTTGTCAC GATGGAAAAG CATGGCTGCA TGTTTGTATA
 601    ACGGGGGATG ATAAAAATGC AACTGCTAGC TTCATTTACA ATGGGAGGCT
 651    TGTAGATAGT ATTGTTTCAT GGTCCAAAGA AATCCTCAGG ACCCAGGAGT
 701    CAGAATGCGT TTGTATCAAT GGAACTTGTA CAGTAGTAAT GACTGATGGG
 751    AGTGCTTCAG GAAAAGCTGA TACTAAAATA CTATTCATTG AGGAGGGGAA
 801    AATCGTTCAT ACTAGCATAT TGTCAGGAAG TGCTCAGCAT GTCGAGGAGT
 851    GCTCCTGCTA TCCTCGATAT CCTGGTGTCA GATGTGTCTG CAGAGACAAC
 901    TGGAAAGGCT CCAATAGGCC CATCGTAGAT ATAAACATAA AGGATCATAG
 951    CATTGTTTCC AGTTATGTGT GTTCAGGACT TGTTGGAGAC ACACCCAGAA
1001    AAAACGACAG CTCCAGCAGT AGCCATTGTT TGGATCCTAA CAATGAAGAA
1051    GGTGGTCATG GAGTGAAAGG CTGGGCCTTT GATGATGGAA ATGACGTGTG
1101    GATGGGAAGA ACGATCAGCG AGAAGTCACG CTTAGGGTAT GAAACCTTCA
1151    AAGTCATTGA AGGCTGGTCC AACCCTAAGT CCAAATTGCA GATAAATAGG
1201    CAAGTCATAG TTGACAGAGG TAATAGGTCC GGTTATTCTG GTATTTTCTC
1251    TGTTGAAGGC AAAAGCTGCA TCAATCGGTG CTTTTATGTG GAGTTGATAA
1301    GGGGAAGAAA AGAGGAAACT GAAGTCTTGT GGACCTCAAA CAGTATTGTT
1351    GTGTTTTGTG GCACCTCAGG TACATATGGA ACAGGCTCAT GGCCTGATGG
1401    GGCGGACATC AATCTCATGC CTATATAAGC TTTCGCAATT TTAGAAAAAA
1451    ACTCCTTG
```

SEQ ID NO:4- Amino Acid Sequence of ca A/Uruguay/716/07 NA
Entire molecule length: 469 aa

```
   1    MNPNQKIITI GSVSLTISTI CFFMQTAILI TTVTLHFKQY EFNSPPNNQV
  51    MLCEPTIIER NITEIVYLTN TTIEKEICPK LAEYRNWSKP QCDITGFAPF
 101    SKDNSIRLSA GGDIWVTREP YVSCDPDKCY QFALGQGTTL NNVHSNDTVH
 151    DRTPYRTLLM NELGVPFHLG TKQVCIAWSS SSCHDGKAWL HVCITGDDKN
 201    ATASFIYNGR LVDSIVSWSK EILRTQESEC VCINGTCTVV MTDGSASGKA
 251    DTKILFIEEG KIVHTSILSG SAQHVEECSC YPRYPGVRCV CRDNWKGSNR
 301    PIVDINIKDH SIVSSYVCSG LVGDTPRKND SSSSHCLDP  NNEEGGHGVK
 351    GWAFDDGNDV WMGRTISEKS RLGYETFKVI EGWSNPKSKL QINRQVIVDR
 401    GNRSGYSGIF SVEGKSCINR CFYVELIRGR KEETEVLWTS NSIVVFCGTS
 451    GTYGTGSWPD GADINLMPI*
```

Figure 1B

SEQ ID NO:5- Nucleotide Sequence of ca A/South Dakota/6/07HA
Entire molecule length: 1771 bp

```
   1  AAAAGCAGGG GAAAATAAAA ACAACCAGAA TGAAAGTAAA ACTACTGGTC
  51  CTGTTATGCA CATTTACAGC TACATATGCA GACACAATAT GTATAGGCTA
 101  CCATGCTAAC AACTCGACCG ACACTGTTGA CACAGTACTT GAAAAGAATG
 151  TGACAGTGAC ACACTCTGTC AACCTGCTTG AGAACAGTCA CAATGGAAGA
 201  CTATGTCTAT TAAAAGGAAT AGCCCCACTA CAATTGGGTA ACTGCAGCGT
 251  TGCCGGGTGG ATCTTAGGAA ACCCAGAATG CGAATTACTG ATTTCCAAGG
 301  AGTCATGGTC CTACATTGTA GAAAAACCAA ATCCTGAGAA TGGAACATGT
 351  TACCCAGGGC ATTTCGCTGA CTATGAGGAA CTGAGGGAGC AATTGAGTTC
 401  AGTATCTTCA CTTGAGAGGT TCGAAATATT CCCCAAAGAA AGCTCATGGC
 451  CCAACCACAC CGTAACCGGA GTGTCAGCAT CATGCTCCCA TAATGGGGAA
 501  AGCAGTTTTT ACAGAAATTT GCTATGGCTG ACGGGGAAGA ATGGTTTGTA
 551  CCCAAACCTG AGCAAGTCCT ATGCAAACAA CAAAGAAAAA GAAGTCCTTG
 601  TACTATGGGG TGTTCATCAC CCGCCAAACA TAGGTAACCA AAAGGCCCTC
 651  TATCATACAG AAAATGCTTA TGTTTCTGTA GTGTCTTCAC ATTATAGCAG
 701  AAAATTCACC CCAGAAATAG CCAAAAGACC CAAAGTAAGA GATCAAGAAG
 751  GAAGAATCAA CTACTACTGG ACTCTGCTTG AACCCGGGGA TACAATAATA
 801  TTTGAGGCAA ATGGAAATCT AATAGCGCCA AGATATGCTT TCGCACTGAG
 851  TAGAGGCTTT GGATCAGGAA TCATCAACTC AAATGCACCA ATGGATAAAT
 901  GTGATGCGAA GTGCCAAACA CCTCAGGGAG CTATAAACAG CAGTCTTCCT
 951  TTCCAGAACG TACACCCAGT CACAATAGGA GAGTGTCCAA AGTATGTCAG
1001  GAGTGCAAAA TTAAGGATGG TTACAGGACT AAGGAACATC CCATCCATTC
1051  AATCCAGAGG TTTGTTTGGA GCCATTGCCG GTTTCATTGA AGGGGGGTGG
1101  ACTGGAATGG TAGATGGTTG GTATGGTTAT CATCATCAGA ATGAGCAAGG
1151  ATCTGGCTAT GCTGCAGATC AAAAAAGCAC ACAAAATGCC ATTAATGGGA
1201  TTACAAACAA GGTGAATTCT GTAATTGAGA AAATGAACAC TCAATTCACA
1251  GCAGTGGGCA AAGAATTCAA CAAATTGGAA AGAAGGATGG AAAACTTGAA
1301  TAAAAAAGTT GATGATGGGT TTATAGACAT TTGGACATAT AATGCAGAAC
1351  TGTTGGTTCT ACTGGAAAAT GAAAGGACTT TGGATTTCCA TGACTCCAAT
1401  GTGAAGAATC TGTATGAGAA AGTAAAAAGC CAGTTAAAGA ATAATGCTAA
1451  AGAAATAGGA AATGGGTGTT TTGAATTCTA TCACAAGTGT AACGATGAAT
1501  GCATGGAGAG TGTAAAGAAT GGAACTTATG ACTATCCAAA ATATTCCGAA
1551  GAATCAAAGT TAAACAGGGA GAAAATTGAT GGAGTGAAAT TGGAATCAAT
1601  GGGAGTCTAT CAGATTCTGG CGATCTACTC AACAGTCGCC AGTTCTCTGG
1651  TTCTTTTGGT CTCCCTGGGG GCAATCAGCT TCTGGATGTG TTCCAATGGG
1701  TCTTTGCAGT GTAGAATATG CATCTAAGAC CAGAATTTCA GAAATATAAG
1751  GAAAAACACC CTTGTTTCTA C
```

SEQ ID NO:6- Amino Acid Sequence of ca A/South Dakota/6/07HA
Entire molecule length: 565 aa

```
   1  MKVKLLVLLC TFTATYADTI CIGYHANNST DTVDTVLEKN VTVTHSVNLL
  51  ENSHNGRLCL LKGIAPLQLG NCSVAGWILG NPECELLISK ESWSYIVEKP
 101  NPENGTCYPG HFADYEELRE QLSSVSSLER FEIFPKESSW PNHTVTGVSA
 151  SCSHNGESSF YRNLLWLTGK NGLYPNLSKS YANNKEKEVL VLWGVHHPPN
 201  IGNQKALYHT ENAYVSVVSS HYSRKFTPEI AKRPKVRDQE GRINYYWTLL
 251  EPGDTIIFEA NGNLIAPRYA FALSRGFGSG IINSNAPMDK CDAKCQTPQG
 301  AINSSLPFQN VHPVTIGECP KYVRSAKLRM VTGLRNIPSI QSRGLFGAIA
 351  GFIEGGWTGM VDGWYGYHHQ NEQGSGYAAD QKSTQNAING ITNKVNSVIE
 401  KMNTQFTAVG KEFNKLERRM ENLNKKVDDG FIDIWTYNAE LLVLLENERT
 451  LDFHDSNVKN LYEKVKSQLK NNAKEIGNGC FEFYHKCNDE CMESVKNGTY
 501  DYPKYSEESK LNREKIDGVK LESMGVYQIL AIYSTVASSL VLLVSLGAIS
 551  FWMCSNGSLQ CRICI*
```

Figure 1C

SEQ ID NO:7- Nucleotide Sequence of ca A/South Dakota/6/07NA
Entire molecule length: 1446 bp

```
   1 AGCAAAAGCA GGAGTTTAAA ATGAACCCAA ATCAAAAGAT AATAACCATT
  51 GGATCAATCA GTATAGCAAT CGGAATAATT AGTCTAATGT TGCAAATAGG
 101 AAATATTATT TCAATATGGG CTAGTCACTC AATCCAAACT GGAAGTCAAA
 151 ACAACACTGG AATATGCAAC CAAAGAATCA TCACATATGA AAACAGCACC
 201 TGGGTGAATC ACACATATGT TAATATTAAC AACACTAATG TTGTTGCTGG
 251 AGAGGACAAA ACTTCAGTGA CATTGGCCGG CAATTCATCT CTTTGTTCTA
 301 TCAGTGGATG GGCTATATAC ACAAAAGACA ACAGCATAAG AATTGGCTCC
 351 AAAGGAGATG TTTTTGTCAT AAGAGAACCT TTCATATCAT GTTCTCACTT
 401 GGAATGCAGA ACCTTTTTTC TGACCCAAGG CGCTCTATTA AATGACAAAC
 451 ATTCAAATGG GACCGTAAAG GACAGAAGTC CTTATAGGGC CTTAATGAGC
 501 TGTCCTCTAG GTGAAGCTCC GTCCCCATAC AATTCAAAGT TCGAATCAGT
 551 TGCATGGTCA GCAAGCGCAT GCCATGATGG CATGGGCTGG TTAACAATCG
 601 GAATTTCTGG TCCAGACAAT GGAGCTGTGG CTGTACTAAA ATACAACGGA
 651 ATAATAACTG GAACCATAAA AAGTTGGAAA AAGCAAATAT TAAGAACACA
 701 AGAGTCTGAA TGTGTCTGTA TGAACGGGTC ATGTTTCACC ATAATGACCG
 751 ATGGCCCGAG TAATAAGGCC GCCTCGTACA AAATTTTCAA GATCGAAAAG
 801 GGGAAGGTTA CTAAATCAAT AGAGTTGAAT GCACCCAATT TTCATTATGA
 851 GGAATGCTCC TGTTACCCAG ACACTGGCAT AGTGATGTGT GTATGCAGGG
 901 ACAACTGGCA TGGTTCAAAT CGACCTTGGG TGTCTTTCAA TCAAAACTTG
 951 GATTATCAAA TAGGATACAT CTGCAGTGGA GTGTTTGGTG ACAATCCGCG
1001 TCCCGAAGAT GGAGAGGGCA GCTGCAATCC AGTGACTGTT GATGGAGCAA
1051 ACGGAGTAAA AGGGTTTTCA TACAAATATG ATAATGGTGT TTGGATAGGA
1101 AGGACCAAAA GTAACAGACT TAGAAAGGGG TTTGAGATGA TTTGGGATCC
1151 TAATGGATGG ACAAATACCG ACAGTGATTT CTCAGTGAAA CAGGATGTTG
1201 TAGCAATAAC TGATTGGTCA GGGTACAGCG GAAGTTTCGT CCAACATCCT
1251 GAGTTAACAG GATTGGACTG TATAAGACCT TGCTTCTGGG TTGAGTTAGT
1301 CAGAGGGCTG CCTAGAGAAA ATACAACAAT CTGGACTAGT GGGAGCAGCA
1351 TTTCTTTTTG TGGCGTTAAT AGTGATACTG CAAACTGGTC TTGGCCAGAC
1401 GGTGCTGAGT TGCCGTTCAC CATTGACAAG TAGTTCGTTG AAAAAA
```

SEQ ID NO:8- Amino Acid Sequence of ca A/South Dakota/6/07NA
Entire molecule length: 470 aa

```
  1    MNPNQKIITI GSISIAIGII SLMLQIGNII SIWASHSIQT GSQNNTGICN
 51    QRIITYENST WVNHTYVNIN NTNVVAGEDK TSVTLAGNSS LCSISGWAIY
101    TKDNSIRIGS KGDVFVIREP FISCSHLECR TFFLTQGALL NDKHSNGTVK
151    DRSPYRALMS CPLGEAPSPY NSKFESVAWS ASACHDGMGW LTIGISGPDN
201    GAVAVLKYNG IITGTIKSWK KQILRTQESE CVCMNGSCFT IMTDGPSNKA
251    ASYKIFKIEK GKVTKSIELN APNFHYEECS CYPDTGIVMC VCRDNWHGSN
301    RPWVSFNQNL DYQIGYICSG VFGDNPRPED GEGSCNPVTV DGANGVKGFS
351    YKYDNGVWIG RTKSNRLRKG FEMIWDPNGW TNTDSDFSVK QDVVAITDWS
401    GYSGSFVQHP ELTGLDCIRP CFWVELVRGL PRENTTIWTS GSSISFCGVN
451    SDTANWSWPD GAELPFTIDK *
```

Figure 1D

SEQ ID NO:9- Nucleotide Sequence of ca B/Florida/6/04 HA
Entire molecule length: 1882 bp

```
   1 AGCAGAAGCA GAGCATTTTC TAATATCCAC AAAATGAAGG CAATAATTGT
  51 ACTACTCATG GTAGTAACAT CCAATGCAGA TCGAATCTGC ACTGGAATAA
 101 CATCTTCAAA CTCACCTCAT GTGGTCAAAA CAGCCACTCA AGGGGAGGTC
 151 AATGTGACTG GTGTGATACC ACTAACAACA ACACCAACAA AATCTTATTT
 201 TGCAAATCTC AAAGGAACAA GGACCAGAGG GAAACTATGC CCAGACTGTC
 251 TCAACTGCAC AGATCTGGAT GTGGCTTTGG GCAGACCAAT GTGTGTGGGG
 301 ACCACACCTT CGGCGAAAGC TTCAATACTC CACGAAGTCA AACCTGTTAC
 351 ATCCGGGTGC TTTCCTATAA TGCACGACAG AACAAAAATC AGGCAACTAC
 401 CCAATCTTCT CAGAGGATAT GAAAATATCA GGCTATCAAC CCAAAACGTC
 451 ATCGATGCGG AAAAGGCACC AGGAGGACCC TACAGACTTG GAACCTCAGG
 501 ATCTTGCCCT AACGCTACCA GTAAGAGCGG ATTTTTCGCA ACAATGGCTT
 551 GGGCTGTCCC AAAGGACAAC AACAAAAATG CAACGAACCC ACTAACAGTA
 601 GAAGTACCAT ACATTTGTAC AGAAGGGGAA GACCAAATCA CTGTTTGGGG
 651 GTTCCATTCA GATGACAAAA CCCAAATGAA GAACCTCTAT GGAGACTCAA
 701 ATCCTCAAAA GTTCACCTCA TCTGCTAATG GAGTAACCAC ACACTATGTT
 751 TCTCAGATTG GCAGCTTCCC AGATCAAACA GAAGACGGAG GACTACCACA
 801 AAGCGGCAGG ATTGTTGTTG ATTACATGAT GCAAAAACCT GGGAAAACAG
 851 GAACAATTGT CTACCAAAGA GGTGTTTTGT TGCCTCAAAA GGTGTGGTGC
 901 GCGAGTGGCA GGAGCAAAGT AATAAAAGGG TCCTTGCCTT TAATTGGTGA
 951 AGCAGATTGC CTTCATGAAA AATACGGTGG ATTAAACAAA AGCAAGCCTT
1001 ACTACACAGG AGAACATGCA AAAGCCATAG GAAATTGCCC AATATGGGTG
1051 AAAACACCTT TGAAGCTTGC CAATGGAACC AAATATAGAC CTCCTGCAAA
1101 ACTATTAAAG GAAAGGGGTT TCTTCGGAGC TATTGCTGGT TTCCTAGAAG
1151 GAGGATGGGA AGGAATGATT GCAGGCTGGC ACGGATACAC ATCTCACGGA
1201 GCACATGGAG TGGCAGTGGC GGCGGACCTT AAGAGTACGC AAGAAGCTAT
1251 AAACAAGATA ACAAAAAATC TCAATTCTTT GAGTGAGCTA GAAGTAAAGA
1301 ATCTTCAAAG ACTAAGTGGT GCCATGGATG AACTCCACAA CGAAATACTC
1351 GAGCTGGATG AGAAAGTGGA TGATCTCAGA GCTGACACTA TAAGCTCGCA
1401 AATAGAACTT GCAGTCTTGC TTTCCAACGA AGGAATAATA AACAGTGAAG
1451 ATGAGCATCT ATTGGCACTT GAGAGAAAAC TAAAGAAAAT GCTGGGTCCC
1501 TCTGCTGTAG AGATAGGAAA TGGATGCTTC GAAACCAAAC ACAAGTGCAA
1551 CCAGACCTGC TTAGACAGGA TAGCTGCTGG CACCTTTAAT GCAGGAGAAT
1601 TTTCTCTCCC CACTTTTGAT TCACTGAACA TTACTGCTGC ATCTTTAAAT
1651 GATGATGGAT TGGATAACCA TACTATACTG CTCTATTACT CAACTGCTGC
1701 TTCTAGTTTG GCTGTAACAT TGATGCTAGC TATTTTTATT GTTTATATGG
1751 TCTCCAGAGA CAACGTTTCA TGCTCCATCT GTCTATAAGG AAGATTAGGC
1801 CTTGTATTTT CCTTTATTGT AGTGCTTGTT TGCTTGTCAT CATTACAAAG
1851 AAACGTTATT GAAAAATGCT CTTGTTACTA CT
```

SEQ ID NO:10- Amino Acid Sequence of ca B/Florida/6/04 HA

Entire molecule length: 584 aa

```
   1 MKAIIVLLMV VTSNADRICT GITSSNSPHV VKTATQGEVN VTGVIPLTTT
  51 PTKSYFANLK GTRTRGKLCP DCLNCTDLDV ALGRPMCVGT TPSAKASILH
 101 EVKPVTSGCF PIMHDRTKIR QLPNLLRGYE NIRLSTQNVI DAEKAPGGPY
 151 RLGTSGSCPN ATSKSGFFAT MAWAVPKDNN KNATNPLTVE VPYICTEGED
 201 QITVWGFHSD DKTQMKNLYG DSNPQKFTSS ANGVTTHYVS QIGSFPDQTE
 251 DGGLPQSGRI VVDYMMQKPG KTGTIVYQRG VLLPQKVWCA SGRSKVIKGS
 301 LPLIGEADCL HEKYGGLNKS KPYYTGEHAK AIGNCPIWVK TPLKLANGTK
 351 YRPPAKLLKE RGFFGAIAGF LEGGWEGMIA GWHGYTSHGA HGVAVAADLK
 401 STQEAINKIT KNLNSLSELE VKNLQRLSGA MDELHNEILE LDEKVDDLRA
 451 DTISSQIELA VLLSNEGIIN SEDEHLLALE RKLKKMLGPS AVEIGNGCFE
 501 TKHKCNQTCL DRIAAGTFNA GEFSLPTFDS LNITAASLND DGLDNHTILL
 551 YYSTAASSLA VTLMLAIFIV YMVSRDNVSC SICL*
```

Figure 1E

SEQ ID NO:11- Nucleotide Sequence of ca B/Florida/6/04 NA
Entire molecule length: 1557 bp

```
   1    AGCAGAAGCA GAGCATCTTC TCAAAACTGA GGCAAATAGG CCAAAAATGA
  51    ACAATGCTAC CTTCAACTAT ACAAACGTTA ACCCTATTTC TCACATCAGG
 101    GGGAGTGTTA TTATCACTAT ATGTGTCAGC TTCATTGTCA TACTTACTAT
 151    ATTCGGATAT ATTGCTAAAA TTTTCACAAA CAGAAATAAC TGCACCAATA
 201    ATGCCATTGG ATTGTGCAAA CGCATCAAAT GTTCAGGCTG TGAACCGTTC
 251    TGCAGCAAAA GGGGTGACAC TTCTTCTCCC AGAACCGGAG TGGACATACC
 301    CTCGTTTATC TTGCCCGGGC TCAACCTTTC AGAAAGCACT CCTAATTAGC
 351    CCCCATAGAT TCGGAGAAAC CAAAGGAAAC TCAGCTCCCT TGATAATAAG
 401    GGAACCTTTT ATTGCTTGTG GACCAACGGA ATGCAAACAC TTTGCTCTAA
 451    CCCATTATGC AGCTCAACCA GGGGGATACT ACAATGGAAC AAGAGAAGAC
 501    AGAAACAAGC TGAGGCATCT AATTTCAGTC AAATTGGGCA AAATCCCAAC
 551    AGTAGAAAAC TCCATTTTCC ATATGGCAGC TTGGAGCGGG TCCGCATGCC
 601    ATGATGGTAA AGAATGGACA TATATCGGAG TTGATGGCCC CGACAGTAAT
 651    GCATTACTCA AAATAAAATA TGGAGAAGCA TATACTGACA CATACCATTC
 701    CTATGCAAAA AACATCCTAA GGACACAAGA AAGTGCCTGC AATTGCATCG
 751    GGGGAGATTG TTATCTTATG ATAACTGATG GCCCAGCTTC AGGGATTAGT
 801    GAATGCAGAT TCCTTAAGAT TCGAGAGGGC CGAATAATAA AAGAAATATT
 851    TCCAACAGGA AGAGTAAAAC ATACTGAGGA ATGCACATGC GGATTTGCCA
 901    GCAACAAAAC CATAGAATGT GCTTGTAGAG ATAACAGTTA CACAGCAAAA
 951    AGACCCTTTG TCAAATTAAA TGTGGAGACT GATACAGCGG AAATAAGATT
1001    GATGTGCACA GAGACTTATT TGGACACCCC CAGACCAAAT GATGGAAGCA
1051    TAACAGGGCC TTGCGAATCT GATGGGGACA AAGGGAGTGG AGGCATCAAG
1101    GGAGGATTTG TTCATCAAAG AATGGCATCC AAGATTGGAA GGTGGTACTC
1151    TCGAACGATG TCTAAAACTA AAAGAATGGG GATGGGACTG TATGTAAAGT
1201    ATGATGGAGA CCCATGGACT GACAGTGAAG CCCTTGCTCT TAGTGGAGTA
1251    ATGGTTTCGA TGGAAGAACC TGGTTGGTAT CCTTTGGCT TCGAAATAAA
1301    AGATAAGAAA TGTGATGTCC CCTGTATTGG GATAGAAATG GTACATGATG
1351    GTGGGAAAAC GACTTGGCAC TCAGCAGCAA CAGCCATTTA CTGTTTAATG
1401    GGCTCAGGAC AACTGCTGTG GGACACTGTC ACAGGTGTTG ATATGGCTCT
1451    GTAATGGAGG AATGGTTGAG TCTGTTCTAA ACCCTTTGTT CCTATTTTGT
1501    TTGAACAATT GTCCTTACTG AGCTTAATTG TTTCTGAAAA ATGCTCTTGT
1551    TACTACT
```

SEQ ID NO:12- Amino Acid Sequence of ca B/Florida/6/04 NA
Entire molecule length: 466 aa

```
   1    MLPSTIQTLT LFLTSGGVLL SLYVSASLSY LLYSDILLKF SQTEITAPIM
  51    PLDCANASNV QAVNRSAAKG VTLLLPEPEW TYPRLSCPGS TFQKALLISP
 101    HRFGETKGNS APLIIREPFI ACGPTECKHF ALTHYAAQPG GYYNGTREDR
 151    NKLRHLISVK LGKIPTVENS IFHMAAWSGS ACHDGKEWTY IGVDGPDSNA
 201    LLKIKYGEAY TDTYHSYAKN ILRTQESACN CIGGDCYLMI TDGPASGISE
 251    CRFLKIREGR IIKEIFPTGR VKHTEECTCG FASNKTIECA CRDNSYTAKR
 301    PFVKLNVETD TAEIRLMCTE TYLDTPRPND GSITGPCESD GDKGSGGIKG
 351    GFVHQRMASK IGRWYSRTMS KTKRMGMGLY VKYDGDPWTD SEALALSGVM
 401    VSMEEPGWYS FGFEIKDKKC DVPCIGIEMV HDGGKTTWHS AATAIYCLMG
 451    SGQLLWDTVT GVDMAL*
```

Figure 1F

SEQ ID NO:13- Nucleotide Sequence of ca A/Wisconsin/67/05 HA
Entire molecule length: 1763 bp

```
   1 AGCAAAAGCA GGGGATAATT CTATTAACCA TGAAGACTAT CATTGCTTTG
  51 AGCTACATTC TATGTCTGGT TTTCGCTCAA AAACTTCCCG GAAATGACAA
 101 CAGCACGGCA ACGCTGTGCC TTGGGCACCA TGCAGTACCA AACGGAACGA
 151 TAGTGAAAAC AATCACGAAT GACCAAATTG AAGTTACTAA TGCTACTGAG
 201 CTGGTTCAGA GTTCCTCAAC AGGTGGAATA TGCGACAGTC CTCATCAGAT
 251 CCTTGATGGA GAAAACTGCA CACTAATAGA TGCTCTATTG GGAGACCCTC
 301 AGTGTGATGG CTTCCAAAAT AAGAAATGGG ACCTTTTTGT TGAACGCAGC
 351 AAAGCCTACA GCAACTGTTA CCCTTATGAT GTGCCGGATT ATGCCTCCCT
 401 TAGGTCACTA GTTGCCTCAT CCGGCACACT GGAGTTTAAC GATGAAAGCT
 451 TCAATTGGAC TGGAGTCACT CAAAATGGAA CAAGCTCTTC TTGCAAAAGG
 501 AGATCTAATA ACAGTTTCTT TAGTAGATTG AATTGGTTGA CCCACTTAAA
 551 ATTCAAATAC CCAGCATTGA ACGTGACTAT GCCAAACAAT GAAAAATTTG
 601 ACAAATTGTA CATTTGGGGG GTTCACCACC CGGTTACGGA CAATGACCAA
 651 ATCTTCCTGT ATGCTCAAGC ATCAGGAAGA ATCACAGTCT CTACCAAAAG
 701 AAGCCAACAA ACTGTAATCC CGAATATCGG ATCTAGACCC AGAATAAGGA
 751 ATATCCCCAG CAGAATAAGC ATCTATTGGA CAATAGTAAA ACCGGGAGAC
 801 ATACTTTTGA TTAACAGCAC AGGGAATCTA ATTGCTCCTA GGGGTTACTT
 851 CAAAATACGA AGTGGGAAAA GCTCAATAAT GAGATCAGAT GCACCCATTG
 901 GCAAATGCAA TTCTGAATGC ATCACTCCAA ATGGAAGCAT TCCCAATGAC
 951 AAACCATTTC AAAATGTAAA CAGGATCACA TATGGGGCCT GTCCCAGATA
1001 TGTTAAGCAA AACACTCTGA AATTGGCAAC AGGGATGCGA AATGTACCAG
1051 AGAAACAAAC TAGAGGCATA TTTGGCGCAA TCGCGGGTTT CATAGAAAAT
1101 GGTTGGGAGG GAATGGTGGA TGGTTGGTAC GGTTTCAGGC ATCAAAATTC
1151 TGAGGGAATA GGACAAGCAG CAGATCTCAA AAGCACTCAA GCAGCAATCA
1201 ATCAAATCAA TGGGAAGCTG AATAGGTTGA TCGGGAAAAC CAACGAGAAA
1251 TTCCATCAGA TTGAAAAAGA ATTCTCAGAA GTAGAAGGGA GAATTCAGGA
1301 CCTCGAGAAA TATGTTGAGG ACACTAAAAT AGATCTCTGG TCATACAACG
1351 CGGAGCTTCT TGTTGCCCTG GAGAACCAAC ATACAATTGA TCTAACTGAC
1401 TCAGAAATGA ACAAACTGTT TGAAAGAACA AAGAAGCAAC TGAGGGAAAA
1451 TGCTGAGGAT ATGGGCAATG GTTGTTTCAA AATATACCAC AAATGTGACA
1501 ATGCCTGCAT AGGATCAATC AGAAATGGAA CTTATGACCA TGATGTATAC
1551 AGAGATGAAG CATTAAACAA CCGGTTCCAG ATCAAAGGCG TTGAGCTGAA
1601 GTCAGGATAC AAAGATTGGA TCCTATGGAT TTCCTTTGCC ATATCATGTT
1651 TTTTGCTTTG TGTTGCTTTG TTGGGGTTCA TCATGTGGGC CTGCCAAAAA
1701 GGCAACATTA GGTGCAACAT TTGCATTTGA GTGCATTAAT TAAAAACACC
1751 CTTGTTTCTA CTA
```

SEQ ID NO:14- Amino Acid Sequence of ca A/Wisconsin/67/05 HA
Entire molecule length: 566 aa

```
   1 MKTIIALSYI LCLVFAQKLP GNDNSTATLC LGHHAVPNGT IVKTITNDQI
  51 EVTNATELVQ SSTGGICDS PHQILDGENC TLIDALLGDP QCDGFQNKKW
 101 DLFVERSKAY SNCYPYDVPD YASLRSLVAS SGTLEFNDES FNWTGVTQNG
 151 TSSSCKRRSN NSFFSRLNWL THLKFKYPAL NVTMPNNEKF DKLYIWGVHH
 201 PVTDNDQIFL YAQASGRITV STKRSQQTVI PNIGSRPRIR NIPSRISIYW
 251 TIVKPGDILL INSTGNLIAP RGYFKIRSGK SSIMRSDAPI GKCNSECITP
 301 NGSIPNDKPF QNVNRITYGA CPRYVKQNTL KLATGMRNVP EKQTRGIFGA
 351 IAGFIENGWE GMVDGWYGFR HQNSEGIGQA ADLKSTQAAI NQINGKLNRL
 401 IGKTNEKFHQ IEKEFSEVEG RIQDLEKYVE DTKIDLWSYN AELLVALENQ
 451 HTIDLTDSEM NKLFERTKKQ LRENAEDMGN GCFKIYHKCD NACIGSIRNG
 501 TYDHDVYRDE ALNNRFQIKG VELKSGYKDW ILWISFAISC FLLCVALLGF
 551 IMWACQKGNI RCNICI*
```

Figure 1G

SEQ ID NO:15- Nucleotide Sequence of ca A/Wisconsin/67/05 NA
Entire molecule length: 1445 bp

```
   1 AGCAAAAGCA GGAGTAAAGA TGAATCCAAA TCAAAAGATA ATAACGATTG
  51 GCTCTGTTTC TCTCACCATT TCCACAATAT GCTTCTTCAT GCAAATTGCC
 101 ATCTTGATAA CTACTGTAAC ATTGCATTTC AAGCAATATG AATTCAACTC
 151 CCCCCCAAAC AACCAAGTGA TGCTGTGTGA ACCAACAATA ATAGAAAGAA
 201 ACATAACAGA GATAGTGTAT CTGACCAACA CCACCATAGA GAAGGAAATA
 251 TGCCCCAAAC TAGCAGAATA CAGAAATTGG TCAAAGCCGC AATGTAACAT
 301 TACAGGATTT GCACCTTTTT CTAAGGACAA TTCGATTAGG CTTTCCGCTG
 351 GTGGGGACAT CTGGGTGACA AGAGAACCTT ATGTGTCATG CGATCCTGAC
 401 AAATGTTATC AATTTGCCCT TGGGCAGGGA ACAACACTAA ACAACGTGCA
 451 TTCAAATGAC ACAGTACATG ATAGGACCCC TTATCGGACC CTATTGATGA
 501 ATGAGTTAGG TGTTCCATTT CATCTGGGGA CCAAGCAAGT GTGCATAGCA
 551 TGGTCCAGCT CAAGTTGTCA CGATGGAAAA GCATGGCTGC ATGTTTGTGT
 601 AACGGGGGAT GATAAAAATG CAACTGCTAG CTTCATTTAC AATGGGAGGC
 651 TTGTAGATAG TATTGTTTCA TGGTCCAAAG AAATCCTCAG GACCCAGGAG
 701 TCAGAATGCG TTTGTATCAA TGGAACTTGT ACAGTAGTAA TGACTGATGG
 751 GAGTGCTTCA GGAAAAGCTG ATACTAAAAT ACTATTCATT GAGGAGGGGA
 801 AAATCGTTCA TACTAGCACA TTGTCAGGAA GTGCTCAGCA TGTCGAGGAG
 851 TGCTCCTGCT ATCCTCGATA TCTTGGTGTC AGATGTGTCT GCAGAGACAA
 901 CTGGAAAGGC TCCAATAGGC CCATAGTAGA TATAAACATA AAGGATTATA
 951 GCATTGTTTC CAGTTATGTG TGCTCAGGAC TTGTTGGAGA CACACCCAGA
1001 AAAAACGACA GCTCCAGCAG TAGCCATTGC TTGGATCCTA ACAATGAAGA
1051 AGGTGGTCAT GGAGTGAAAG GCTGGGCCTT TGATGATGGA AATGACGTGT
1101 GGATGGGAAG AACGATCAGC GAGAAGTTAC GCTCAGGATA TGAAACCTTC
1151 AAAGTCATTG AAGGCTGGTC AACCCTAAT TCCAAATTGC AGATAAATAG
1201 GCAAGTCATA GTTGACAGAG GTAATAGGTC CGGTTATTCT GGTATTTTCT
1251 CTGTTGAAGG CAAAAGCTGC ATCAATCGGT GCTTTTATGT GGAGTTGATA
1301 AGGGGAAGAA AAGAGGAAAC TGAAGTCTTG TGGACCTCAA ACAGTATTGT
1351 TGTGTTTTGT GGCACCTCAG GTACATATGG AACAGGCTCA TGGCCTGATG
1401 GGGCGGACAT CAATCTCATG CCTATATAAG CTTTCGCAAT TTTAG
```

SEQ ID NO:16- Amino Acid Sequence of ca A/Wisconsin/67/05 NA
Entire molecule length: 469 aa

```
   1 MNPNQKIITI GSVSLTISTI CFFMQIAILI TTVTLHFKQY EFNSPPNNQV
  51 MLCEPTIIER NITEIVYLTN TTIEKEICPK LAEYRNWSKP QCNITGFAPF
 101 SKDNSIRLSA GGDIWVTREP YVSCDPDKCY QFALGQGTTL NNVHSNDTVH
 151 DRTPYRTLLM NELGVPFHLG TKQVCIAWSS SSCHDGKAWL HVCVTGDDKN
 201 ATASFIYNGR LVDSIVSWSK EILRTQESEC VCINGTCTVV MTDGSASGKA
 251 DTKILFIEEG KIVHTSTLSG SAQHVEECSC YPRYLGVRCV CRDNWKGSNR
 301 PIVDINIKDY SIVSSYVCSG LVGDTPRKND SSSSSHCLDP NNEEGGHGVK
 351 GWAFDDGNDV WMGRTISEKL RSGYETFKVI EGWSNPNSKL QINRQVIVDR
 401 GNRSGYSGIF SVEGKSCINR CFYVELIRGR KEETEVLWTS NSIVVFCGTS
 451 GTYGTGSWPD GADINLMPI
```

Figure 1H

SEQ ID NO:17- Nucleotide Sequence of ca A_Solomon_Islands_3_06 HA
Entire molecule length: 1769 bp
```
   1 AGCAGGGGAA AATAAAAACA ACCAAAATGA AAGTAAAACT ACTGGTCCTG
  51 TTATGCACAT TTACAGCTAC ATATGCAGAC ACAATATGTA TAGGCTACCA
 101 TGCCAACAAC TCAACCGACA CTGTTGACAC AGTACTTGAG AAGAATGTGA
 151 CAGTGACACA CTCTGTCAAC CTGCTTGAGG ACAGTCACAA TGGAAAATTA
 201 TGTCTATTAA AAGGAATAGC CCCACTACAA TTGGGTAATT GCAGCGTTGC
 251 CGGATGGATC TTAGGAAACC CAGAATGCGA ATTACTGATT TCCAGGGAAT
 301 CATGGTCCTA CATTGTAGAA AAACCAAATC CTGAGAATGG AACATGTTAC
 351 CCAGGGCATT TCGCCGACTA TGAGGAACTG AGGGAGCAAT TGAGTTCAGT
 401 ATCTTCATTT GAGAGATTCG AAATATTCCC CAAAGAAAGC TCATGGCCCA
 451 ACCACACCAC AACCGGAGTA TCAGCATCAT GCTCCCATAA TGGGGAAAGC
 501 AGTTTTTACA AAAATTTGCT ATGGCTGACG GGGAAGAATG GTTTGTACCC
 551 AAACCTGAGC AAGTCCTATG CAAACAACAA AGAGAAAGAA GTCCTTGTAC
 601 TATGGGGTGT TCATCACCCG CCTAACATAG GTGACCAAAG GGCTCTCTAT
 651 CATACAGAAA ATGCTTATGT CTCTGTAGTG TCTTCACATT ATAGCAGAAA
 701 ATTCACCCCA GAAATAGCCA AAAGACCCAA AGTAAGAGAT CGAGAAGGAA
 751 GAATCAACTA CTACTGGACT CTACTTGAAC CCGGGGATAC AATAATATTT
 801 GAGGCAAATG GAAATCTAAT AGCGCCAAGA TATGCTTTCG CACTGAGTAG
 851 AGGCTTTGGA TCAGGAATCA TCAACTCAAA TGCACCAATG GATGAATGTG
 901 ATGCGAAGTG CCAAACACCT CAGGGAGCTA TAAACAGCAG TCTTCCTTTC
 951 CAGAATGTAC ACCCTGTCAC AATAGGAGAG TGTCCAAAGT ATGTCAGGAG
1001 TGCAAAATTA AGGATGGTTA CAGGACTAAG GAACATCCCA TCCATTCAAT
1051 CCAGAGGTTT GTTTGGAGCC ATTGCCGGTT TCATTGAAGG GGGGTGGACT
1101 GGAATGGTAG ATGGTTGGTA TGGTTATCAT CATCAGAATG AGCAAGGATC
1151 TGGCTATGCT GCAGATCAAA AAAGCACACA AAATGCCATT AATGGGATTA
1201 CAAACAAGGT GAATTCTGTA ATTGAGAAAA TGAACACTCA ATTCACAGCT
1251 GTGGGCAAAG AATTCAACAA ATTGGAAAGA AGGATGGAAA ACTTAAATAA
1301 AAAAGTTGAT GATGGGTTTA TAGACATTTG GACATATAAT GCAGAATTGT
1351 TGGTTCTACT GGAAAATGAA AGGACTTTGG ATTTCCATGA CTCCAATGTG
1401 AAGAATCTGT ATGAGAAAGT AAAAAGCCAA TTAAAGAATA ATGCCAAAGA
1451 AATAGGAAAT GGGTGTTTTG AATTCTATCA CAAGTGTAAC GATGAATGCA
1501 TGGAGAGTGT AAAAAATGGA ACTTATGACT ATCCAAAATA TTCCGAAGAA
1551 TCAAAGTTAA ACAGGGAGAA AATTGATGGA GTGAAATTGG AATCAATGGG
1601 AGTCTATCAG ATTCTGGCGA TCTACTCAAC AGTCGCCAGT TCTCTGGTTC
1651 TTTTGGTCTC CCTGGGGGCA ATCAGCTTCT GGATGTGTTC AATGGGTCT
1701 TTGCAGTGTA GAATATGCAT CTAAGACCAG AATTTCAGAA ATATAAGGAA
1751 AAACACCCTT GTTTCTACT
```
SEQ ID NO:18- Amino Acid Sequence of ca A_Solomon_Islands_3_06HA
Entire molecule length: 565 aa
```
   1 MKVKLLVLLC TFTATYADTI CIGYHANNST DTVDTVLEKN VTVTHSVNLL
  51 EDSHNGKLCL LKGIAPLQLG NCSVAGWILG NPECELLISR ESWSYIVEKP
 101 NPENGTCYPG HFADYEELRE QLSSVSSFER FEIFPKESSW PNHTTTGVSA
 151 SCSHNGESSF YKNLLWLTGK NGLYPNLSKS YANNKEKEVL VLWGVHHPPN
 201 IGDQRALYHT ENAYVSVVSS HYSRKFTPEI AKRPKVRDRE GRINYYWTLL
 251 EPGDTIIFEA NGNLIAPRYA FALSRGFGSG IINSNAPMDE CDAKCQTPQG
 301 AINSSLPFQN VHPVTIGECP KYVRSAKLRM VTGLRNIPSI QSRGLFGAIA
 351 GFIEGGWTGM VDGWYGYHHQ NEQGSYAAD QKSTQNAING ITNKVNSVIE
 401 KMNTQFTAVG KEFNKLERRM ENLNKKVDDG FIDIWTYNAE LLVLLENERT
 451 LDFHDSNVKN LYEKVKSQLK NNAKEIGNGC FEFYHKCNDE CMESVKNGTY
 501 DYPKYSEESK LNREKIDGVK LESMGVYQIL AIYSTVASSL VLLVSLGAIS
 551 FWMCSNGSLQ CRICI
```

Figure 1I

SEQ ID NO:19- Nucleotide Sequence of ca A_Solomon_Islands_3_06 NA
Entire molecule length: 1446 bp

```
   1 AGCAAAAGCA GGAGTTTAAA ATGAACCCAA ATCAAAAAAT AATAACCATT
  51 GGATCAATCA GTATAGCAAT CGGAATAATT AGTCTAATAT TGCAAATAGG
 101 AAATATTATT TCAATATGGG CTAGTCACTC AATCCAAACT GGAAGTCAAA
 151 ACCACACTGG AATATGCAAC CAAAGAATCA TCACATATGA AACAGCACC
 201 TGGGTGAATA ACACATATGT TAATATTAAC AACACCAATG TTGTTGCTGA
 251 AAAGGACAAA ACTTCAGTGA CATTGGCCGG CAATTCATCT CTTTGTTCTA
 301 TCAGTGGGTG GGCTATATAC ACAAAAGACA ACAGCATAAG AATTGGCTCC
 351 AAAGGAGATG TTTTTGTCAT AAGAGAACCT TTCATATCAT GTTCTCACTT
 401 GGAATGCAGA ACCTTTTTTC TGACCCAAGG TGCTCTATTA AATGACAAAC
 451 ATTCAAATGG GACCGTAAAG GACAGAAGTC CTTATAGGGC CTTAATGAGC
 501 TGTCCTCTAG GTGAAGCTCC GTCCCCATAC AATTCAAGGT TTGAATCAGT
 551 TGCATGGTCA GCAAGCGCAT GCCATGATGG CATGGGCTGG TTAACAATCG
 601 GAATTTCTGG TCCAGACAAT GGAGCTGTGG CTGTACTAAA ATACAACGGA
 651 ATAATAACTG AAACCATAAA AAGTTGGAAA AAGCAATAT TAAGAACACA
 701 AGAGTCTGAA TGTGTCTGTA TGAACGGGTC ATGTTTCACC ATAATGACCG
 751 ATGGCCCGAG TAATGGGGCC GCCTCGTACA AAATTTTCAA GATCGAAAAG
 801 GGGAAGGTTA CCAAAACAAT AGAGTTGAAT GCACCCAATT TTCATTATGA
 851 GGAATGTTCC TGTTACCCAG ACACTGGCAC AGTGATGTGT GTATGCAGAG
 901 ACAACTGGCA TGGTTCAAAT CGACCTTGGG TGTCTTTTAA TCAAACTTG
 951 GATTATCAAA TAGGATACAT CTGCAGTGGA GTGTTCGGTG ACAATCCGCG
1001 TCCCAAAGAT GGGGAGGGCA GCTGCAATCC AGTGACTGTT GATGGAGCAG
1051 ACGGAGTAAA AGGGTTTTCA TACAAATATG GTAATGGTGT TTGGATAGGA
1101 AGGACCAAAA GTAACAGACT TAGAAGGGG TTTGAGATGA TTTGGGATCC
1151 TAATGGATGG ACAAATACCG ACAGTGATTT CTCAGTGAAA CAGGATGTTG
1201 TAGCAATAAC TGATTGGTCA GGGTACAGCG AAGTTTTGT TCAACATCCT
1251 GAGTTAACAG GATTGGACTG TATAAGACCT GCTTCTGGG TTGAGTTAGT
1301 CAGAGGGCTG CCTAGGGAAA ATACAACAAT CTGGACTAGT GGGAGCAGCA
1351 TTTCTTTTTG TGGCGTTAAT AGTGGTACTG CAAACTGGTC TTGGCCAGAC
1401 GGTGCTGAGT TGCCGTTCAC CATTGACAAG TAGTTCGTTG AAAAAAAACT
1451 CCTTGTTTCT ACT
```

SEQ ID NO:20- Amino Acid Sequence of ca A_Solomon_Islands_3_06 NA
Entire molecule length: 470 aa

```
   1 MNPNQKIITI GSISIAIGII SLILQIGNII SIWASHSIQT GSQNHTGICN
  51 QRIITYENST WVNNTYVNIN NTNVVAEKDK TSVTLAGNSS LCSISGWAIY
 101 TKDNSIRIGS KGDVFVIREP FISCSHLECR TFFLTQGALL NDKHSNGTVK
 151 DRSPYRALMS CPLGEAPSPY NSRFESVAWS ASACHDGMGW LTIGISGPDN
 201 GAVAVLKYNG IITETIKSWK KRILRTQESE CVCMNGSCFT IMTDGPSNGA
 251 ASYKIFKIEK GKVTKTIELN APNFHYEECS CYPDTGTVMC VCRDNWHGSN
 301 RPWVSFNQNL DYQIGYICSG VFGDNPRPKD GEGSCNPVTV DGADGVKGFS
 351 YKYGNGVWIG RTKSNRLRKG FEMIWDPNGW TNTDSDFSVK QDVVAITDWS
 401 GYSGSFVQHP ELTGLDCIRP CFWVELVRGL PRENTTIWTS GSSISFCGVN
 451 SGTANWSWPD GAELPFTIDK
```

Figure 1J

SEQ ID NO:21- Nucleotide Sequence of ca B_Malaysia_2506_04_HA (1883 bp)

```
   1 GCAGAAGCAG AGCATTTTCT AATATCCACA AAATGAAGGC AATAATTGTA
  51 CTACTCATGG TAGTAACATC CAATGCAGAT CGAATCTGCA CTGGGATAAC
 101 ATCGTCAAAC TCACCACATG TTGTCAAAAC TGCTACTCAA GGGGAGGTCA
 151 ATGTGACTGG TGTAATACCA CTGACAACAA CACCCACCAA ATCTCATTTT
 201 GCAAATCTCA AAGGAACAGA AACCAGAGGG AAACTATGCC CAAAATGCCT
 251 CAACTGCACA GATCTGGACG TGGCCTTGGG CAGACCAAAA TGCACGGGGA
 301 ACATACCCTC GGCAAGAGTT TCAATACTCC ATGAAGTCAG ACCTGTTACA
 351 TCTGGGTGCT TTCCTATAAT GCACGACAGA ACAAAAATTA GACAGCTGCC
 401 TAACCTTCTC AGAGGATACG AACATATCAG GTTATCAACT CATAACGTTA
 451 TCAATGCAGA AAATGCACCA GGAGGACCCT ACAAAATTGG AACCTCAGGG
 501 TCTTGCCCTA ACGTTACCAA TGGAAACGGA TTTTTCGCAA CAATGGCTTG
 551 GGCCGTCCCA AAAAACGACA ACAACAAAAC AGCAACAAAT TCATTAACAA
 601 TAGAAGTACC ATACATTTGT ACAGAAGGAG AAGACCAAAT TACCGTTTGG
 651 GGGTTCCACT CTGATAGCGA AACCCAAATG GCAAAGCTCT ATGGGGACTC
 701 AAAGCCCCAG AAGTTCACCT CATCTGCCAA CGGAGTGACC ACACATTACG
 751 TTTCACAGAT TGGTGGCTTC CCAAATCAAA CAGAAGACGG AGGACTACCA
 801 CAAAGTGGTA GAATTGTTGT TGATTACATG GTGCAAAAAT CTGGGAAAAC
 851 AGGAACAATT ACCTATCAAA GAGGTATTTT ATTGCCTCAA AAAGTGTGGT
 901 GCGCAAGTGG CAGGAGCAAG GTAATAAAAG GATCCTTGCC TTTAATTGGA
 951 GAAGCAGATT GCCTCCACGA AAAATACGGT GGATTAAACA AAAGCAAGCC
1001 TTACTACACA GGGGAACATG CAAAGGCCAT AGGAAATTGC CCAATATGGG
1051 TGAAAACACC CTTGAAGCTG GCCAATGGAA CCAAATATAG ACCTCCTGCA
1101 AAACTATTAA AGGAAGGGGG TTTCTTCGGA GCTATTGCTG GTTTCTTAGA
1151 AGGAGGATGG GAAGGAATGA TTGCAGGTTG GCACGGATAC ACATCCCATG
1201 GGGCACATGG AGTAGCGGTG GCAGCAGACC TTAAGAGCAC TCAAGAGGCC
1251 ATAAACAAGA TAACAAAAAA TCTCAACTCT TTGAGTGAGC TGGAAGTAAA
1301 GAATCTTCAA AGACTAAGCG GTGCCATGGA TGAACTCCAC AACGAAATAC
1351 TAGAACTAGA CGAGAAAGTG GATGATCTCA GAGCTGATAC AATAAGCTCA
1401 CAAATAGAAC TCGCAGTCCT GCTTTCCAAT GAAGGAATAA TAAACAGTGA
1451 AGATGAGCAT CTCTTGGCGC TTGAAAGAAA GCTGAAGAAA ATGCTGGGCC
1501 CCTCTGCTGT AGAGATAGGG AATGGATGCT TTGAAACCAA ACACAAGTGC
1551 AACCAGACCT GTCTCGACAG AATAGCTGCT GGTACCTTTG ATGCAGGAGA
1601 ATTTTCTCTC CCCACTTTTG ATTCACTGAA TATTACTGCT GCATCTTTAA
1651 ATGACGATGG ATTGGATAAT CATACTATAC TGCTTTACTA CTCAACTGCT
1701 GCCTCCAGTT TGGCTGTAAC ATTGATGATA GCTATCTTTG TTGTTTATAT
1751 GGTCTCCAGA GACAATGTTT CTTGCTCCAT CTGTCTATAA GGAAAGTTAA
1801 ACCCTGTATT TTCCTTTATT GTAGTGCTTG TTTGCTTGTT ACCATTACAA
1851 AAAACGTTAT TGAAAAATGC TCTTGTTACT ACT
```

SEQ ID NO:22- Amino Acid Sequence of B_Malaysia_2506_04_HA (585 aa)

```
   1 MKAIIVLLMV VTSNADRICT GITSSNSPHV VKTATQGEVN VTGVIPLTTT
  51 PTKSHFANLK GTETRGKLCP KCLNCTDLDV ALGRPKCTGN IPSARVSILH
 101 EVRPVTSGCF PIMHDRTKIR QLPNLLRGYE HIRLSTHNVI NAENAPGGPY
 151 KIGTSGSCPN VTNGNGFFAT MAWAVPKNDN NKTATNSLTI EVPYICTEGE
 201 DQITVWGFHS DSETQMAKLY GDSKPQKFTS SANGVTTHYV SQIGGFPNQT
 251 EDGGLPQSGR IVVDYMVQKS GKTGTITYQR GILLPQKVWC ASGRSKVIKG
 301 SLPLIGEADC LHEKYGGLNK SKPYYTGEHA KAIGNCPIWV KTPLKLANGT
 351 KYRPPAKLLK ERGFFGAIAG FLEGGWEGMI AGWHGYTSHG AHGVAVAADL
 401 KSTQEAINKI TKNLNSLSEL EVKNLQRLSG AMDELHNEIL ELDEKVDDLR
 451 ADTISSQIEL AVLLSNEGII NSEDEHLLAL ERKLKKMLGP SAVEIGNGCF
 501 ETKHKCNQTC LDRIAAGTFD AGEFSLPTFD SLNITAASLN DDGLDNHTIL
 551 LYYSTAASSL AVTLMIAIFV VYMVSRDNVS CSICL
```

Figure 1K

SEQ ID NO:23- Nucleotide Sequence of ca B_Malaysia_2506_04_NA
Entire molecule length: 1536 bp

```
   1 AGCAGAAGCA GAGCATCTTC TCAAAACTGA AGCAAATAGG CCAAAAATGA
  51 ACAATGCTAC CTTCAACTAT ACAAACGTTA ACCCTATTTC TCACATCAGG
 101 GGGAGTATTA TTATCACTAT ATGTGTCAGC TTCATTGTCA TACTTACTAT
 151 ATTCGGATAT ATTGCTAAAA TTCCCATCAA CAGAAATTAC TGCACCAACA
 201 ATGCCATTGG ATTGTGCAAA CGCATCAAAT GTTCAGGCTG TGAACCGTTC
 251 TGCAACAAAA GGGGTGACAC TTCTTCTCCC AGAACCGGAG TGGACATACC
 301 CGCGTTTATC TTGCCCGGGC TCAACCTTTC AGAAAGCACT CCTAATTAGC
 351 CCTCATAGAT TCGGAGAAAC CAAAGGAAAC TCAGCTCCCT TGATAATAAG
 401 GGAACCTTTT ATTGCTTGTG GACCAAAGGA ATGCAAACAC TTTGCTCTAA
 451 CCCACTATGC AGCCCAACCA GGGGGATACT ACAATGGAAC AAGAGGAGAC
 501 AGAAACAAGC TGAGGCATCT AATTTCAGTC AAATTGGGCA AAATCCCAAC
 551 AGTAGAAAAC TCCATTTTCC ACATGGCAGC ATGGAGCGGG TCCGCATGCC
 601 ATGATGGTAA GGAATGGACA TATATCGGAG TTGATGGCCC TGACAATAAT
 651 GCATTGCTCA AAATAAAATA TGGAGAAGCA TATACTGACA CATACCATTC
 701 CTATGCAAAC AACATCCTAA GAACACAAGA AAGTGCCTGC AATTGCATCG
 751 GGGGAAATTG TTATCTTATG ATAACTGATG GCTCAGCTTC AGGTGTTAGT
 801 GAATGCAGAT TTCTTAAGAT TCGAGAGGGC CGAATAATAA AGAAATATT
 851 TCCAACAGGA AGAATAAAAC ATACTGAAGA ATGCACATGC GGATTTGCTA
 901 GCAATAAAAC CATAGAATGT GCCTGTAGAG ATAACAGTTA CACAGCAAAA
 951 AGACCCTTTG TCAAATTAAA CGTGGAGACT GATACAGCAG AAATAAGATT
1001 GATGTGCACA GAGACTTATT GGACACCCCA GACCAGAT GATGGAAGCA
1051 TAACAGGGCC TTGTGAATCT AATGGGGACA AGGGAGTGG AGGCATCAAG
1101 GGAGGATTTG TCCATCAAAG AATGGCATCC AAGATTGGAA GGTGGTACTC
1151 TCGAACGATG TCTAAAACTA AAAGGATGGG GATGGGGCTG TATGTCAAGT
1201 ATGATGGAGA CCCATGGGCT GACAGTGATG CCCTTGCTTT TAGTGGAGTA
1251 ATGGTTTCAA TGGAAGAACC TGGTTGGTAC TCCTTTGGCT TCGAAATAAA
1301 AGACAAGAAA TGTGATGTCC CCTGTATTGG GATAGAGATG GTACATGATG
1351 GTGGAAAAGA GACTTGGCAC TCAGCAGCTA CAGCCATTTA CTGTTTAATG
1401 GGCTCAGGAC AGCTGCTGTG GGACACTGTC ACAGGTGTTA ATATGGCTCT
1451 GTAATGGAGG AATGGTTGAG TCTGTTCTAA ACCCTTTGTT CCTATTTTGT
1501 TTGAACAATT GTCCTTACTG AACTTAATTG TTTCTG
```

SEQ ID NO:24- Amino Acid Sequence of ca B_Malaysia_2506_04_NA
Entire molecule length: 466 aa

```
   1 MLPSTIQTLT LFLTSGGVLL SLYVSASLSY LLYSDILLKF PSTEITAPTM
  51 PLDCANASNV QAVNRSATKG VTLLLPEPEW TYPRLSCPGS TFQKALLISP
 101 HRFGETKGNS APLIIREPFI ACGPKECKHF ALTHYAAQPG GYYNGTRGDR
 151 NKLRHLISVK LGKIPTVENS IFHMAAWSGS ACHDGKEWTY IGVDGPDNNA
 201 LLKIKYGEAY TDTYHSYANN ILRTQESACN CIGGNCYLMI TDGSASGVSE
 251 CRFLKIREGR IIKEIFPTGR IKHTEECTCG FASNKTIECA CRDNSYTAKR
 301 PFVKLNVETD TAEIRLMCTE TYLDTPRPDD GSITGPCESN GDKGSGGIKG
 351 GFVHQRMASK IGRWYSRTMS KTKRMGMGLY VKYDGDPWAD SDALAFSGVM
 401 VSMEEPGWYS FGFEIKDKKC DVPCIGIEMV HDGGKETWHS AATAIYCLMG
 451 SGQLLWDTVT GVNMAL
```

Figure 1L

SEQ ID NO:25- Nucleotide Sequence of ca_B_Brisbane_60_2008_DET_HA
Entire molecule length: 1881 bp

```
   1 gaagcagagc attttctaat atccacaaaa tgaaggcaat aattgtacta
  51 ctcatggtag taacatccaa tgcagatcga atctgcactg ggataacatc
 101 gtcaaactca ccacatgtcg tcaaaactgc tactcaaggg gaggtcaatg
 151 tgactggtgt aataccactg acaacaacac ccaccaaatc tcattttgca
 201 aatctcaaag gaacagaaac caggggggaaa ctatgcccaa aatgcctcaa
 251 ctgcacagat ctggacgtag ccttgggcag accaaaatgc acggggaaaa
 301 taccctcggc aagagtttca atactccatg aagtcagacc tgttacatct
 351 gggtgctttc ctataatgca cgacagaaca aaaattagac agctgcctaa
 401 ccttctccga ggatacgaac atatcaggtt atcaacccat aacgttatca
 451 atgcagaaaa tgcaccagga ggaccctaca aaattggaac ctcagggtct
 501 tgccctaaca ttaccaatgg aaacggattt ttcgcaacaa tggcttgggc
 551 cgtcccaaaa aacgacaaaa acaaaacagc aacaaatcca ttaacaatag
 601 aagtaccata catttgtaca gaaggagaag accaaattac cgtttggggg
 651 ttccactctg acgacgagac ccaaatggca aagctctatg ggactcaaa
 701 gccccagaag ttcacctcat ctgccaacgg agtgaccaca cattacgttt
 751 cacagattgg tggcttccca aatcaaacag aagacggagg actaccacaa
 801 agtggtagaa ttgttgttga ttacatggtg caaaaatctg ggaaaacagg
 851 aacaattacc tatcaaaggg gtattttatt gcctcaaaag gtgtggtgcg
 901 caagtggcag gagcaaggta ataaaaggat ccttgccttt aattggagaa
 951 gcagattgcc tccacgaaaa atacggtgga ttaaacaaaa gcaagcctta
1001 ctacacaggg gaacatgcaa aggccatagg aaattgccca atatgggtga
1051 aaacacccctt gaagctggcc aatggaacca aatatagacc tcctgcaaaa
1101 ctattaaagg aaaggggttt cttcggagct attgctggtt tcttagaagg
1151 aggatgggaa ggaatgattg caggttggca cggatacaca tcccatgggg
1201 cacatggagt agcggtggca gcagacctta agagcactca agaggccata
1251 aacaagataa caaaaaatct caactctttg agtgagctgg aagtaaagaa
1301 tcttcaaaga ctaagcggtg ccatggatga actccacaac gaaatactag
1351 aactagatga gaaagtggat gatctcagag ctgatacaat aagctcacaa
1401 atagaactcg cagtcctgct ttccaatgaa ggaataataa acagtgaaga
1451 tgaacatctc ttggcgcttg aaagaaagct gaagaaaatg ctgggcccct
1501 ctgctgtaga gatagggaat ggatgctttg aaaccaaaca caagtgcaac
1551 cagacctgtc tcgacagaat agctgctggt acctttgatg caggagaatt
1601 ttctctcccc acctttgatt cactgaatat tactgctgca tctttaaatg
1651 acgatggatt ggataatcat actatactgc tttactactc aactgctgcc
1701 tccagtttgg ctgtaacact gatgatagct atctttgttg tttatatggt
1751 ctccagagac aatgtttctt gctccatctg tctataaggg aagttaagcc
1801 ctgtattttc ctttattgta gtgcttgttt acttgttgtc attacaaaga
1851 aacgttattg aaaaatgctc ttgttactac t
```

SEQ ID NO:26- Amino Acid Sequence of ca_B_Brisbane_60_2008_DET_HA
Entire molecule length: 585 aa

```
  1 MKAIIVLLMV VTSNADRICT GITSSNSPHV VKTATQGEVN VTGVIPLTTT
 51 PTKSHFANLK GTETRGKLCP KCLNCTDLDV ALGRPKCTGK IPSARVSILH
101 EVRPVTSGCF PIMHDRTKIR QLPNLLRGYE HIRLSTHNVI NAENAPGGPY
151 KIGTSGSCPN ITNGNGFFAT MAWAVPKNDK NKTATNPLTI EVPYICTEGE
201 DQITVWGFHS DDETQMAKLY GDSKPQKFTS SANGVTTHYV SQIGGFPNQT
251 EDGGLPQSGR IVVDYMVQKS GKTGTITYQR GILLPQKVWC ASGRSKVIKG
301 SLPLIGEADC LHEKYGGLNK SKPYYTGEHA KAIGNCPIWV KTPLKLANGT
351 KYRPPAKLLK ERGFFGAIAG FLEGGWEGMI AGWHGYTSHG AHGVAVAADL
401 KSTQEAINKI TKNLNSLSEL EVKNLQRLSG AMDELHNEIL ELDEKVDDLR
451 ADTISSQIEL AVLLSNEGII NSEDEHLLAL ERKLKKMLGP SAVEIGNGCF
501 ETKHKCNQTC LDRIAAGTFD AGEFSLPTFD SLNITAASLN DDGLDNHTIL
551 LYYSTAASSL AVTLMIAIFV VYMVSRDNVS CSICL
```

Figure 1M

SEQ ID NO:27- Nucleotide Sequence of ca_B_Brisbane_60_2008_DET_NA
Entire molecule length: 1557 bp

```
   1 agcagaagca gagcatcttc tcaaaactga agcaaatagg ccaaaaatga
  51 acaatgctac cttcaactat acaaacgtta accctatttc tcacatcagg
 101 gggagtatta ttatcactat atgtgtcagc ttcattatca tacttactat
 151 attcggatat attgctaaaa ttctcaccaa cagaaataac tgcaccaaca
 201 atgccattgg attgtgcaaa cgcatcaaat gttcaggctg tgaaccgttc
 251 tgcaacaaaa ggggtgacac ttcttctccc agaaccggag tggacatacc
 301 cgcgtttatc ttgcccgggc tcaacctttc agaaagcact cctaattagc
 351 cctcatagat cggagaaaac caaggaaac tcagctccct tgataataag
 401 ggaacctttt attgcttgtg gaccaaatga atgcaaacac tttgctctaa
 451 cccattatgc agcccaacca ggggatact acaatggaac aagaggagac
 501 agaaacaagc tgaggcatct aatttcagtc aaattgggca aatcccaac
 551 agtagaaaac tccattttcc acatggcagc atggagcggg tccgcgtgcc
 601 atgatggtaa ggaatggaca tatatcggag ttgatggccc tgacaataat
 651 gcattgctca agtaaaata tggagaagca tatactgaca cataccattc
 701 ctatgcaaac aaaatcctaa gaacacaaga aagtgcctgc aattgcatcg
 751 ggggaaattg ttatcttatg ataactgatg gctcagcttc aggtgttagt
 801 gaatgcagat ttcttaagat tcgagagggc cgaataataa agaaatatt
 851 tccaacagga gagtaaaac acactgagga atgcacatgc ggatttgcca
 901 gcaataaaac catagaatgt gcctgtagag ataacagtta cacagcaaaa
 951 agaccttttg tcaaattaaa cgtggagact gatacagcag aaataagatt
1001 gatgtgcaca gatacttatt tggacacccc cagaccaaac gatggaagca
1051 taacaggccc ttgtgaatct aatggggaca agggagtgg aggcatcaag
1101 ggaggatttg ttcatcaaag aatggaatcc aagattggaa ggtggtactc
1151 tcgaacgatg tctaaaactg aaggatggg gatgggactg tatgtcaagt
1201 atgatggaga cccatggct gacagtgatg ccctagcttt tagtggagta
1251 atggtttcaa tgaaagaacc tggttggtac tcctttggct cgaaataaa
1301 agataagaaa tgcgatgtcc cctgtattgg gatagagatg gtacatgatg
1351 gtggaaaaga gacttggcac tcagcagcaa cagccattta ctgtttaatg
1401 ggctcaggac agctgctgtg ggacactgtc acaggtgttg acatggctct
1451 gtaatggagg aatggttgag tctgttctaa acccttttgtt cctgttttgt
1501 ttgaacaatt gtccttacta aacttaattg tttctgaaaa atgctcttgt
1551 tactact
```

SEQ ID NO:28- Amino Acid Sequence of ca_B_Brisbane_60_2008_DET_NA
Entire molecule length: 466 aa

```
   1 MLPSTIQTLT LFLTSGGVLL SLYVSASLSY LLYSDILLKF SPTEITAPTM
  51 PLDCANASNV QAVNRSATKG VTLLLPEPEW TYPRLSCPGS TFQKALLISP
 101 HRFGETKGNS APLIIREPFI ACGPNECKHF ALTHYAAQPG GYYNGTRGDR
 151 NKLRHLISVK LGKIPTVENS IFHMAAWSGS ACHDGKEWTY IGVDGPDNNA
 201 LLKVKYGEAY TDTYHSYANK ILRTQESACN CIGGNCYLMI TDGSASGVSE
 251 CRFLKIREGR IIKEIFPTGR VKHTEECTCG FASNKTIECA CRDNSYTAKR
 301 PFVKLNVETD TAEIRLMCTD TYLDTPRPND GSITGPCESN GDKGSGGIKG
 351 GFVHQRMESK IGRWYSRTMS KTERMGMGLY VKYDGDPWAD SDALAFSGVM
 401 VSMKEPGWYS FGFEIKDKKC DVPCIGIEMV HDGGKETWHS AATAIYCLMG
 451 SGQLLWDTVT GVDMAL
```

Figure 1N

| SEQ ID NO | HA or NA | Strain Name |
|---|---|---|
| SEQ ID NO:1 and 2 | HA | ca A/Uruguay/716/07 |
| SEQ ID NO:3 and 4 | NA | ca A/Uruguay/716/07 |
| SEQ ID NO:5 and 6 | HA | ca A/South Dakota/6/07 |
| SEQ ID NO:7 and 8 | NA | ca A/South Dakota/6/07 |
| SEQ ID NO:9 and 10 | HA | ca B/Florida/6/04 |
| SEQ ID NO:11 and 12 | NA | ca B/Florida/6/04 |
| SEQ ID NO:13 and 14 | HA | ca A/Wisconsin/67/05 |
| SEQ ID NO:15 and 16 | NA | ca A/Wisconsin/67/05 |
| SEQ ID NO:17 and 18 | HA | ca A/Solomon Islands/3/06 |
| SEQ ID NO:19 and 20 | NA | ca A/Solomon Islands/3/06 |
| SEQ ID NO:21 and 22 | HA | ca B/Malaysia/2506/04 |
| SEQ ID NO:23 and 24 | NA | ca B/Malaysia/2506/04 |
| SEQ ID NO:25 and 26 | HA | ca B/Brisbane/60/2008_DET |
| SEQ ID NO:27 and 28 | NA | ca B/Brisbane/60/2008_DET |

Figure 2

SEQUENCE LISTING

<160> NUMBER OF SEQ ID NOS: 29

<210> SEQ ID NO 1
<211> LENGTH: 1757
<212> TYPE: DNA
<213> ORGANISM: Influenza A virus

<400> SEQUENCE: 1

```
aaagcagggg ataattctat taaccatgaa gactatcatt gctttgagct acattctatg      60
tctggttttc gctcaaaaac ttcctggaaa tgacaacagc acggcaacgc tgtgccttgg     120
gcaccatgca gtaccaaacg gaacgatagt gaaaacaatc acgaatgacc aaattgaagt     180
tactaatgct actgagctgg ttcagagttc ctcaacaggt gaaatatgcg acagtcctca     240
tcagatcctt gatggagaaa actgcacact aatagatgct ctattgggag accctcagtg     300
tgatggcttc caaaataaga aatgggacct ttttgttgaa cgcagcaaag cctacagcaa     360
ctgttaccct tatgatgtgc cggattatgc ctcccttagg tcactagttg cctcatccgg     420
cacactggag tttaacaatg aaagcttcaa ttggactgga gtcactcaaa acggaacaag     480
ctcttcttgc ataaggagat ctaataacag tttctttagt agattgaatt ggttgaccca     540
cttaaaattc aaatacccag cattgaacgt gactatgcca aacaatgaaa aatttgacaa     600
attgtacatt tgggggggttc accacccggg tacgacaat gaccaaatct tcccgtatgc      660
tcaagcatca ggaagaatca cagtctctac caaaagaagc caacaaactg taatcccgaa     720
tatcggatct agacccagag taaggaatat ccccagcaga ataagcatct attggacaat     780
agtaaaaccg ggagacatac ttttgattaa cagcacaggg aatctaattg ctcctagggg     840
ttacttcaaa atacgaagtg ggaaaagctc aataatgaga tcagatgcac ccattggcaa     900
atgcaattct gaatgcatca ctccaaatgg gagcattccc aatgacaaac cattccaaaa     960
tgtaaacagg atcacatacg gggcctgtcc cagatatgtt aagcaaaaca ctctgaaatt    1020
ggcaacaggg atgcgaaatg taccagagaa acaaactaga ggcatatttg gcgcaatcgc    1080
gggtttcata gaaaatggtt gggagggaat ggtggatggt tggtacggtt tcaggcatca    1140
aaattctgag gaataggac aagcagcaga tctcaaaagc actcaagcag caatcgatca    1200
aatcaatggg aagctgaata ggttgatcgg gaaaccaac gagaaattcc atcagattga    1260
aaaggaattc tcagaagtcg aagggaggat tcaggacctt gagaaatatg ttgaggacac    1320
caaaatagat ctctggtcat acaacgcgga gcttcttgtt gccctggaga accaacatac    1380
aattgatcta actgactcag aaatgaacaa actgtttgaa aaacaaaga agcaactgag    1440
ggaaaatgct gaggatatgg gcaatggttg tttcaaaata taccacaaat gtgacaatgc    1500
ctgcatagga tcaatcagaa atggaactta tgaccacgat gtatacagag atgaagcatt    1560
aaacaaccgg ttccagatca agggcgttga gctgaagtca ggatacaaag attggatcct    1620
atggatttcc tttgccatat catgtttttt gctttgtgtt gctttgttgg ggttcatcat    1680
gtgggcctgc caaaaaggca acattaggtg caacatttgc atttgagtgc attaattaaa    1740
```

-continued aacacccttg tttctac 1757

<210> SEQ ID NO 2
<211> LENGTH: 566
<212> TYPE: PRT
<213> ORGANISM: Influenza A virus

<400> SEQUENCE: 2

| | | | | | | | | | | | | | | | |
|---|---|---|---|---|---|---|---|---|---|---|---|---|---|---|---|
| Met | Lys | Thr | Ile | Ile | Ala | Leu | Ser | Tyr | Ile | Leu | Cys | Leu | Val | Phe | Ala |
| 1 | | | | 5 | | | | | 10 | | | | | 15 | |
| Gln | Lys | Leu | Pro | Gly | Asn | Asp | Asn | Ser | Thr | Ala | Thr | Leu | Cys | Leu | Gly |
| | | | 20 | | | | | 25 | | | | | 30 | | |
| His | His | Ala | Val | Pro | Asn | Gly | Thr | Ile | Val | Lys | Thr | Ile | Thr | Asn | Asp |
| | | 35 | | | | | 40 | | | | | 45 | | | |
| Gln | Ile | Glu | Val | Thr | Asn | Ala | Thr | Glu | Leu | Val | Gln | Ser | Ser | Ser | Thr |
| | 50 | | | | | 55 | | | | | 60 | | | | |
| Gly | Glu | Ile | Cys | Asp | Ser | Pro | His | Gln | Ile | Leu | Asp | Gly | Glu | Asn | Cys |
| 65 | | | | | 70 | | | | | 75 | | | | | 80 |
| Thr | Leu | Ile | Asp | Ala | Leu | Leu | Gly | Asp | Pro | Gln | Cys | Asp | Gly | Phe | Gln |
| | | | | 85 | | | | | 90 | | | | | 95 | |
| Asn | Lys | Lys | Trp | Asp | Leu | Phe | Val | Glu | Arg | Ser | Lys | Ala | Tyr | Ser | Asn |
| | | | 100 | | | | | 105 | | | | | 110 | | |
| Cys | Tyr | Pro | Tyr | Asp | Val | Pro | Asp | Tyr | Ala | Ser | Leu | Arg | Ser | Leu | Val |
| | | 115 | | | | | 120 | | | | | 125 | | | |
| Ala | Ser | Ser | Gly | Thr | Leu | Glu | Phe | Asn | Asn | Glu | Ser | Phe | Asn | Trp | Thr |
| | 130 | | | | | 135 | | | | | 140 | | | | |
| Gly | Val | Thr | Gln | Asn | Gly | Thr | Ser | Ser | Ser | Cys | Ile | Arg | Arg | Ser | Asn |
| 145 | | | | | 150 | | | | | 155 | | | | | 160 |
| Asn | Ser | Phe | Phe | Ser | Arg | Leu | Asn | Trp | Leu | Thr | His | Leu | Lys | Phe | Lys |
| | | | | 165 | | | | | 170 | | | | | 175 | |
| Tyr | Pro | Ala | Leu | Asn | Val | Thr | Met | Pro | Asn | Asn | Glu | Lys | Phe | Asp | Lys |
| | | | 180 | | | | | 185 | | | | | 190 | | |
| Leu | Tyr | Ile | Trp | Gly | Val | His | His | Pro | Gly | Thr | Asp | Asn | Asp | Gln | Ile |
| | | 195 | | | | | 200 | | | | | 205 | | | |
| Phe | Pro | Tyr | Ala | Gln | Ala | Ser | Gly | Arg | Ile | Thr | Val | Ser | Thr | Lys | Arg |
| | 210 | | | | | 215 | | | | | 220 | | | | |
| Ser | Gln | Gln | Thr | Val | Ile | Pro | Asn | Ile | Gly | Ser | Arg | Pro | Arg | Val | Arg |
| 225 | | | | | 230 | | | | | 235 | | | | | 240 |
| Asn | Ile | Pro | Ser | Arg | Ile | Ser | Ile | Tyr | Trp | Thr | Ile | Val | Lys | Pro | Gly |
| | | | | 245 | | | | | 250 | | | | | 255 | |
| Asp | Ile | Leu | Leu | Ile | Asn | Ser | Thr | Gly | Asn | Leu | Ile | Ala | Pro | Arg | Gly |
| | | | 260 | | | | | 265 | | | | | 270 | | |
| Tyr | Phe | Lys | Ile | Arg | Ser | Gly | Lys | Ser | Ser | Ile | Met | Arg | Ser | Asp | Ala |
| | | 275 | | | | | 280 | | | | | 285 | | | |
| Pro | Ile | Gly | Lys | Cys | Asn | Ser | Glu | Cys | Ile | Thr | Pro | Asn | Gly | Ser | Ile |
| | 290 | | | | | 295 | | | | | 300 | | | | |
| Pro | Asn | Asp | Lys | Pro | Phe | Gln | Asn | Val | Asn | Arg | Ile | Thr | Tyr | Gly | Ala |
| 305 | | | | | 310 | | | | | 315 | | | | | 320 |
| Cys | Pro | Arg | Tyr | Val | Lys | Gln | Asn | Thr | Leu | Lys | Leu | Ala | Thr | Gly | Met |
| | | | | 325 | | | | | 330 | | | | | 335 | |
| Arg | Asn | Val | Pro | Glu | Lys | Gln | Thr | Arg | Gly | Ile | Phe | Gly | Ala | Ile | Ala |
| | | | 340 | | | | | 345 | | | | | 350 | | |
| Gly | Phe | Ile | Glu | Asn | Gly | Trp | Glu | Gly | Met | Val | Asp | Gly | Trp | Tyr | Gly |
| | | 355 | | | | | 360 | | | | | 365 | | | |
| Phe | Arg | His | Gln | Asn | Ser | Glu | Gly | Ile | Gly | Gln | Ala | Ala | Asp | Leu | Lys |

|       |       |       |       | 370   |       |       |       |       | 375   |       |       |       |       | 380   |       |       |
Ser Thr Gln Ala Ala Ile Asp Gln Ile Asn Gly Lys Leu Asn Arg Leu
385                     390                     395                     400

Ile Gly Lys Thr Asn Glu Lys Phe His Gln Ile Glu Lys Glu Phe Ser
            405                     410                     415

Glu Val Glu Gly Arg Ile Gln Asp Leu Glu Lys Tyr Val Glu Asp Thr
                420                     425                     430

Lys Ile Asp Leu Trp Ser Tyr Asn Ala Glu Leu Leu Val Ala Leu Glu
            435                     440                     445

Asn Gln His Thr Ile Asp Leu Thr Asp Ser Glu Met Asn Lys Leu Phe
450                     455                     460

Glu Lys Thr Lys Lys Gln Leu Arg Glu Asn Ala Glu Asp Met Gly Asn
465                     470                     475                     480

Gly Cys Phe Lys Ile Tyr His Lys Cys Asp Asn Ala Cys Ile Gly Ser
                485                     490                     495

Ile Arg Asn Gly Thr Tyr Asp His Asp Val Tyr Arg Asp Glu Ala Leu
            500                     505                     510

Asn Asn Arg Phe Gln Ile Lys Gly Val Glu Leu Lys Ser Gly Tyr Lys
            515                     520                     525

Asp Trp Ile Leu Trp Ile Ser Phe Ala Ile Ser Cys Phe Leu Leu Cys
530                     535                     540

Val Ala Leu Leu Gly Phe Ile Met Trp Ala Cys Gln Lys Gly Asn Ile
545                     550                     555                     560

Arg Cys Asn Ile Cys Ile
            565

<210> SEQ ID NO 3
<211> LENGTH: 1458
<212> TYPE: DNA
<213> ORGANISM: Influenza A virus

<400> SEQUENCE: 3
gcaaaagcag gagtaaagat gaatccaaat caaaagataa taacgattgg ctctgtttct    60
ctcaccattt ccacaatatg cttcttcatg caaactgcca tcttgataac tactgtaaca   120
ttgcatttca agcaatatga attcaactcc cccccaaaca accaagtgat gctgtgtgaa   180
ccaacaataa tagaaagaaa cataacagag atagtgtatc tgaccaacac caccatagag   240
aaggaaatat gccccaaact agcagaatac agaaaattgg caaagccgca atgtgacatt   300
acaggatttg caccttttttc taaggacaat tcgattaggc tttccgctgg tgggacatc   360
tgggtgacaa gagaaccttt atgtgtcatg cgatcctgaca agtgttatca atttgccctt   420
ggacagggaa caacactaaa caacgtgcat tcaaatgaca cagtacatga taggaccccct   480
tatcggaccc tattgatgaa tgagttaggt gttccttttc atctggggac caagcaagtg   540
tgcatagcat ggtccagctc aagttgtcac gatggaaaag catggctgca tgtttgtata   600
acggggggatg ataaaatgc aactgctagc ttcatttaca tgggaggct gtagatagt   660
attgttcat ggtccaaaga atcctcagg acccaggagt cagaatgcgt ttgtatcaat   720
ggaacttgta cagtagtaat gactgatggg agtgcttcag gaaaagctga tactaaaata   780
ctattcattg aggaggggaa aatcgttcat actagcatat tgtcaggaag tgctcagcat   840
gtcgaggagt gctcctgcta tcctcgatat cctggtgtca gatgtgtctg cagagacaac   900
tggaaaggct ccaataggcc catcgtagat ataacataa aggatcatag cattgttttcc   960
agttatgtgt gttcaggact tgttggagac acacccagaa aaaacgacag ctccagcagt   1020

-continued

```
agccattgtt tggatcctaa caatgaagaa ggtggtcatg gagtgaaagg ctgggccttt    1080
gatgatggaa atgacgtgtg gatgggaaga acgatcagcg agaagtcacg cttagggtat    1140
gaaaccttca aagtcattga aggctggtcc aaccctaagt ccaaattgca gataaatagg    1200
caagtcatag ttgacagagg taataggtcc ggttattctg gtattttctc tgttgaaggc    1260
aaaagctgca tcaatcggtg cttttatgtg gagttgataa ggggaagaaa agaggaaact    1320
gaagtcttgt ggacctcaaa cagtattgtt gtgttttgtg gcacctcagg tacatatgga    1380
acaggctcat ggcctgatgg ggcggacatc aatctcatgc ctatataagc tttcgcaatt    1440
ttagaaaaaa actccttg                                                  1458
```

<210> SEQ ID NO 4
<211> LENGTH: 469
<212> TYPE: PRT
<213> ORGANISM: Influenza A virus

<400> SEQUENCE: 4

```
Met Asn Pro Asn Gln Lys Ile Ile Thr Ile Gly Ser Val Ser Leu Thr
1               5                   10                  15

Ile Ser Thr Ile Cys Phe Phe Met Gln Thr Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Ile Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300
```

```
Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser His
            325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Ser Arg Leu Gly Tyr Glu Thr Phe Lys Val Ile Glu Gly Trp Ser
370                 375                 380

Asn Pro Lys Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 5
<211> LENGTH: 1771
<212> TYPE: DNA
<213> ORGANISM: Influenza A virus

<400> SEQUENCE: 5
aaaagcaggg gaaataaaa acaaccagaa tgaaagtaaa actactggtc ctgttatgca      60
catttacagc tacatatgca gacacaatat gtataggcta ccatgctaac aactcgaccg     120
acactgttga cacagtactt gaaaagaatg tgacagtgac acactctgtc aacctgcttg     180
agaacagtca aatggaaga ctatgtctat taaaggaat agccccacta caattgggta      240
actgcagcgt tgccgggtgg atcttaggaa acccagaatg cgaattactg atttccaagg     300
agtcatggtc ctacattgta gaaaaaccaa atcctgagaa tggaacatgt tacccagggc     360
atttcgctga ctatgaggaa ctgagggagc aattgagttc agtatcttca cttgagaggt     420
tcgaaatatt ccccaaagaa agctcatggc ccaaccacac cgtaaccgga gtgtcagcat     480
catgctccca taatgggaa agcagttttt acagaaattt gctatggctg acggggaaga    540
atggtttgta cccaaacctg agcaagtcct atgcaaacaa caagaaaaa gaagtccttg    600 tactatgggg tgttcatcac ccgccaaaca taggtaacca aaaggccctc tatcatacag    660
aaaatgctta tgtttctgta gtgtcttcac attatagcag aaaattcacc ccagaaatag    720
ccaaaagacc caagtaaga gatcaagaag gaagaatcaa ctactactgg actctgcttg    780
aacccgggga tacaataata tttgaggcaa atggaaatct aatagcgcca agatatgctt    840
tcgcactgag tagaggcttt ggatcaggaa tcatcaactc aaatgcacca atggataaat    900
gtgatgcgaa gtgccaaaca cctcagggag ctataaacag cagtcttcct ttccagaacg    960
tacacccagt cacaatagga gagtgtccaa agtatgtcag gagtgcaaaa ttaaggatgg   1020
ttacaggact aaggaacatc ccatccattc aatccgagg tttgtttgga gccattgccg   1080
gtttcattga aggggggtgg actggaatgg tagatggttg gtatggttat catcatcaga   1140
```

```
atgagcaagg atctggctat gctgcagatc aaaaaagcac acaaaatgcc attaatggga   1200
ttacaaacaa ggtgaattct gtaattgaga aaatgaacac tcaattcaca gcagtgggca   1260
aagaattcaa caaattggaa agaaggatgg aaaacttgaa taaaaaagtt gatgatggt   1320 ttatagacat ttggacatat aatgcagaac tgttggttct actggaaaat gaaaggactt   1380
tggatttcca tgactccaat gtgaagaatc tgtatgagaa agtaaaaagc cagttaaaga   1440
ataatgctaa agaatagga aatgggtgtt ttgaattcta tcacaagtgt aacgatgaat   1500
gcatggagag tgtaaagaat ggaacttatg actatccaaa atattccgaa gaatcaaagt   1560
taaacaggga gaaaattgat ggagtgaaat tggaatcaat gggagtctat cagattctgg   1620
cgatctactc aacagtcgcc agttctctgg ttcttttggt ctccctgggg gcaatcagct   1680
tctggatgtg ttccaatggg tctttgcagt gtagaatatg catctaagac cagaatttca   1740
gaaatataag gaaaaacacc cttgtttcta c                                 1771
```

<210> SEQ ID NO 6
<211> LENGTH: 565
<212> TYPE: PRT
<213> ORGANISM: Influenza A virus

<400> SEQUENCE: 6

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Arg Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asn Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270
```

Leu Ser Arg Gly Phe Gly Ser Gly Ile Ile Asn Ser Asn Ala Pro Met
            275                 280                 285

Asp Lys Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 7
<211> LENGTH: 1446
<212> TYPE: DNA
<213> ORGANISM: Influenza A virus

<400> SEQUENCE: 7
agcaaaagca ggagtttaaa atgaacccaa atcaaaagat aataaccatt ggatcaatca      60
gtatagcaat cggaataatt agtctaatgt tgcaaatagg aaatattatt tcaatatggg     120
ctagtcactc aatccaaact ggaagtcaaa acaacactgg aatatgcaac caaagaatca     180
tcacatatga aaacagcacc tgggtgaatc acacatatgt taatattaac aacactaatg     240
ttgttgctgg agaggacaaa acttcagtga cattggccgg caattcatct ctttgttcta     300
tcagtggatg ggctatatac acaaaagaca cagcataag aattggctcc aaaggagatg     360 ttttttgtcat aagagaacct ttcatatcat gttctcactt ggaatgcaga accttttttc     420

-continued

```
tgacccaagg cgctctatta aatgacaaac attcaaatgg gaccgtaaag gacagaagtc    480
cttatagggc cttaatgagc tgtcctctag gtgaagctcc gtccccatac aattcaaagt    540
tcgaatcagt tgcatggtca gcaagcgcat gccatgatgg catgggctgg ttaacaatcg    600
gaatttctgg tccagacaat ggagctgtgg ctgtactaaa atacaacgga ataataactg    660
gaaccataaa aagttggaaa aagcaaatat taagaacaca agagtctgaa tgtgtctgta    720
tgaacgggtc atgtttcacc ataatgaccg atggcccgag taataaggcc gcctcgtaca    780
aaattttcaa gatcgaaaag gggaaggtta ctaaatcaat agagttgaat gcacccaatt    840
ttcattatga ggaatgctcc tgttacccag acactggcat agtgatgtgt gtatgcaggg    900
acaactggca tggttcaaat cgaccttggg tgtctttcaa tcaaaacttg gattatcaaa    960
taggatacat ctgcagtgga gtgtttggtg acaatccgcg tcccgaagat ggagagggca   1020
gctgcaatcc agtgactgtt gatggagcaa acggagtaaa agggttttca tacaaatatg   1080
ataatggtgt ttggatagga aggaccaaaa gtaacagact tagaaagggg tttgagatga   1140
tttgggatcc taatggatgg acaaataccg acagtgattt ctcagtgaaa caggatgttg   1200
tagcaataac tgattggtca gggtacagcg gaagtttcgt ccaacatcct gagttaacag   1260
gattggactg tataagacct tgcttctggg ttgagttagt cagagggctg cctagagaaa   1320
atacaacaat ctggactagt gggagcagca tttcttttgg tggcgttaat agtgatactg   1380
caaactggtc ttggccagac ggtgctgagt tgccgttcac cattgacaag tagttcgttg   1440
aaaaaa                                                              1446
```

<210> SEQ ID NO 8
<211> LENGTH: 470
<212> TYPE: PRT
<213> ORGANISM: Influenza A virus

<400> SEQUENCE: 8

```
Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn Asn Thr Gly Ile
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Glu Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190
```

```
Ile Gly Ile Ser Gly Pro Asp Asn Gly Ala Val Ala Val Leu Lys Tyr
        195                 200                 205

Asn Gly Ile Ile Thr Gly Thr Ile Lys Ser Trp Lys Lys Gln Ile Leu
    210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Lys Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Ile Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Glu Asp Gly Glu Gly Ser Cys Asn
                325                 330                 335

Pro Val Thr Val Asp Gly Ala Asn Gly Val Lys Gly Phe Ser Tyr Lys
            340                 345                 350

Tyr Asp Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asn Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470
```

<210> SEQ ID NO 9
<211> LENGTH: 1882
<212> TYPE: DNA
<213> ORGANISM: Influenza B virus

<400> SEQUENCE: 9

```
agcagaagca gagcattttc taatatccac aaaatgaagg caataattgt actactcatg      60
gtagtaacat ccaatgcaga tcgaatctgc actggaataa catcttcaaa ctcacctcat     120
gtggtcaaaa cagccactca aggggaggtc aatgtgactg gtgtgatacc actaacaaca     180
acaccaacaa aatcttattt tgcaaatctc aaaggaacaa ggaccagagg gaaactatgc     240
ccagactgtc tcaactgcac agatctggat gtggctttgg gcagaccaat gtgtgtgggg     300
accacacctt cggcgaaagc ttcaatactc cacgaagtca aacctgttac atccgggtgc     360
tttcctataa tgcacgacag aacaaaaatc aggcaactac ccaatcttct cagaggatat     420
gaaaatatca ggctatcaac ccaaaacgtc atcgatgcgg aaaaggcacc aggaggaccc     480
tacagacttg gaacctcagg atcttgccct aacgctacca gtaagagcgg atttttcgca     540
```

-continued

```
acaatggctt gggctgtccc aaaggacaac aacaaaaatg caacgaaccc actaacagta      600
gaagtaccat acatttgtac agaaggggaa gaccaaatca ctgtttgggg gttccattca      660
gatgacaaaa cccaaatgaa gaacctctat ggagactcaa atcctcaaaa gttcacctca      720
tctgctaatg gagtaaccac acactatgtt tctcagattg gcagcttccc agatcaaaca      780
gaagacggag gactaccaca aagcggcagg attgttgttg attacatgat gcaaaaacct      840
gggaaaacag gaacaattgt ctaccaaaga ggtgttttgt tgcctcaaaa ggtgtggtgc      900
gcgagtggca ggagcaaagt aataaaaggg tccttgcctt taattggtga agcagattgc      960
cttcatgaaa aataccggtgg attaaacaaa agcaagcctt actacacagg agaacatgca     1020
aaagccatag gaaattgccc aatatgggtg aaaacacctt tgaagcttgc caatggaacc     1080
aaatatagac ctcctgcaaa actattaaag gaaaggggtt cttcggagc tattgctggt      1140 ttcctagaag gaggatggga aggaatgatt gcaggctggc acggatacac atctcacgga     1200
gcacatggag tggcagtggc ggcggaccett aagagtacgc aagaagctat aaacaagata     1260
acaaaaaatc tcaattcttt gagtgagcta gaagtaaaga atcttcaaag actaagtggt     1320
gccatggatg aactccacaa cgaaatactc gagctggatg agaaagtgga tgatctcaga     1380
gctgacacta taagctcgca aatagaactt gcagtcttgc tttccaacga aggaataata     1440
aacagtgaag atgagcatct attggcactt gagagaaaac taagaaaat gctgggtccc     1500 tctgctgtag agataggaaa tggatgcttc gaaaccaaac acaagtgcaa ccagacctgc     1560
ttagacagga tagctgctgg caccttataat gcaggagaat tttctctccc cactttttgat     1620 tcactgaaca ttactgctgc atcttaaat gatgatggat tggataacca tactatactg     1680
ctctattact caactgctgc ttctagttg gctgtaacat tgatgctagc tatttttatt     1740 gttatatgg tctccagaga caacgtttca tgctccatct gtctataagg aagattaggc     1800
cttgtatttt cctttattgt agtgcttgtt tgcttgtcat cattacaaag aaacgttatt     1860
gaaaaatgct cttgttacta ct                                              1882
```

<210> SEQ ID NO 10
<211> LENGTH: 584
<212> TYPE: PRT
<213> ORGANISM: Influenza B virus

<400> SEQUENCE: 10

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140
```

-continued

```
Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
```

```
                    565                 570                 575
Asn Val Ser Cys Ser Ile Cys Leu
            580

<210> SEQ ID NO 11
<211> LENGTH: 1557
<212> TYPE: DNA
<213> ORGANISM: Influenza B virus

<400> SEQUENCE: 11
agcagaagca gagcatcttc tcaaaactga ggcaaatagg ccaaaaatga acaatgctac      60
cttcaactat acaaacgtta accctatttc tcacatcagg gggagtgtta ttatcactat     120
atgtgtcagc ttcattgtca tacttactat attcggatat attgctaaaa ttttcacaaa     180
cagaaataac tgcaccaata atgccattgg attgtgcaaa cgcatcaaat gttcaggctg     240
tgaaccgttc tgcagcaaaa ggggtgacac ttcttctccc agaaccggag tggacatacc     300
ctcgtttatc ttgcccgggc tcaacctttc agaaagcact cctaattagc ccccatagat     360
tcggagaaac caaggaaac tcagctccct tgataataag ggaaccttt attgcttgtg      420 gaccaacgga atgcaaacac tttgctctaa cccattatgc agctcaacca ggggatact      480 acaatggaac aagagaagac agaaacaagc tgaggcatct aatttcagtc aaattgggca     540
aaatcccaac agtagaaaac tccatttttcc atatggcagc ttggagcggg tccgcatgcc     600
atgatggtaa agaatggaca tatatcggag ttgatggccc cgacagtaat gcattactca     660
aaataaaata tggagaagca tatactgaca cataccattc ctatgcaaaa aacatcctaa     720
ggacacaaga aagtgcctgc aattgcatcg ggggagattg ttatcttatg ataactgatg     780
gcccagcttc agggattagt gaatgcagat tccttaagat tcgagagggc cgaataataa     840
aagaaatatt tccaacagga agagtaaaaac atactgagga atgcacatgc ggatttgcca     900
gcaacaaaac catagaatgt gcttgtagag ataacagtta cacagcaaaa agacccttttg    960 tcaaattaaa tgtggagact gatacagcgg aaataagatt gatgtgcaca gagacttatt    1020
tggacacccc cagaccaaat gatggaagca taacagggcc ttgcgaatct gatggggaca    1080
aagggagtgg aggcatcaag ggaggatttg ttcatcaaag aatggcatcc aagattggaa    1140
ggtggtactc tcgaacgatg tctaaaacta aagaatggg gatgggactg tatgtaaagt    1200
atgatggaga cccatggact gacagtgaag cccttgctct tagtggagta atggtttcga    1260
tggaagaacc tggttggtat cctttggct tcgaaataaa agataagaaa tgtgatgtcc    1320
cctgtattgg gatagaaatg gtacatgatg gtgggaaaac gacttggcac tcagcagcaa    1380
cagccattta ctgtttaatg ggctcaggac aactgctgtg ggacactgtc acaggtgttg    1440
atatggctct gtaatggagg aatggttgag tctgttctaa acccttttgt cctatttttgt    1500 ttgaacaatt gtccttactg agcttaattg tttctgaaaa atgctcttgt tactact       1557

<210> SEQ ID NO 12
<211> LENGTH: 466
<212> TYPE: PRT
<213> ORGANISM: Influenza B virus

<400> SEQUENCE: 12

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Gln Thr Glu Ile Thr Ala Pro
```

```
                   35                  40                  45
Ile Met Pro Leu Asp Cys Ala Asn Ala Ser Asn Val Gln Ala Val Asn
 50                  55                  60

Arg Ser Ala Ala Lys Gly Val Thr Leu Leu Pro Glu Pro Glu Trp
 65              70                  75                  80

Thr Tyr Pro Arg Leu Ser Cys Pro Gly Ser Thr Phe Gln Lys Ala Leu
                 85                  90                  95

Leu Ile Ser Pro His Arg Phe Gly Thr Lys Gly Asn Ser Ala Pro
                100                 105                 110

Leu Ile Ile Arg Glu Pro Phe Ile Ala Cys Gly Pro Thr Glu Cys Lys
             115                 120                 125

His Phe Ala Leu Thr His Tyr Ala Ala Gln Pro Gly Gly Tyr Tyr Asn
     130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
             180                 185                 190

Val Asp Gly Pro Asp Ser Asn Ala Leu Leu Lys Ile Lys Tyr Gly Glu
     195                 200                 205

Ala Tyr Thr Asp Thr Tyr His Ser Tyr Ala Lys Asn Ile Leu Arg Thr
210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
             245                 250                 255

Arg Glu Gly Arg Ile Ile Lys Glu Ile Phe Pro Thr Gly Arg Val Lys
             260                 265                 270

His Thr Glu Glu Cys Thr Cys Gly Phe Ala Ser Asn Lys Thr Ile Glu
     275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Lys Gly Ser Gly Gly Ile Lys Gly Gly Phe
             340                 345                 350

Val His Gln Arg Met Ala Ser Lys Ile Gly Arg Trp Tyr Ser Arg Thr
     355                 360                 365

Met Ser Lys Thr Lys Arg Met Gly Met Gly Leu Tyr Val Lys Tyr Asp
370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
             420                 425                 430

Gly Gly Lys Thr Thr Trp His Ser Ala Ala Thr Ala Ile Tyr Cys Leu
         435                 440                 445

Met Gly Ser Gly Gln Leu Leu Trp Asp Thr Val Thr Gly Val Asp Met
450                 455                 460
```

Ala Leu
465

<210> SEQ ID NO 13
<211> LENGTH: 1763
<212> TYPE: DNA
<213> ORGANISM: Influenza A virus

<400> SEQUENCE: 13

```
agcaaaagca ggggataatt ctattaacca tgaagactat cattgctttg agctacattc      60
tatgtctggt tttcgctcaa aaacttcccg gaaatgacaa cagcacggca acgctgtgcc     120
ttgggcacca tgcagtacca acggaacga tagtgaaaac aatcacgaat gaccaaattg     180
aagttactaa tgctactgag ctggttcaga gttcctcaac aggtggaata tgcgacagtc     240
ctcatcagat ccttgatgga gaaaactgca cactaataga tgctctattg ggagaccctc     300
agtgtgatgg cttccaaaat aagaaatggg accttttttgt tgaacgcagc aaagcctaca     360
gcaactgtta cccttatgat gtgccggatt atgcctccct taggtcacta gttgcctcat     420
ccggcacact ggagtttaac gatgaaagct tcaattggac tggagtcact caaaatggaa     480
caagctcttc ttgcaaaagg agatctaata acagttctt tagtagattg aattggttga     540
cccacttaaa attcaaatac ccagcattga acgtgactat gccaaacaat gaaaaatttg     600
acaaattgta catttggggg gttcaccacc cggttacgga caatgaccaa atcttcctgt     660
atgctcaagc atcaggaaga atcacagtct ctaccaaaag aagccaacaa actgtaatcc     720
cgaatatcgg atctagaccc agaataagga atatccccag cagaataagc atctattgga     780
caatagtaaa accgggagac atacttttga ttaacagcac agggaatcta attgctccta     840
ggggttactt caaaatacga agtgggaaaa gctcaataat gagatcagat gcacccattg     900
gcaaatgcaa ttctgaatgc atcactccaa atggaagcat tcccaatgac aaaccatttc     960
aaaatgtaaa caggatcaca tatggggcct gtcccagata tgttaagcaa aacactctga    1020
aattggcaac agggatgcga atgtaccag agaaacaaac tagaggcata tttggcgcaa    1080
tcgcgggttt catagaaaat ggttgggagg gaatggtgga tggttggtac ggtttcaggc    1140
atcaaaattc tgagggaata ggacaagcag cagatctcaa aagcactcaa gcagcaatca    1200
atcaaatcaa tgggaagctg aataggttga tcgggaaaac caacgagaaa ttccatcaga    1260
ttgaaaaaga attctcagaa gtagaaggga gaattcagga cctcgagaaa tatgttgagg    1320
acactaaaat agatctctgg tcatacaacg cggagcttct tgttgccctg gagaaccaac    1380
atacaattga tctaactgac tcagaaatga acaaactgtt tgaaagaaca aagaagcaac    1440
tgagggaaaa tgctgaggat atgggcaatg gttgtttcaa aatataccac aaatgtgaca    1500
atgcctgcat aggatcaatc agaaatggaa cttatgacca tgatgtatac agagatgaag    1560
cattaaacaa ccggttccag atcaaaggcg ttgagctgaa gtcaggatac aaagattgga    1620
tcctatggat ttcctttgcc atatcatgtt ttttgctttg tgttgctttg ttggggttca    1680
tcatgtgggc ctgccaaaaa ggcaacatta ggtgcaacat ttgcatttga gtgcattaat    1740
taaaaacacc cttgtttcta cta                                            1763
```

<210> SEQ ID NO 14
<211> LENGTH: 566
<212> TYPE: PRT
<213> ORGANISM: Influenza A virus

<400> SEQUENCE: 14

Met Lys Thr Ile Ile Ala Leu Ser Tyr Ile Leu Cys Leu Val Phe Ala

```
            1               5                  10                 15
Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
                35                  40                  45

Gln Ile Glu Val Thr Asn Ala Thr Glu Leu Val Gln Ser Ser Ser Thr
 50                  55                  60

Gly Gly Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Asn Asp Glu Ser Phe Asn Trp Thr
 130                 135                 140

Gly Val Thr Gln Asn Gly Thr Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
                180                 185                 190

Leu Tyr Ile Trp Gly Val His His Pro Val Thr Asp Asn Asp Gln Ile
                195                 200                 205

Phe Leu Tyr Ala Gln Ala Ser Gly Arg Ile Thr Val Ser Thr Lys Arg
 210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
                290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Ile Gly Gln Ala Ala Asp Leu Lys
                370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430
```

```
          Lys Ile Asp Leu Trp Ser Tyr Asn Ala Glu Leu Leu Val Ala Leu Glu
              435                 440                 445

Asn Gln His Thr Ile Asp Leu Thr Asp Ser Glu Met Asn Lys Leu Phe
              450                 455                 460

Glu Arg Thr Lys Lys Gln Leu Arg Glu Asn Ala Glu Asp Met Gly Asn
          465                 470                 475                 480

Gly Cys Phe Lys Ile Tyr His Lys Cys Asp Asn Ala Cys Ile Gly Ser
                          485                 490                 495

Ile Arg Asn Gly Thr Tyr Asp His Asp Val Tyr Arg Asp Glu Ala Leu
                      500                 505                 510

Asn Asn Arg Phe Gln Ile Lys Gly Val Glu Leu Lys Ser Gly Tyr Lys
                      515                 520                 525

Asp Trp Ile Leu Trp Ile Ser Phe Ala Ile Ser Cys Phe Leu Leu Cys
                  530                 535                 540

Val Ala Leu Leu Gly Phe Ile Met Trp Ala Cys Gln Lys Gly Asn Ile
          545                 550                 555                 560

Arg Cys Asn Ile Cys Ile
                          565

<210> SEQ ID NO 15
<211> LENGTH: 1445
<212> TYPE: DNA
<213> ORGANISM: Influenza A virus

<400> SEQUENCE: 15
agcaaaagca ggagtaaaga tgaatccaaa tcaaaagata taacgattg gctctgtttc      60 tctcaccatt tccacaatat gcttcttcat gcaaattgcc atcttgataa ctactgtaac     120
attgcatttc aagcaatatg aattcaactc cccccaaac aaccaagtga tgctgtgtga     180
accaacaata atagaaagaa acataacaga gatagtgtat ctgaccaaca ccaccataga     240
gaaggaaata tgccccaaac tagcagaata cagaaattgg tcaaagccgc aatgtaacat     300
tacaggattt gcaccttttt ctaaggacaa ttcgattagg ctttccgctg gtggggacat     360
ctgggtgaca agagaacctt atgtgtcatg cgatcctgac aaatgttatc aatttgccct     420
tgggcaggga acaacactaa acaacgtgca ttcaaatgac acagtacatg ataggacccc     480
ttatcggacc ctattgatga atgagttagg tgttccattt catctgggga ccaagcaagt     540
gtgcatagca tggtccagct caagttgtca cgatggaaaa gcatggctgc atgtttgtgt     600
aacgggggat gataaaaatg caactgctag cttcatttac aatgggaggc ttgtagatag     660
tattgtttca tggtccaaag aaatcctcag gacccaggag tcagaatgcg tttgtatcaa     720
tggaacttgt acagtagtaa tgactgatgg agtgcttca ggaaaagctg atactaaaat     780
actattcatt gaggagggga aaatcgttca tactagcaca ttgtcaggaa gtgctcagca     840
tgtcgaggag tgctcctgct atcctcgata tcttggtgtc agatgtgtct gcagagacaa     900
ctggaaaggc tccaataggc ccatagtaga tataaacata aaggattata gcattgtttc     960
cagttatgtg tgctcaggac ttgttggaga cacacccaga aaaacgaca gctccagcag    1020 tagccattgc ttggatccta acaatgaaga aggtggtcat ggagtgaaag ctgggccctt    1080
tgatgatgga aatgacgtgt ggatgggaag aacgatcagc gagaagttac gctcaggata    1140
tgaaaccttc aaagtcattg aaggctggtc aacccctaat tccaaattgc agataaatag    1200
gcaagtcata gttgacagag gtaataggtc cggttattct ggtattttct ctgttgaagg    1260
caaaagctgc atcaatcggt gctttttatgt ggagttgata aggggaagaa agaggaaac    1320 tgaagtcttg tggacctcaa acagtattgt tgtgttttgt ggcacctcag gtacatatgg    1380
```

-continued

```
aacaggctca tggcctgatg gggcggacat caatctcatg cctatataag ctttcgcaat    1440
tttag                                                                1445
```

<210> SEQ ID NO 16
<211> LENGTH: 469
<212> TYPE: PRT
<213> ORGANISM: Influenza A virus

<400> SEQUENCE: 16

| | | | | | | | | | | | | | | |
|---|---|---|---|---|---|---|---|---|---|---|---|---|---|---|
| Met | Asn | Pro | Asn | Gln | Lys | Ile | Ile | Thr | Ile | Gly | Ser | Val | Ser | Leu | Thr |
| 1 | | | | 5 | | | | | 10 | | | | | 15 | |
| Ile | Ser | Thr | Ile | Cys | Phe | Phe | Met | Gln | Ile | Ala | Ile | Leu | Ile | Thr | Thr |
| | | 20 | | | | | 25 | | | | | 30 | | | |
| Val | Thr | Leu | His | Phe | Lys | Gln | Tyr | Glu | Phe | Asn | Ser | Pro | Pro | Asn | Asn |
| | | | 35 | | | | | 40 | | | | | 45 | | |
| Gln | Val | Met | Leu | Cys | Glu | Pro | Thr | Ile | Ile | Glu | Arg | Asn | Ile | Thr | Glu |
| | 50 | | | | | 55 | | | | | 60 | | | | |
| Ile | Val | Tyr | Leu | Thr | Asn | Thr | Thr | Ile | Glu | Lys | Glu | Ile | Cys | Pro | Lys |
| 65 | | | | | 70 | | | | | 75 | | | | | 80 |
| Leu | Ala | Glu | Tyr | Arg | Asn | Trp | Ser | Lys | Pro | Gln | Cys | Asn | Ile | Thr | Gly |
| | | | | 85 | | | | | 90 | | | | | 95 | |
| Phe | Ala | Pro | Phe | Ser | Lys | Asp | Asn | Ser | Ile | Arg | Leu | Ser | Ala | Gly | Gly |
| | | | 100 | | | | | 105 | | | | | 110 | | |
| Asp | Ile | Trp | Val | Thr | Arg | Glu | Pro | Tyr | Val | Ser | Cys | Asp | Pro | Asp | Lys |
| | | 115 | | | | | 120 | | | | | 125 | | | |
| Cys | Tyr | Gln | Phe | Ala | Leu | Gly | Gln | Gly | Thr | Thr | Leu | Asn | Asn | Val | His |
| 130 | | | | | 135 | | | | | 140 | | | | | |
| Ser | Asn | Asp | Thr | Val | His | Asp | Arg | Thr | Pro | Tyr | Arg | Thr | Leu | Leu | Met |
| 145 | | | | | 150 | | | | | 155 | | | | | 160 |
| Asn | Glu | Leu | Gly | Val | Pro | Phe | His | Leu | Gly | Thr | Lys | Gln | Val | Cys | Ile |
| | | | | 165 | | | | | 170 | | | | | 175 | |
| Ala | Trp | Ser | Ser | Ser | Ser | Cys | His | Asp | Gly | Lys | Ala | Trp | Leu | His | Val |
| | | | 180 | | | | | 185 | | | | | 190 | | |
| Cys | Val | Thr | Gly | Asp | Asp | Lys | Asn | Ala | Thr | Ala | Ser | Phe | Ile | Tyr | Asn |
| | | 195 | | | | | 200 | | | | | 205 | | | |
| Gly | Arg | Leu | Val | Asp | Ser | Ile | Val | Ser | Trp | Ser | Lys | Glu | Ile | Leu | Arg |
| 210 | | | | | 215 | | | | | 220 | | | | | |
| Thr | Gln | Glu | Ser | Glu | Cys | Val | Cys | Ile | Asn | Gly | Thr | Cys | Thr | Val | Val |
| 225 | | | | | 230 | | | | | 235 | | | | | 240 |
| Met | Thr | Asp | Gly | Ser | Ala | Ser | Gly | Lys | Ala | Asp | Thr | Lys | Ile | Leu | Phe |
| | | | | 245 | | | | | 250 | | | | | 255 | |
| Ile | Glu | Glu | Gly | Lys | Ile | Val | His | Thr | Ser | Thr | Leu | Ser | Gly | Ser | Ala |
| | | | 260 | | | | | 265 | | | | | 270 | | |
| Gln | His | Val | Glu | Glu | Cys | Ser | Cys | Tyr | Pro | Arg | Tyr | Leu | Gly | Val | Arg |
| | | 275 | | | | | 280 | | | | | 285 | | | |
| Cys | Val | Cys | Arg | Asp | Asn | Trp | Lys | Gly | Ser | Asn | Arg | Pro | Ile | Val | Asp |
| | 290 | | | | | 295 | | | | | 300 | | | | |
| Ile | Asn | Ile | Lys | Asp | Tyr | Ser | Ile | Val | Ser | Ser | Tyr | Val | Cys | Ser | Gly |
| 305 | | | | | 310 | | | | | 315 | | | | | 320 |
| Leu | Val | Gly | Asp | Thr | Pro | Arg | Lys | Asn | Asp | Ser | Ser | Ser | Ser | Ser | His |
| | | | | 325 | | | | | 330 | | | | | 335 | |
| Cys | Leu | Asp | Pro | Asn | Asn | Glu | Glu | Gly | Gly | His | Gly | Val | Lys | Gly | Trp |
| | | | 340 | | | | | 345 | | | | | 350 | | |
| Ala | Phe | Asp | Asp | Gly | Asn | Asp | Val | Trp | Met | Gly | Arg | Thr | Ile | Ser | Glu |

|     | 355 |     |     | 360 |     |     | 365 |     |     |     |     |     |
| --- | --- | --- | --- | --- | --- | --- | --- | --- | --- | --- | --- | --- |
| Lys | Leu | Arg | Ser | Gly | Tyr | Glu | Thr | Phe | Lys | Val | Ile | Glu | Gly | Trp | Ser |
|     |     | 370 |     |     |     | 375 |     |     |     | 380 |     |     |

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
        450                 455                 460

Asn Leu Met Pro Ile
465

<210> SEQ ID NO 17
<211> LENGTH: 1769
<212> TYPE: DNA
<213> ORGANISM: Influenza A virus

<400> SEQUENCE: 17

```
agcagggaa    aataaaaaca   accaaaatga   aagtaaaact   actggtcctg   ttatgcacat    60
ttacagctac   atatgcagac   acaatatgta   taggctacca   tgccaacaac   tcaaccgaca   120
ctgttgacac   agtacttgag   aagaatgtga   cagtgacaca   ctctgtcaac   ctgcttgagg   180
acagtcacaa   tggaaaatta   tgtctattaa   aaggaatagc   cccactacaa   ttgggtaatt   240
gcagcgttgc   cggatggatc   ttaggaaacc   cagaatgcga   attactgatt   tccagggaat   300
catggtccta   cattgtagaa   aaaccaaatc   tgagaatgg   aacatgttac   ccagggcatt   360
tcgccgacta   tgaggaactg   agggagcaat   tgagttcagt   atcttcattt   gagagattcg   420
aaatattccc   caaagaaagc   tcatggcccca   accacaccac   aaccggagta   tcagcatcat   480
gctcccataa   tggggaaagc   agttttttaca   aaaatttgct   atggctgacg   gggaagaatg   540
gtttgtaccc   aaacctgagc   aagtcctatg   caaacaacaa   agagaaagaa   gtccttgtac   600
tatgggtgt   tcatcacccg   cctaacatag   gtgaccaaag   ggctctctat   catacagaaa   660
atgcttatgt   ctctgtagtg   tcttcacatt   atagcagaaa   attcaccccca   gaaatagcca   720
aaagacccaa   agtaagagat   cgagaaggaa   gaatcaacta   ctactggact   ctacttgaac   780
ccggggatac   aataatattt   gaggcaaatg   gaaatctaat   agcgccaaga   tatgctttcg   840
cactgagtag   aggctttgga   tcaggaatca   tcaactcaaa   tgcaccaatg   gatgaatgtg   900
atgcgaagtg   ccaaacacct   cagggagcta   taaacagcag   tcttccttcc   cagaatgtac   960
accctgtcac   aataggagag   tgtccaaagt   atgtcaggag   tgcaaaatta   aggatggtta  1020
caggactaag   gaacatccca   tccattcaat   ccagaggttt   gttttggagcc   attgccggtt  1080
tcattgaagg   ggggtggact   ggaatggtag   atggttggta   tggttatcat   catcagaatg  1140
agcaaggatc   tggctatgct   gcagatcaaa   aaagcacaca   aatgccatt   aatgggatta  1200
caaacaaggt   gaattctgta   attgagaaaa   tgaacactca   attcacagct   gtgggcaaag  1260
aattcaacaa   attggaaaga   aggatggaaa   acttaaataa   aaaagttgat   gatgggttta  1320
tagacatttg   gacatataat   gcagaattgt   tggttctact   ggaaaatgaa   aggactttgg  1380
atttccatga   ctccaatgtg   aagaatctgt   atgaaaagt   aaaaagccaa   ttaaagaata  1440
atgccaaaga   aataggaaat   gggtgttttg   aattctatca   caagtgtaac   gatgaatgca  1500
```

-continued

```
tggagagtgt aaaaaatgga acttatgact atccaaaata ttccgaagaa tcaaagttaa    1560
acagggagaa aattgatgga gtgaaattgg aatcaatggg agtctatcag attctggcga    1620
tctactcaac agtcgccagt tctctggttc ttttggtctc cctgggggca atcagcttct    1680
ggatgtgttc caatgggtct ttgcagtgta gaatatgcat ctaagaccag aatttcagaa    1740
atataaggaa aacacccctt gtttctact                                      1769
```

```
<210> SEQ ID NO 18
<211> LENGTH: 565
<212> TYPE: PRT
<213> ORGANISM: Influenza A virus

<400> SEQUENCE: 18
```

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Arg Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
```

```
                   325                 330                 335
Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 19
<211> LENGTH: 1463
<212> TYPE: DNA
<213> ORGANISM: Influenza A virus

<400> SEQUENCE: 19
agcaaaagca ggagtttaaa atgaacccaa atcaaaaaat aataaccatt ggatcaatca      60
gtatagcaat cggaataatt agtctaatat tgcaaatagg aaatattatt tcaatatggg     120
ctagtcactc aatccaaact ggaagtcaaa accacactgg aatatgcaac caaagaatca     180
tcacatatga aaacagcacc tgggtgaata acacatatgt taatattaac aacaccaatg     240
ttgttgctga aaaggacaaa acttcagtga cattggccgg caattcatct ctttgttcta     300
tcagtgggtg gctatatac acaaaagaca cagcataag aattggctcc aaaggagatg      360 ttttttgtcat aagagaacct ttcatatcat gttctcactt ggaatgcaga acctttttc     420 tgacccaagg tgctctatta aatgacaaac attcaaatgg accgtaaag acagaagtc      480 cttatagggc ttaatgagc tgtcctctag gtgaagctcc gtccccatac aattcaaggt     540
ttgaatcagt gcatggtca gcaagcgcat gccatgatgg catgggctgg ttaacaatcg     600
gaatttctgg tccagacaat ggagctgtgg ctgtactaaa atacaacgga ataataactg     660
aaaccataaa aagttggaaa aagcgaatat taagaacaca agagtctgaa tgtgtctgta     720
tgaacgggtc atgttttcac cataatgaccg atggccccgag taatgggcc gcctcgtaca     780
```

```
aaattttcaa gatcgaaaag gggaaggtta ccaaaacaat agagttgaat gcacccaatt      840
ttcattatga ggaatgttcc tgttacccag acactggcac agtgatgtgt gtatgcagag      900
acaactggca tggttcaaat cgaccttggg tgtcttttaa tcaaaacttg gattatcaaa      960
taggatacat ctgcagtgga gtgttcggtg acaatccgcg tcccaaagat ggggagggca     1020
gctgcaatcc agtgactgtt gatggagcag acggagtaaa agggttttca tacaaatatg     1080
gtaatggtgt ttggatagga aggaccaaaa gtaacagact tagaaagggg tttgagatga     1140
tttgggatcc taatgatgg acaaataccg acagtgattt ctcagtgaaa caggatgttg      1200
tagcaataac tgattggtca gggtacagcg aagttttgt tcaacatcct gagttaacag       1260
gattggactg tataagacct tgcttctggg ttgagttagt cagagggctg cctagggaaa     1320
atacaacaat ctggactagt gggagcagca tttcttttg tggcgttaat agtggtactg       1380
caaactggtc ttggccagac ggtgctgagt tgccgttcac cattgacaag tagttcgttg     1440
aaaaaaaact ccttgtttct act                                              1463
```

<210> SEQ ID NO 20
<211> LENGTH: 470
<212> TYPE: PRT
<213> ORGANISM: Influenza A virus

<400> SEQUENCE: 20

```
Met Asn Pro Asn Gln Lys Ile Ile Thr Ile Gly Ser Ile Ser Ile Ala
1               5                   10                  15

Ile Gly Ile Ile Ser Leu Ile Leu Gln Ile Gly Asn Ile Ile Ser Ile
            20                  25                  30

Trp Ala Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Asn
    50                  55                  60

Thr Tyr Val Asn Ile Asn Asn Thr Asn Val Val Ala Glu Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Gly Ala Ala Ser Tyr Lys Ile Phe
                245                 250                 255
```

| Lys | Ile | Glu | Lys | Gly | Lys | Val | Thr | Lys | Thr | Ile | Glu | Leu | Asn | Ala | Pro |
|     |     |     | 260 |     |     |     |     | 265 |     |     |     |     |     | 270 |     |

| Asn | Phe | His | Tyr | Glu | Glu | Cys | Ser | Cys | Tyr | Pro | Asp | Thr | Gly | Thr | Val |
|     |     |     | 275 |     |     |     |     | 280 |     |     |     |     | 285 |     |     |

| Met | Cys | Val | Cys | Arg | Asp | Asn | Trp | His | Gly | Ser | Asn | Arg | Pro | Trp | Val |
|     | 290 |     |     |     |     |     |     | 295 |     |     |     |     | 300 |     |     |

| Ser | Phe | Asn | Gln | Asn | Leu | Asp | Tyr | Gln | Ile | Gly | Tyr | Ile | Cys | Ser | Gly |
| 305 |     |     |     |     | 310 |     |     |     |     | 315 |     |     |     |     | 320 |

| Val | Phe | Gly | Asp | Asn | Pro | Arg | Pro | Lys | Asp | Gly | Glu | Gly | Ser | Cys | Asn |
|     |     |     |     | 325 |     |     |     |     | 330 |     |     |     |     | 335 |     |

| Pro | Val | Thr | Val | Asp | Gly | Ala | Asp | Gly | Val | Lys | Gly | Phe | Ser | Tyr | Lys |
|     |     |     |     | 340 |     |     |     |     | 345 |     |     |     |     | 350 |     |

| Tyr | Gly | Asn | Gly | Val | Trp | Ile | Gly | Arg | Thr | Lys | Ser | Asn | Arg | Leu | Arg |
|     |     |     | 355 |     |     |     |     | 360 |     |     |     |     |     | 365 |     |

| Lys | Gly | Phe | Glu | Met | Ile | Trp | Asp | Pro | Asn | Gly | Trp | Thr | Asn | Thr | Asp |
|     | 370 |     |     |     |     | 375 |     |     |     |     | 380 |     |     |     |     |

| Ser | Asp | Phe | Ser | Val | Lys | Gln | Asp | Val | Val | Ala | Ile | Thr | Asp | Trp | Ser |
| 385 |     |     |     |     | 390 |     |     |     |     | 395 |     |     |     |     | 400 |

| Gly | Tyr | Ser | Gly | Ser | Phe | Val | Gln | His | Pro | Glu | Leu | Thr | Gly | Leu | Asp |
|     |     |     |     | 405 |     |     |     |     | 410 |     |     |     |     | 415 |     |

| Cys | Ile | Arg | Pro | Cys | Phe | Trp | Val | Glu | Leu | Val | Arg | Gly | Leu | Pro | Arg |
|     |     |     | 420 |     |     |     |     | 425 |     |     |     |     | 430 |     |     |

| Glu | Asn | Thr | Thr | Ile | Trp | Thr | Ser | Gly | Ser | Ser | Ile | Ser | Phe | Cys | Gly |
|     |     |     | 435 |     |     |     |     | 440 |     |     |     |     | 445 |     |     |

| Val | Asn | Ser | Gly | Thr | Ala | Asn | Trp | Ser | Trp | Pro | Asp | Gly | Ala | Glu | Leu |
|     | 450 |     |     |     |     | 455 |     |     |     |     | 460 |     |     |     |     |

| Pro | Phe | Thr | Ile | Asp | Lys |
| 465 |     |     |     |     | 470 |

<210> SEQ ID NO 21
<211> LENGTH: 1883
<212> TYPE: DNA
<213> ORGANISM: Influenza B virus

<400> SEQUENCE: 21

```
gcagaagcag agcatttct aatatccaca aaatgaaggc aataattgta ctactcatgg     60
tagtaacatc caatgcagat cgaatctgca ctgggataac atcgtcaaac tcaccacatg    120
ttgtcaaaac tgctactcaa ggggaggtca atgtgactgg tgtaatacca ctgacaacaa    180
cacccaccaa atctcatttt gcaaatctca aaggaacaga aaccagaggg aaactatgcc    240
caaaatgcct caactgcaca gatctggacg tggccttggg cagaccaaaa tgcacgggga    300
acataccctc ggcaagagtt tcaatactcc atgaagtcag acctgttaca tctgggtgct    360
ttcctataat gcacgacaga acaaaaatta gacagctgcc taaccttctc agaggatacg    420
aacatatcag gttatcaact cataacgtta tcaatgcaga aaatgcacca ggaggaccct    480
acaaaattgg aacctcaggg tcttgcccta acgttaccaa tggaaacgga tttttcgcaa    540
caatggcttg ggccgtccca aaaaacgaca acaacaaaac agcaacaaat tcattaacaa    600
tagaagtacc atacatttgt acagaaggag aagaccaaat taccgtttgg gggttccact    660
ctgatagcga aacccaaatg gcaaagctct atggggactc aaagccccag aagttcacct    720
catctgccaa cggagtgacc acacattacg tttcacagat tggtggcttc ccaaatcaaa    780
cagaagacgg aggactacca caaagtggta gaattgttgt tgattacatg gtgcaaaaat    840
ctgggaaaac aggaacaatt acctatcaaa gaggtatttt attgcctcaa aaagtgtggt    900
```

-continued

```
gcgcaagtgg caggagcaag gtaataaaag gatccttgcc tttaattgga gaagcagatt    960
gcctccacga aaatacggt ggattaaaca aaagcaagcc ttactacaca ggggaacatg    1020
caaaggccat aggaaattgc ccaatatggg tgaaaacacc cttgaagctg ccaatggaa    1080
ccaaatatag acctcctgca aaactattaa aggaaagggg tttcttcgga gctattgctg    1140
gtttcttaga aggaggatgg gaaggaatga ttgcaggttg gcacggatac acatcccatg    1200
gggcacatgg agtagcggtg gcagcagacc ttaagagcac tcaagaggcc ataaacaaga    1260
taacaaaaaa tctcaactct ttgagtgagc tggaagtaaa gaatcttcaa agactaagcg    1320
gtgccatgga tgaactccac aacgaaatac tagaactaga cgagaaagtg gatgatctca    1380
gagctgatac aataagctca caaatagaac tcgcagtcct gctttccaat gaaggaataa    1440
taaacagtga agatgagcat ctcttggcgc ttgaaagaaa gctgaagaaa atgctgggcc    1500
cctctgctgt agagataggg aatggatgct tgaaaccaa acacaagtgc aaccagacct    1560
gtctcgacag aatagctgct ggtacctttg atgcaggaga atttctctc cccactttg    1620
attcactgaa tattactgct gcatctttaa atgacgatgg attggataat catactatac    1680
tgctttacta ctcaactgct gcctccagtt tggctgtaac attgatgata gctatctttg    1740
ttgtttatat ggtctccaga gacaatgttt cttgctccat ctgtctataa ggaaagttaa    1800
accctgtatt ttcctttatt gtagtgcttg tttgcttgtt accattacaa aaacgttat    1860
tgaaaaatgc tcttgttact act                                           1883
```

<210> SEQ ID NO 22
<211> LENGTH: 585
<212> TYPE: PRT
<213> ORGANISM: Influenza B virus

<400> SEQUENCE: 22

```
Met Lys Ala Ile Ile Val Leu Leu Met Val Val Thr Ser Asn Ala Asp
 1               5                  10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
```

-continued

His Ser Asp Ser Glu Thr Gln Met Ala Lys Leu Tyr Gly Asp Ser Lys
210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 23
<211> LENGTH: 1536
<212> TYPE: DNA
<213> ORGANISM: Influenza B virus

<400> SEQUENCE: 23

```
agcagaagca gagcatcttc tcaaaactga agcaaatagg ccaaaaatga acaatgctac      60
cttcaactat acaaacgtta accctatttc tcacatcagg gggagtatta ttatcactat     120
atgtgtcagc ttcattgtca tacttactat attcggatat attgctaaaa ttcccatcaa     180
cagaaattac tgcaccaaca atgccattgg attgtgcaaa cgcatcaaat gttcaggctg     240
tgaaccgttc tgcaacaaaa ggggtgacac ttcttctccc agaaccggag tggacatacc     300
cgcgtttatc ttgcccgggc tcaaccttc agaaagcact cctaattagc cctcatagat     360
tcggagaaac caaggaaac tcagctccct tgataataag ggaacctttt attgcttgtg     420
gaccaaagga atgcaaacac tttgctctaa cccactatgc agcccaacca gggggatact     480
acaatggaac aagaggagac agaaacaagc tgaggcatct aatttcagtc aaattgggca     540
aaatcccaac agtagaaaac tccattttcc acatggcagc atggagcggg tccgcatgcc     600
atgatggtaa ggaatggaca tatatcggag ttgatggccc tgacaataat gcattgctca     660
aaataaaata tggagaagca tatactgaca cataccattc ctatgcaaac aacatcctaa     720
gaacacaaga aagtgcctgc aattgcatcg ggggaaattg ttatcttatg ataactgatg     780
gctcagcttc aggtgttagt gaatgcagat tcttaagat tcgagagggc cgaataataa     840
aagaaatatt tccaacagga agaataaaac atactgaaga atgcacatgc ggatttgcta     900
gcaataaaac catagaatgt gcctgtagag ataacagtta cacagcaaaa agacccttg     960
tcaaattaaa cgtggagact gatacagcag aaataagatt gatgtgcaca gagacttatt    1020
tggacacccc cagaccagat gatggaagca taacagggcc ttgtgaatct aatgggggaca   1080
aagggagtgg aggcatcaag ggaggatttg tccatcaaag aatggcatcc aagattggaa    1140
ggtggtactc tcgaacgatg tctaaaacta aaaggatggg gatgggctg tatgtcaagt    1200
atgatggaga cccatgggct gacagtgatg cccttgcttt tagtgagta atggtttcaa    1260
tggaagaacc tggttggtac tcctttggct tcgaaataaa agacaagaaa tgtgatgtcc   1320
cctgtattgg gatagagatg gtacatgatg gtggaaaaga gacttggcac tcagcagcta   1380
cagccattta ctgtttaatg ggctcaggac agctgctgtg ggacactgtc acaggtgtta   1440
atatggctct gtaatggagg aatggttgag tctgttctaa acccttttgtt cctatttgt   1500
ttgaacaatt gtccttactg aacttaattg tttctg                              1536
```

<210> SEQ ID NO 24
<211> LENGTH: 466
<212> TYPE: PRT
<213> ORGANISM: Influenza B virus

<400> SEQUENCE: 24

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Pro Ser Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95
```

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
            115                 120                 125

His Phe Ala Leu Thr His Tyr Ala Ala Gln Pro Gly Gly Tyr Tyr Asn
130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
                180                 185                 190

Val Asp Gly Pro Asp Asn Asn Ala Leu Leu Lys Ile Lys Tyr Gly Glu
            195                 200                 205

Ala Tyr Thr Asp Thr Tyr His Ser Tyr Ala Asn Asn Ile Leu Arg Thr
210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Ile Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
370                 375                 380

Gly Asp Pro Trp Ala Asp Ser Asp Ala Leu Ala Phe Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asn Met
            450                 455                 460

Ala Leu
465

<210> SEQ ID NO 25
<211> LENGTH: 1881
<212> TYPE: DNA
<213> ORGANISM: Influenza B virus

<400> SEQUENCE: 25

```
gaagcagagc attttctaat atccacaaaa tgaaggcaat aattgtacta ctcatggtag      60
taacatccaa tgcagatcga atctgcactg ggataacatc gtcaaactca ccacatgtcg     120
tcaaaactgc tactcaaggg gaggtcaatg tgactggtgt aataccactg acaacaacac     180
ccaccaaatc tcattttgca aatctcaaag gaacagaaac caggggggaaa ctatgcccaa     240 aatgcctcaa ctgcacagat ctggacgtag ccttgggcag accaaaatgc acggggaaaa     300
taccctcggc aagagtttca atactccatg aagtcagacc tgttacatct gggtgctttc     360
ctataatgca cgacagaaca aaaattagac agctgcctaa ccttctccga ggatacgaac     420
atatcaggtt atcaacccat aacgttatca atgcagaaaa tgcaccagga ggaccctaca     480
aaattggaac ctcagggtct tgccctaaca ttaccaatgg aaacggattt ttcgcaacaa     540
tggcttgggc cgtcccaaaa aacgacaaaa acaaaacagc aacaaatcca ttaacaatag     600
aagtaccata catttgtaca gaaggagaag accaaattac cgtttggggg ttccactctg     660
acgacgagac ccaaatggca aagctctatg gggactcaaa gccccagaag ttcacctcat     720
ctgccaacgg agtgaccaca cattacgttt cacagattgg tggcttccca aatcaaacag     780
aagacggagg actaccacaa agtggtagaa ttgttgttga ttacatggtg caaaaatctg     840
ggaaaacagg aacaattacc tatcaagggg tatttatt gcctcaaaag gtgtggtgcg     900
caagtggcag gagcaaggta ataaaaggat ccttgccttt aattggagaa gcagattgcc     960
tccacgaaaa atacggtgga ttaaacaaaa gcaagcctta ctacacaggg aacatgcaa    1020 aggccatagg aaattgccca atatgggtga aacacccctt gaagctggcc aatggaacca    1080
aatatagacc tcctgcaaaa ctattaaagg aaaggggttt cttcggagct attgctggtt    1140
tcttagaagg aggatgggaa ggaatgattg caggttggca cggatacaca tcccatgggg    1200
cacatggagt agcggtggca gcagacctta agagcactca agaggccata aacaagataa    1260 caaaaatct caactctttg agtgagctgg aagtaaagaa tcttcaaaga ctaagcggtg    1320
ccatggatga actccacaac gaaatactag aactagatga gaaagtggat gatctcagag    1380
ctgatacaat aagctcacaa atagaactcg cagtcctgct ttccaatgaa ggaataataa    1440
acagtgaaga tgaacatctc ttggcgcttg aaagaaagct gaagaaaatg ctgggccccct    1500 ctgctgtaga gatagggaat ggatgctttg aaaccaaaca caagtgcaac cagacctgtc    1560
tcgacagaat agctgctggt acctttgatg caggagaatt ttctctcccc cctttgatt    1620 cactgaatat tactgctgca tctttaaatg acgatggatt ggataatcat actatactgc    1680
tttactactc aactgctgcc tccagtttgg ctgtaacact gatgatagct atctttgttg    1740
tttatatggt ctccagagac aatgtttctt gctccatctg tctataaggg aagttaagcc    1800
ctgtattttc ctttattgta gtgcttgttt acttgttgtc attacaaaga aacgttattg    1860
aaaaatgctc ttgttactac t                                              1881
```

<210> SEQ ID NO 26
<211> LENGTH: 585
<212> TYPE: PRT
<213> ORGANISM: Influenza B virus

<400> SEQUENCE: 26

```
Met Lys Ala Ile Ile Val Leu Leu Met Val Val Thr Ser Asn Ala Asp
 1               5                  10                  15

Arg Ile Cys Thr Gly Ile Thr Ser Ser Asn Ser Pro His Val Val Lys
             20                  25                  30

Thr Ala Thr Gln Gly Glu Val Asn Val Thr Gly Val Ile Pro Leu Thr
         35                  40                  45
```

```
Thr Thr Pro Thr Lys Ser His Phe Ala Asn Leu Lys Gly Thr Glu Thr
         50                  55                  60

Arg Gly Lys Leu Cys Pro Lys Cys Leu Asn Cys Thr Asp Leu Asp Val
 65                  70                  75                  80

Ala Leu Gly Arg Pro Lys Cys Thr Gly Lys Ile Pro Ser Ala Arg Val
                 85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asp Glu Thr Gln Met Ala Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
```

```
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 27
<211> LENGTH: 1557
<212> TYPE: DNA
<213> ORGANISM: Influenza B virus

<400> SEQUENCE: 27
agcagaagca gagcatcttc tcaaaactga agcaaatagg ccaaaaatga acaatgctac      60
cttcaactat acaaacgtta accctatttc tcacatcagg gggagtatta ttatcactat     120
atgtgtcagc ttcattatca tacttactat attcggatat attgctaaaa ttctcaccaa     180
cagaaataac tgcaccaaca atgccattgg attgtgcaaa cgcatcaaat gttcaggctg     240
tgaaccgttc tgcaacaaaa ggggtgacac ttcttctccc agaaccggag tggacatacc     300
cgcgtttatc ttgcccgggc tcaacctttc agaaagcact cctaattagc cctcatagat     360
tcggagaaac caaaggaaac tcagctccct tgataataag ggaacctttt attgcttgtg     420
gaccaaatga atgcaaacac tttgctctaa cccattatgc agcccaacca ggggggatact    480 acaatggaac aagaggagac agaaacaagc tgaggcatct aatttcagtc aaattgggca     540
aaatcccaac agtagaaaac tccattttcc acatggcagc atggagcggg tccgcgtgcc     600
atgatggtaa ggaatggaca tatatcggag ttgatggccc tgacaataat gcattgctca     660
aagtaaaata tggagaagca tatactgaca cataccattc ctatgcaaac aaaatcctaa     720
gaacacaaga aagtgcctgc aattgcatcg gggaaattg ttatcttatg ataactgatg     780
gctcagcttc aggtgttagt gaatgcagat ttcttaagat tcgagagggc cgaataataa     840
aagaaatatt tccaacagga agagtaaaac acactgagga atgcacatgc ggatttgcca     900
gcaataaaac catagaatgt gcctgtagag ataacagtta cacagcaaaa agaccttttg     960
tcaaattaaa cgtggagact gatacagcag aaataagatt gatgtgcaca gatacttatt    1020
tggacacccc cagaccaaac gatggaagca taacaggccc ttgtgaatct aatggggaca    1080
aagggagtgg aggcatcaag ggaggatttg ttcatcaaag aatggaatcc aagattggaa    1140
ggtggtactc tcgaacgatg tctaaaactg aaaggatggg gatgggactg tatgtcaagt    1200
atgatggaga cccatgggct gacagtgatg ccctagcttt tagtggagta atggtttcaa    1260
tgaaagaacc tggttggtac tcctttggct tcgaaataaa agataagaaa tgcgatgtcc    1320
cctgtattgg gatagagatg gtacatgatg gtggaaaaga gacttggcac tcagcagcaa    1380
cagccattta ctgtttaatg ggctcaggac agctgctgtg ggacactgtc acaggtgttg    1440
acatggctct gtaatggagg aatggttgag tctgttctaa accctttgtt cctgttttgt    1500
```
ttgaacaatt gtccttacta aacttaattg tttctgaaaa atgctcttgt tactact    1557

<210> SEQ ID NO 28
<211> LENGTH: 466
<212> TYPE: PRT
<213> ORGANISM: Influenza B virus

<400> SEQUENCE: 28

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Asn Glu Cys Lys
        115                 120                 125

His Phe Ala Leu Thr His Tyr Ala Ala Gln Pro Gly Gly Tyr Tyr Asn
    130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Lys Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Asp
305                 310                 315                 320

Thr Tyr Leu Asp Thr Pro Arg Pro Asn Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Glu Ser Lys Ile Gly Arg Trp Tyr Ser Arg Thr
        355                 360                 365

```
                              -continued
Met Ser Lys Thr Glu Arg Met Gly Met Gly Leu Tyr Val Lys Tyr Asp
        370                 375                 380

Gly Asp Pro Trp Ala Asp Ser Asp Ala Leu Ala Phe Ser Gly Val Met
385                 390                 395                 400

Val Ser Met Lys Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
                420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
        450                 455                 460

Ala Leu
465

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Lys Lys
1
```

INFLUENZA HEMAGGLUTININ AND NEURAMINIDASE VARIANTS

RELATED PATENT APPLICATIONS

This patent application is a national stage application under 35 U.S.C. section 371 of international patent application number PCT/US2009/050070, filed on Jul. 9, 2009, entitled INFLUENZA HEMAGGLUTININ AND NEURAMINIDASE VARIANTS, naming Chin-Fen Yang and George Kemble as inventors, and designated by attorney docket no. MDI-0153-PC3, which claims the benefit of U.S. Provisional Patent Application Nos. 61/079,894, filed on Jul. 11, 2008; 61/110,702, filed on Nov. 3, 2008; and 61/178,592, filed on May 15, 2009. The entirety of each of these patent applications is hereby incorporated by reference, including all text, tables and drawings.

SEQUENCE LISTING

The instant application contains a Sequence Listing which has been submitted in ASCII format via EFS-Web and is hereby incorporated by reference in its entirety. Said ASCII copy, created on Jan. 19, 2011, is named MDI-0153-US3.txt and is 95,354 bytes in size.

BACKGROUND OF THE INVENTION

Vaccines against various and evolving strains of influenza are important from a community health standpoint, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread between various species, thereby necessitating the continuous production of new vaccines.

Numerous vaccines capable of producing a protective immune response specific for different influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus."

Because of the continual emergence (or re-emergence) or different influenza strains, new influenza vaccines are continually desired. Such vaccines typically are created using antigenic moieties of the newly emergent virus strains so, therefore, polypeptides and polynucleotides of novel, newly emergent, or newly re-emergent virus strains (especially sequences of antigenic genes) are highly desirable. Furthermore, such sequences within preferred vectors are also quite highly desired.

The present invention provides new and/or newly isolated influenza hemagglutinin and neuraminidase variants, optionally within preferred vectors, that are capable of use in production of numerous types of vaccines as well as in research, diagnostics, etc. Numerous other benefits will become apparent upon review of the following

SUMMARY OF THE INVENTION

In some aspects herein, the invention comprises an isolated or recombinant polypeptide that is selected from: the polypeptides comprising an amino acid sequence encoded by any one of the nucleotide sequences selected from SEQ ID NO:1, 3, 5, 7, 9, 11, 13, 15, 17, 19, 21, 23, 25 and 27; the polypeptides comprising an amino acid sequence encoded by any one of the nucleotide sequences selected from residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, residues 1116-1787 of SEQ ID NO:25; the polypeptides comprising an amino acid sequence selected from SEQ ID NO:2, 4, 6, 8, 10, 12, 14, 16, 18, 20, 22, 24, 26 and 28; the polypeptides comprising an amino acid sequence selected from: residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26; any polypeptide that is encoded by a polynucleotide sequence which hybridizes under highly stringent conditions over substantially the entire length of a polynucleotide sequence of the sequence listing; and, a fragment of any of the above wherein the sequence comprises a hemagglutinin or neuraminidase polypeptide, or a fragment of a hemagglutinin or neuraminidase polypeptide. In various embodiments, the isolated or recombinant polypeptides of the invention are substantially identical to about 300 contiguous amino acid residues of any of the above polypeptides. In yet other embodiments, the invention comprises isolated or recombinant polypeptides (comprising hemagglutinin or neuraminidase or fragments of hemagglutinin or neuraminidase), that comprise an amino acid sequence that is substantially identical over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids contiguous of any of SEQ ID NO: 2, 4, 6, 8, 10, 12, 14, 16, 18, 20, 22, 24, 26 and 28. In yet other embodiments, the invention comprises isolated or recombinant polypeptides (e.g., comprising neuraminidase, hemagglutinin or fragments of neuraminidase or hemagglutinin), that comprise an amino acid sequence that is substantially identical over at least about 350 amino acids; over at least about 400 amino acids; over at least about 436 amino acids; over at least about 450 amino acids; over at least about 451 amino acids; over at least about 465 amino acids; over at least about 466 amino acids; over at least about 469 amino acids; or over at least about 470 amino acids contiguous of any of the polypeptides of any of SEQ ID NO: 2, 4, 6, 8, 10, 12, 14, 16, 18, 20, 22, 24, 26 and 28. Of course, in some embodiments, the polypeptide sequence (e.g., as listed in the sequence listing herein, e.g., SEQ ID NO: 2, 4, 6, 8, 10, 12, 14, 16, 18, 20, 22, 24, 26 and 28) comprises less than 565, 559, etc. amino acids. In yet other embodiments, the polypeptides of the invention optionally comprise fusion proteins, proteins with a leader sequence, a precursor polypeptide, proteins with a secretion signal or a localization signal, or proteins with an epitope tag, an E-tag, or a His epitope tag, etc. In still other embodiments, the invention comprises a polypeptide comprising a sequence having at least 95%, at least 96%, at least 97%, at least 98%, at least 98.5%, at least 99%, at least 99.2%, at least 99.4%, at least 99.6%, at least 99.8%, or at least 99.9% sequence identity to at least one polypeptide listed above (e.g., of SEQ ID NO: 2, 4, 6, 8, 10, 12, 14, 16, 18, 20, 22, 24, 26 and 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26). In some embodiments, such polypeptides are immunogenic. The HA sequences of the invention can comprise both those sequences with unmodified and those with modified polybasic cleavage sites.

In other aspects, the invention comprises a composition with one or more polypeptide listed above, or fragments thereof The invention also includes polypeptides that are specifically bound by a polyclonal antisera raised against at least 1 antigen that comprises at least one amino acid sequence described above (e.g., SEQ ID NO: 2, 4, 6, 8, 10, 12, 14, 16, 18, 20, 22, 24, 26 and 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26), or a fragment thereof Such antibodies specific for the polypeptides described above are also features of the invention. The polypeptides of the invention are optionally immunogenic.

The invention also encompasses immunogenic compositions comprising an immunologically effective amount of one or more of the polypeptides described above, as well as methods for stimulating the immune system of an individual to produce a protective immune response against an influenza virus comprising administering to the individual an immunologically effective amount of one or more of the polypeptides described above (e.g., a polypeptide comprising the amino acid sequence of SEQ ID NO: 2, 4, 6, 8, 10, 12, 14, 16, 18, 20, 22, 24, 26 or 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 or residues 363-585 of SEQ ID NO:26) in a physiologically acceptable carrier. In one embodiment, an immunogenic composition of the invention is a trivalent immunogenic composition comprising three reassortant influenza viruses. In one embodiment, an immunogenic composition of the invention is a trivalent immunogenic composition comprising two reassortant influenza A viruses and a reassortant influenza B virus. In one embodiment, an immunogenic composition of the invention is a trivalent immunogenic composition comprising a reassortant influenza A virus of the H1 type, a reassortant influenza A virus of the H3 type and a reassortant influenza B virus. In another embodiment, an immunogenic composition of the invention is a tetravalent immunogenic composition comprising four reassortant influenza viruses. In one embodiment, an immunogenic composition of the invention is a tetravalent immunogenic composition comprising two reassortant influenza A viruses and two reassortant influenza B viruses. In one embodiment, an immunogenic composition of the invention is a tetravalent immunogenic composition comprising a reassortant influenza A virus of the H1 type, a reassortant influenza A virus of the H3 type, a reassortant influenza B virus of the Victoria lineage and a reasortant influenza B virus of the Yamagata lineage.

Additionally, the invention encompasses a reassortant influenza virus that comprises a genome segment encoding one or more of the polypeptides described above (e.g., a polypeptide comprising the amino acid sequence of SEQ ID NO: 2, 4, 6, 8, 10, 12, 14, 16, 18, 20, 22, 24, 26 or 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 or residues 363-585 of SEQ ID NO:26), in addition to immunogenic compositions comprising an immunologically effective amount of such reassortant influenza virus. Methods for stimulating the immune system of an individual to produce a protective immune response against influenza virus comprising administering an immunologically effective amount of such reassortant influenza virus in a physiologically acceptable carrier are also part of the invention. In one embodiment, a reassortant influenza virus of the invention is a 6:2 reassortant virus comprising 6 internal genome segments from one or more donor virus (e.g. A/AA/6/60, B/Ann Arbor/1/66, A/Puerto Rico/8/34, which is more commonly known as PR8, B/Leningrad/14/17/55, B/14/5/1, B/USSR/60/69, B/Leningrad/179/86, B/Leningrad/14/55, or B/England/2608/76) and further comprising 2 genome segments (typically and preferably encoding HA and NA or fragments thereof) comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or from nucleotide sequences similar, as defined herein, to SEQ ID NO: 1, 3, 5, 7, 9, 11, 13, 15, 17, 19, 21, 23, 25 and 27. Immunogenic compositions comprising such reassortant (recombinant) virus are also features of the invention.

In other aspects, the invention comprises an isolated or recombinant polynucleotide that is selected from: the polynucleotides comprising a nucleotide sequence selected from SEQ ID NO: 1, 3, 5, 7, 9, 11, 13, 15, 17, 19, 21, 23, 25 and 27 or complementary sequences thereof; the polynucleotides comprising a nucleotide sequence selected from residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or complementary sequences thereof; the polynucleotides encoding a polypeptide comprising an amino acid sequence selected from SEQ ID NO: 2, 4, 6, 8, 10, 12, 14, 16, 18, 20, 22, 24, 26 and 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26 or complementary nucleotide sequences thereof; a polynucleotide sequence which hybridizes under highly stringent conditions over substantially the entire length of any of the above polynucleotide sequences, and a polynucleotide sequence comprising all or a fragment of any of the above polynucleotide sequences wherein the sequence encodes a hemagglutinin or neuraminidase polypeptide or one or more HA or NA fragments. Such polynucleotides can be DNA, RNA, cRNA, DNA:RNA hybrids, single stranded polynucleotide, double stranded polynucleotide, etc. The invention also includes any of the above polynucleotides that encode a hemagglutinin or neuraminidase polypeptide, or a hemagglutinin or neuraminidase fragments. Other aspects of the invention include isolated or recombinant polynucleotides that encode a polypeptide (optionally a hemagglutinin or neuraminidase polypeptide) whose sequence has at least 95% identity, at least 96% identity, at least 97% identity, at least 98% identity, at least 98.5% identity, at least 99% identity, at least 99.2% identity, at least 99.4% identity, at least 99.6% identity, at least 99.8% identity, or at least 99.9% identity to at least one of the above described polypeptide. The invention also includes isolated or recombinant polynucleotides encoding a polypeptide of hemagglutinin or neuraminidase produced by mutating or recombining one or more above described polynucleotide sequence. The polynucleotide sequences of the invention can optionally comprise one or more of, e.g., a leader sequence, a precursor sequence, or an epitope tag sequence or the like, and can optionally encode a fusion protein (e.g., with one or more additional nuclotide sequences). Such polynucleotides of the invention can optionally encode immunogenic polypeptides.

In yet other embodiments, the invention comprises a composition of matter having two or more of the above described polynucleotides or fragments thereof (e.g., a library comprising at least about 2, 5, 10, 50 or more polynucleotides). Such compositions can optionally be produced by cleaving one or more above described polynucleotide (e.g., mechanically, chemically, enzymatically with a restriction endonuclease/RNAse/DNAse, etc.). Other compositions of the invention include, e.g., compositions produced by incubating one or more above described polynucleotide in the presence of deoxyribonucleotide triphosphates and a thermostable polymerase Immunogenic compositions having an immunologically effective amount of any of the above polynucleotides are also within the current invention.

Also within the invention are reassortant influenza viruses comprising any of the above described polynucleotides. In one embodiment such reassortant viruses are 6:2 reassortant viruses comprising 6 internal genome segments from one or more donor virus (e.g., A/AA/6/60, B/AA/1/66 (also sometimes referred to herein as B/Ann Arbor/1/66), B/Leningrad/14/17/55, B/14/5/1, B/USSR/60/69, B/Leningrad/179/86, B/Leningrad/14/55, or B/England/2608/76 or A/Puerto Rico/8/34) and 2 genome segments comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25. In one embodiment, the two genome segments encode a hemagglutinin and/or neuraminidase. Immunogenic compositions comprising immunologically effective amounts of such reassortant/recombinant influenza virus are also within purview of the current invention.

Vectors comprising one or more polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or fragments thereof are also within the current invention. Such vectors (e.g., expression vectors) can optionally be plasmids, cosmids, phage, viruses, virus fragments, etc. Especially preferred embodiments comprise plasmid vectors useful in plasmid rescue methods to produce virus (e.g., typically reassortant/recombinant virus for use in vaccines). Examples of such plasmid systems are disclosed in, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, PNAS, 97(11):6108-6113; U.S. Published Patent Application No. 20020164770 to Hoffmann; and U.S. Pat. No. 6,544,785 issued Apr. 8, 2003 to Palese, et al. Cells comprising such vectors, as well as cells transduced, transformed, transfected, etc. with such vectors, are also within the current invention.

The invention also encompasses cells comprising at least one above described polynucleotide, or a cleaved or amplified fragment or product thereof. Such cells can optionally express a polypeptide encoded by such polynucleotide. Other embodiments of the invention include vectors (e.g., plasmids, cosmids, phage, viruses, virus fragments, etc.) comprising any of above described polynucleotide. In one embodiment, such vectors are expression vectors.

The invention also encompasses a virus (e.g., an influenza virus) comprising one or more above described polynucleotide (e.g., a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 and optionally encoding a hemagglutinin and/or neuraminidase), or one or more fragments thereof. In one embodiment, such viruses are reassortant/recombinant viruses Immunogenic compositions comprising a reassortant/recombinant virus of the invention are also part of the current invention. In one embodiment, a reassortant virus of the invention is a 6:2 reassortant comprising 6 internal genome segments from one or more donor virus (e.g., a master donor virus or a backbone virus such as A/AA/6/60, B/AA/1/66, A/Puerto Rico/8/34, B/Leningrad/14/17/55, B/14/5/1, B/USSR/60/69, B/Leningrad/179/86, B/Leningrad/14/55, or B/England/2608/76, etc.) and 2 genome segments comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25. In another embodiment, a reassortant virus of the invention is a 7:1 reassortant comprising 6 internal genome segments and 1 hemagglutinine or neuraminidase encoding genome segment from one or more donor virus (e.g., a master donor virus or a backbone virus such as A/AA/6/60, B/AA/1/66, A/Puerto Rico/8/34, B/Leningrad/14/17/55, B/14/5/1, B/USSR/60/69, B/Leningrad/179/86, B/Leningrad/14/55, or B/England/2608/76, etc.) and further comprising 1 genome segment comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25. Reassortant viruses (optionally live viruses) of the invention can include donor viruses that are one or more of, e.g., temperature-sensitive (ts), cold-adapted (ca), or attenuated (au). In one embodiment, reassortant viruses of the invention comprise at least one, at least two, at least three, at least four, at least five or six internal genome segments of any one of A/Ann Arbor/6/60, B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76. In many embodiments, the produced viruses are live viruses (e.g., to be used in vaccines, etc.). Other embodiments include dead or inactivated viruses (e.g., also capable of use in vaccines, etc.). Cells comprising a virus of the invention are also products of the invention.

Methods of producing a reassortant/recombinant influenza virus through culturing a host cell harboring a polynucleotide of the invention are also contemplated. In one embodiment, a method of the invention comprises:

introducing a plurality of vectors comprising polynucleotides corresponding to an influenza virus genome into a population of host cells, which plurality comprises at least 6 internal genome segments of a first influenza strain (e.g., A/AA/6/60, B/AA/1/66, A/PR/8/34, B/Leningrad/14/17/55, B/14/5/1, B/USSR/60/69, B/Leningrad/179/86, B/Leningrad/14/55, or B/England/2608/76), and at least one genome segment comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, and wherein the population of host cells is capable of supporting replication of influenza virus;

culturing the population of host cells; and recovering a plurality of influenza viruses.

In one embodiment, the first influenza strain is cold-adapted and/or temperature sensitive and/or attenuated. In one embodiment, a virus produced by a method of the invention is suitable for administration as part of an intranasal vaccine formulation. In another embodiment, a virus produced by a method of the invention is suitable for administration as killed or inactivated vaccine formulations, live/attenuated non-nasal vaccine formulations, etc. In one embodiment, a virus produced by a method of the invention is an influenza A virus. In one embodiment, a virus produced by a method of the invention is an influenza B virus. Host cells for such methods can optionally comprise, e.g., Vero cells, PerC6 cells, MDCK cells, 293T cells, COS cells, etc. In one embodiment, a method of the invention does not comprise the use of a helper virus. In one embodiment, the plurality of vectors is eight plasmid vectors.

In other embodiments herein, the invention comprises immunogenic compositions having an immunologically effective amount of one or more of the above described reassortant influenza viruses (e.g., a live virus). Other embodiments include methods for stimulating the immune system of an individual to produce a protective immune response against influenza virus comprising administering to the individual an immunologically effective amount of one or more of the reassortant influenza viruses described above (optionally in a physiologically effective carrier).

Other aspects of the invention include methods of producing an isolated or recombinant polypeptide comprising an amino acid sequence selected from SEQ ID NO.: SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26 comprising culturing a host cell comprising a polynucleotide described above in a suitable culture medium under conditions permitting expression of the recombinant polypeptide and, isolating the polypeptide from one or more of the host cell or the medium in which it is grown.

Immunogenic compositions are also features of the invention. For example, immunogenic compositions comprising one or more of the polypeptides (e.g., a polypeptide comprising an amino acid sequence selected from SEQ ID NO.: 2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26) and/or polynucleotides (e.g., a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25) of the invention and, optionally, an excipient such as a pharmaceutically acceptable excipient or one or more pharmaceutically acceptable administration component. In some embodiments, an immunogenic compositions of the invention comprises a reassortant virus of the invention.

Methods of producing an influenza virus vaccine are also included in the invention. For example, the invention includes introducing a plurality of vectors (e.g., plasmid vectors) comprising polynucleotides corresponding to an influenza virus genome (e.g., influenza A or B) into a population of host cells that is capable of supporting replication of such virus, culturing the cells, recovering a plurality of influenza viruses and providing one or more pharmaceutically acceptable excipient with such virus to an individual (e.g., one in need of such treatment). Such viruses can optionally be cold-adapted and/or temperature sensitive and/or attenuated and preferably are suitable for administration in an intranasal vaccine formulation. In one embodiment, the plurality of vectors comprise polynucleotides corresponding to 6 internal genome segments of a first influenza strain (e.g., A/AA/6/60, B/AA/1/66, A/PR/8/34, B/Leningrad/14/17/55, B/14/5/1, B/USSR/60/69, B/Leningrad/179/86, B/Leningrad/14/55, or B/England/2608/76) and one or two genome segments comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 wherein the one or two genome segment optionally encodes an immunogenic influenza surface antigen of a second influenza strain. In one embodiment, a method of the invention comprises: introducing a plurality of vectors comprising polynucleotides corresponding to an influenza virus genome into a population of host cells, which plurality comprises at least 6 internal genome segments of a first influenza strain (e.g., A/AA/6/60, B/AA/1/66, A/PR/8/34, B/Leningrad/14/17/55, B/14/5/1, B/USSR/60/69, B/Leningrad/179/86, B/Leningrad/14/55, or B/England/2608/76), and at least one genome segment comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, and wherein the population of host cells is capable of supporting replication of influenza virus; culturing the population of host cells; and recovering a plurality of influenza viruses.

Methods of producing an immunogenic response in a subject comprising administering of an effective amount of any of the above described viruses to a subject are also within the current invention. Additionally, methods of prophylactic or therapeutic treatment of a viral infection (e.g., viral influenza) in a subject comprising administering one or more above described virus in an amount effective to produce an immunogenic response against the viral infection are also part of the current invention. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that is administered to the subject in an amount effective to prophylactically or therapeutically treat the viral infection.

The invention also comprises compositions of matter having one or more sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, and a selected master donor virus, typically wherein the selected sequence and the master donor virus comprise a 6:2 reassortment, i.e., the HA and NA herein reassorted with the other six influenza genes from the donor virus. Such donor viruses are typically ca, au, is influenza strains. For example, typically donor strains can include, e.g., A/Ann Arbor/6/60, B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76 and variants thereof Those of skill in the art will appreciate that typically donor strains can vary from reassortant to reassortant. Thus, those variations are also encompassed within the current invention. Another element of the invention comprises one or more live attenuated influenza vaccine comprising such compositions, e.g., those having sequences herein reassorted in a 6:2 manner with a selected master donor virus.

Other aspects of the invention include, compositions of matter comprising a hemagglutinin polynucleotide and/or a neuraminidase polynucleotide reassorted with one or more master donor virus, again typically a ca, au, is influenza virus, wherein the polynucleotide comprises a same virus strain as one or more virus strain of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25. Such hemagglutinin and/or neuraminidase polynucleotide is typically determined to be "within the same strain" when it produces a titer that is within a four-fold range of another virus (e.g., ones having the sequences listed herein) as measured by a hemagglutinin inhibition assay. As described below, however, other common assays can also be utilized to determine whether polynucleotides (i.e., viruses comprising such) are within the same strain.

These and other objects and features of the invention will become more fully apparent when the following detailed description is read in conjunction with the accompanying figures and claims.

BRIEF DESCRIPTION OF THE FIGURES

FIG. 1 displays the Sequence Listing of variant hemagglutinin and neuraminidase polynucleotides and polypeptides of the invention.

FIG. 2 displays an alternative organization of variant hemagglutinin and neuraminidase sequences as found in FIG. 1.

DETAILED DESCRIPTION

The present invention includes polypeptide and polynucleotide sequences of influenza hemagglutinin and neuraminidase as well as vectors, viruses, vaccines, compositions and the like comprising such sequences and methods of their use. Additional features of the invention are described in more detail herein.

Definitions

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. Additional terms are defined and described throughout.

As used in this specification and the appended claims, the singular forms "a," "an," and "the" include plural referents unless the context clearly dictates otherwise. Thus, for example, reference to "a virus" includes a plurality of viruses; reference to a "host cell" includes mixtures of host cells, and the like.

The terms "nucleic acid," "polynucleotide," "polynucleotide sequence," and "nucleic acid sequence" refer to single-stranded or double-stranded deoxyribonucleotide or ribonucleotide polymers, chimeras or analogues thereof, or a character string representing such, depending on context. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "nucleic acid" or "polynucleotide" also encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

A "subsequence" is any portion of an entire sequence, up to and including the complete sequence. Typically, a subsequence comprises less than the full-length sequence. A "unique subsequence" is a subsequence that is not found in any previously determined influenza polynucleotide or polypeptide sequence The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

The "neuraminidase" polypeptides of the invention show immunological cross reactivity with one or more known neuraminidase molecule from an influenza virus. The literature is replete with examples of such known neuraminidases (e.g., in GenBank, in publications from the CDC, etc.). Similarly, the "hemagglutinin" polypeptides of the invention show immunological cross-reactivity with one or more known hemagglutinin molecule from an influenza virus. Again, the literature is replete with examples of such known hemagglutinin molecules.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

"Expression of a gene" or "expression of a nucleic acid" typically means transcription of DNA into RNA (optionally including modification of the RNA, e.g., splicing) or transcription of RNA into mRNA, translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

An "amino acid sequence" is a polymer of amino acid residues (a protein, polypeptide, etc.) or a character string representing an amino acid polymer, depending on context.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source. As will be apparent herein, such chimeric viruses are typically reassortant/recombinant viruses. Thus, in some embodiments, a chimera can optionally include, e.g., a sequence (e.g., of HA and/or NA) from an A influenza virus placed into a backbone comprised of, or constructed/derived from a B influenza virus (e.g., B/AA/1/66, etc.) or a B influenza virus sequence placed into an A influenza virus backbone (i.e., donor virus) such as, e.g., A/AA/6/60, etc.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

The term "reassortant," when referring to a virus (typically herein, an influenza virus), indicates that the virus includes genetic and/or polypeptide components derived from more than one parental viral strain or source. For example, a 7:1 reassortant includes 7 viral genome segments (or gene segments) derived from a first parental virus, and a single complementary viral genome segment, e.g., encoding a hemagglutinin or neuraminidase such as those listed in the SEQ ID Tables herein (e.g., SEQ ID NO: 1-28). A 6:2 reassortant includes 6 genome segments, most commonly the 6 internal genome segments from a first parental virus, and two complementary segments, e.g., hemagglutinin and neuraminidase genome segments, from one or more different parental virus. Reassortant viruses can also, depending upon context herein, be termed as "chimeric" and/or "recombinant."

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector or a virus, and supports the replication and/or expression of the nucleic acid. Host cells can be prokaryotic cells such as E. coli, or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc. In other embodiments, host cells can optionally include eggs (e.g., hen eggs, embryonated hen eggs, etc.).

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with wild-type influenza virus. In some instances, the wild-type (e.g., naturally circulating) influenza virus can still cause infection, but it cannot cause a serious or life-threatening infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see Fundamental Immunology, W. E. Paul, ed., Raven Press, N.Y. (1999) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention are variants of influenza HA and/or NA sequences. See, e.g., the Sequence Listing in FIGS. 1 and 2 below. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA). The hemagglutinin molecule consists of a surface glycoprotein and acts to bind to N-AcetylNeuraminic acid (NeuNAc), also known as sialic acid, on host cell surface receptors. In some embodiments herein, the polypeptides of the invention (and polypeptides encoded by the polynucleotides of the invention) can act to bind NeuNAc whether in vitro or in vivo. Such action can in some embodiments also be done by fragments of hemagglutinin which retain hemagglutinin activity. Hemagglutinin is made up of two subunits, HA1 and HA2 and the entire structure is about 550 amino acids in length and about 220 kD. Neuraminidase molecules cleave terminal sialic acid residues from cell surface receptors of influenza virus, thereby releasing virions from infected cells. Neuraminidase also removes sialic acid from newly made hemagglutinin and neuraminidase molecules. In some embodiments herein, the polypeptides of the invention (and polypeptides encoded by the polynucleotides of the invention) can act to cleave sialic acid residues whether in vitro or in vivo. This action can also be done in some embodiments by fragments of neuraminidase which retain neuraminidase activity. The neuraminidase polypeptides of the invention show immunological cross reactivity with one or more known neuraminidase molecule from an influenza virus. The literature is replete with examples of such known neuraminidases (e.g., in GenBank, in publications from the CDC, etc.). Similarly, the hemagglutinin polypeptides of the invention show immunological cross-reactivity with one or more known hemagglutinin molecule from an influenza virus. Again, the literature is replete with examples of such known hemagglutinin molecules.

Influenza is commonly grouped into influenza A and influenza B categories, as well as a typically less important C category. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS 1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza types A and B are typically associated with influenza outbreaks in human populations. However, type A influenza also infects other species as well, e.g., birds, pigs, and other animals. The type A viruses are categorized into subtypes based upon differences within their hemagglutinin and neuraminidase surface glycoprotein antigens. Hemagglutinin in type A viruses has 16 known subtypes and neuraminidase has 9 known subtypes. In humans, currently only about 4 different hemagglutinin and 2 different neuraminidase subtypes are known, e.g., H1, H2, H3, H5, N1, and N2. In particular, two major subtypes of influenza A have been active in humans, namely, H1N1 and H3N2. H1N2, however has recently been of concern. Influenza B viruses are not divided into subtypes based upon their hemagglutinin and neuraminidase proteins. As will be appreciated, the sequences contained within the sequence listing in FIG. 1 comprise a number of different subtypes of influenza. Thus, for example in the sequence listing an A-H3N2 strains are exampled by ca A/Uruguay/716/07 and ca A/Wisconsin/67/05. A-H1N1 strains are shown in ca A/South Dakota/6/07 and ca A/Solomon Islands/3/06, while ca B/Florida/6/04, ca B/Malaysia/2506/04 and ca B/Brisbane/60/2008_DET represent a B-HANA strain.

Different strains of influenza can be categorized based upon, e.g., the ability of influenza to agglutinate red blood cells (RBCs or erythrocytes). Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

Briefly, in typical HI assays, sera to be used for typing or categorization, which is often produced in ferrets, is added to erythrocyte samples in various dilutions, e.g., 2-fold, etc. Optical determination is then made whether the erythrocytes are clumped together (i.e., agglutinated) or are suspended (i.e., non-agglutinated). If the cells are not clumped, then agglutination did not occur due to the inhibition from antibodies in the sera that are specific for that influenza. Thus, the types of influenza are defined as being within the same strain. In some cases, one strain is described as being "like" the other, e.g., strain x is a "y-like" strain, etc. For example, if two samples are within four-fold titer of one another as measured by an HI assay, then they can be described as belonging to the same strain (e.g., both belonging to the "New Caledonia" strain or both being "Moscow-like" strains, etc.). In other words, strains are typically categorized based upon their immunologic or antigenic profile. An HAI titer is typically defined as the highest dilution of a serum that completely inhibits hemagglutination. See, e.g., Schild, et al., Bull. Wld Hlth Org., 1973, 48:269-278, etc. Again, those of skill in the art will be quite familiar with categorization and classification of influenza into strains and the methods to do so.

From the above it will be appreciated that the current invention not only comprises the specific sequences listed herein, but also such sequences within various vectors (e.g., ones used for plasmid reassortment and rescue, see below) as well as hemagglutinin and neuraminidase sequences within the same strains as the sequences listed herein. Also, such same strains that are within various vectors (e.g., typically ones used for plasmid reassortment and rescue such as A/Ann Arbor/6/60 or B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76, etc.) are also included.

As used herein, the term "similar strain" should be taken to indicate that a first influenza virus is of the same or related strain as a second influenza virus. In typical embodiments such relation is commonly determined through use of an HAI assay. Influenza viruses that fall within a four-fold titer of one another in an HAI assay are, thus, of a "similar strain." Those of skill in the art, however, will be familiar with other assays, etc. to determine similar strains, e.g., FRID, neutralization assays, etc. The current invention also comprises such similar strains (i.e., strains similar to the ones present in the sequence listing herein) in the various plasmids, vectors, viruses, methods, etc. herein. Thus, unless the context clearly dictates otherwise, descriptions herein of particular sequences (e.g., those in the sequence listing) or fragments thereof also should be considered to include sequences from similar strains to those (i.e., similar strains to those strains having the sequences in those plasmids, vectors, viruses, etc. herein). Also, it will be appreciated that the NA and HA polypeptides within such similar strains are, thus, "similar polypeptides" when compared between "similar strains."

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (as in the current invention) are quite useful in constructing influenza vaccines.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and NA sequences herein. See, U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus." Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 or B/Ann Arbor/1/66 or A/Puerto Rico/8/34, or B/Leningrad/14/17/55, B/14/5/1, B/USSR/60/69, B/Leningrad/179/86, B/Leningrad/14/55, or B/England/2608/76 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as A/Puerto Rico/8/34, etc., containing the other influenza genes present in a reassortant, namely, the non-HA and non-NA genes). Live, attenuated influenza A virus vaccines against human influenza viruses were recently licensed in the United States. See above. Such vaccines are reassortant H1N1 and H1N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). In some embodiments herein, the reassortants can also comprise 7:1 reassortants. In other words, only the HA or the NA is not from the backbone or MDV strain. Previous work has been reported with suitable backbone donor virus strains that optionally are within various embodiments of the current invention. See, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Maassab et al., J. of Inf. Dis., 1982, 146:780-790; Cox, et al., Virology, 1988, 167:554-567; Wareing et al., Vaccine, 2001, 19:3320-3330; Clements, et al., J Infect Dis., 1990, 161(5):869-77, etc.

In some embodiments, the sequences herein can optionally have specific regions removed (both or either in the nucleic acid sequence or the amino acid sequence). For example, for those molecules having a polybasic cleavage site, such sites can optionally be removed. Such cleavage sites, in some embodiments herein, are, e.g., modified or altered in their sequences in comparison to the wild-type sequences from which such sequences are derived (e.g., to disable the cleavage or reduce the cleavage there, etc.). Such modifications/alterations can be different in different strains or sequences due to the various sequences of the cleavage sites in the starting sequences. For example, 4 polybasic residues (RRKK (SEQ ID NO: 29)) are typically removed in some HA sequences. (as compared to wt). In various embodiments, such polybasic cleavage sites can be modified in a number of ways (all of which are contained within the invention). For example, the polybasic cleavage site can be removed one amino acid at a time (e.g., one R removed, two Rs removed, RRK removed, or RRKK (SEQ ID NO: 29) removed). Additionally, an amino acid residue directly upstream of the cleavage site can also be removed or altered (e.g., from an R to a T, etc.); also, the nucleotides encoding the amino acid residue directly after the cleavage site can also be modified. Those of skill in the art will be familiar with various methods of removing such specific regions. The resulting shortened sequences are also contained within the current invention. See, e.g., Li et al., J. of Infectious Diseases, 179:1132-8, 1999.

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Thus, the present invention can utilize growth, e.g., in appropriate culture conditions, of virus strains (both A strain and B strain influenza viruses) with desirable properties relative to vaccine production (e.g., attenuated pathogenicity or phenotype, cold adaptation, temperature sensitivity, etc.) in vitro in cultured cells. Influenza viruses can be produced by introducing a plurality of vectors incorporating cloned viral genome segments into host cells, and culturing the cells at a temperature not exceeding 35° C. When vectors including an influenza virus genome are transfected, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain such as those in the sequence listing herein, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

In such embodiments, typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively, as well as others mentioned throughout.

For example, a selected master donor type A virus (MDV-A), or master donor type B virus (MDV-B), is produced from a plurality of cloned viral cDNAs constituting the viral genome. Embodiments include those wherein recombinant viruses are produced from eight cloned viral cDNAs. Eight viral cDNAs representing either the selected MDV-A or MDV-B sequences of PB2, PB1, PA, NP, HA, NA, M and NS are optionally cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site (also known as a polybasic cleavage site)).

Infectious recombinant MDV-A or MDV-B virus can be then recovered following transfection of plasmids bearing the eight viral cDNAs into appropriate host cells, e.g., Vero cells, co-cultured MDCK/293T or MDCK/COS7 cells. Using the plasmids and methods described herein and, e.g., in U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, PNAS, 97(11):6108-6113; U.S. Published Patent Application No. 20020164770 to Hoffmann; and U.S. Pat. No. 6,544,785 issued Apr. 8, 2003 to Palese, et al., the invention is useful, e.g., for generating 6:2 reassortant influenza vaccines by co-transfection of the 6 internal genes (PB1, PB2, PA, NP, M and NS) of the selected virus (e.g., MDV-A, MDV-B) together with the HA and NA derived from different corresponding type (A or B) influenza viruses e.g., as shown in the sequence listings herein. For example, the HA segment is favorably selected from a pathogenically relevant H1, H3 or B strain, as is routinely performed for vaccine production. Similarly, the HA segment can be selected from a strain with emerging relevance as a pathogenic strain such as those in the sequence listing herein. Reassortants incorporating seven genome segments of the MDV and either the HA or NA gene of a selected strain (7:1 reassortants) can also be produced. It will be appreciated, and as is detailed throughout, the molecules of the invention can optionally be combined in any desired combination. For example, the HA and/or NA sequences herein can be placed, e.g., into a reassortant backbone such as A/AA/6/60, B/AA/1/66, A/Puerto Rico/8/34 (i.e., PR8), etc., in 6:2 reassortants or 7:1 reassortants, etc. Thus, as explained more fully below, there would be 6 internal genome segments from the donor virus (again, e.g., A/AA/6/60, etc.) and 2 genome segments from a second strain (e.g., a wild-type strain, not the donor virus). Such 2 genome segments are preferably the HA and NA genes. A similar situation arises for 7:1 reassortants, in which however, there are 7 genome segments from the donor virus and 1 genome segment (either HA or NA) from a different virus (typically wild-type or one to which an immune response is desired). Also, it will be appreciated that the sequences herein (e.g., those in the sequence listing of FIG. 1, etc.) can be combined in a number of means in different embodiments herein. Thus, any of the sequences herein can be present singularly in a 7:1 reassortant (i.e., the sequence of the invention present with 7 donor virus genome segments) and/or can be present with another sequence of the invention in a 6:2 reassortant. Within such 6:2 reassortants, any of the sequences of the invention can optionally be present with any other sequence of the invention. Typical, and preferred, embodiments comprise HA and NA from the same original wild-type strains however (or modified wild-type strains such as those with modified polybasic cleavage sites). For example, typical embodiments can comprise a 6:2 reassortant having 6 internal genome segments from a donor virus such as A/AA/6/60 and the HA and NA genome segments from the same strain such as ca A/Uruguay/716/07, ca A/South Dakota/6/07, ca A/Wisconsin/67/05 or ca A/Solomon Islands/3/06. In another embodiment, a 6:2 reassortant described herein may comprise 6 internal genome segments from a donor virus such as B/Ann Arbor/1/66 and the HA and NA genome segments from the same strain such as ca B/Florida/6/04, ca B/Malaysia/2506/04 or ca B/Brisbane/60/2008_DET. Of course, it will again be appreciated that the invention also includes such reassortant viruses wherein the HA and NA genome segments are from similar strains (i.e., strains that are similar strains to influenza strains having the sequences found in SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25. The above references are specifically incorporated herein in their entirety for all purposes, e.g., especially for their teachings regarding plasmids, plasmid rescue of virus (influenza virus), multi-plasmid systems for virus rescue/production, etc.

Again, the HA and NA sequences of the current invention are optionally utilized in such plasmid reassortment vaccines (and/or in other ts, cs, ca, and/or att viruses and vaccines).

However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., the sequences of the invention).

FluMist™

As mentioned previously, numerous examples and types of influenza vaccine exist. An exemplary influenza vaccine is FluMist™ (MedImmune Vaccines Inc., Mt. View, Calif.) which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial* JAMA 282:137-44). In typical, and preferred, embodiments, the methods and compositions of the current invention are preferably adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the wild-type strains to which the vaccine is addressed (or, in some instances, to related strains) along with six gene segments, PB1, PB2, PA, NP, M and NS, from a common master donor virus (MDV). The HA and NA sequences herein, thus, are optionally part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C.* Nature 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines* Viral Immunol 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children* N Engl J Med 338:1405-12; Boyce et al. (2000) *Safety and immunogenicity of adjuvanted and unadjuvanted subunit influenza vaccines administered intranasally to healthy adults* Vaccine 19:217-26; Edwards et al. (1994) *A randomized controlled trial of cold adapted and inactivated vaccines for the prevention of influenza A disease* J Infect Dis 169:68-76; Nichol et al. (1999) *Effectiveness of live, attenuated intranasal influenza virus vaccine in healthy, working adults: a randomized controlled trial* JAMA 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets* J. Infect. Dis. 146:780-900).

Production of such reassorted virus using B strains of influenza is more difficult, however, recent work (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus") has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences, methods, etc. of the current invention, are optionally used in conjunction with, or in combination with, such previous work involving, e.g., reassorted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO:1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or polypeptides of SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10, residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26, or similar strains of the virus sequences within SEQ ID NO:1-28, or fragments of any of the previous) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hen eggs (i.e., normal allantoic fluid or NAF), or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., an HA and/or an NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., Infect. Immun 37:397-400 (1982); Kim et al., Pediatrics 52:56-63 (1973); and Wright et al., J. Pediatr. 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, F1t3 ligand, B7.1; B7.2, etc. The immunostimulatory molecules can be administered in the same formulation as the influenza viruses, or can be administered separately. Either the protein (e.g., an HA and/or NA polypeptide of the invention) or an expression vector encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences, e.g., as described herein. Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two, at least three, or at least four influenza virus strains or substrains, e.g., at least two of which may represent a different subgroup. For example, vaccinating an individual with at least four strains or substrains of attenuated influenza virus may include vaccinating the individual with at least two strains or substrains of influenza A virus and at least two strains or substrains of influenza B virus. Vaccinating the individual with the at least four strains or substrains of attenuated influenza virus may include vaccinating the individual with at least three strains or substrains of influenza A virus and at least one strain or substrain of influenza B virus. The vaccination of the individual with at least four influenza virus strains or substrains may require administration of a single tetravalent vaccine which comprises all of the at least four attenuated influenza virus strains or substrains. The vaccination may alternatively require administration of multiple vaccines, each of which comprises one, two, or three of the attenuated influenza virus strains or substrains. Additionally, vaccine combinations can optionally include mixes of pandemic vaccines and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents. In one embodiment, a vaccine of the invention is a trivalent vaccine comprising three reassortant influenza viruses. In one embodiment, a vaccine of the invention is a trivalent vaccine comprising two reassortant influenza A viruses and a reassortant influenza B virus. In one embodiment, a vaccine of the invention is a trivalent vaccine comprising a reassortant influenza A virus of the H1 type, a reassortant influenza A virus of the H3 type and a reassortant influenza B virus. In another embodiment, a vaccine of the invention is a tetravalent vaccine comprising four reassortant influenza viruses. In one embodiment, a vaccine of the invention is a tetravalent vaccine comprising two reassortant influenza A viruses and two reassortant influenza B viruses. In one embodiment, a vaccine of the invention is a tetravalent vaccine comprising a reassortant influenza A virus of the H1 type, a reassortant influenza A virus of the H3 type, a reassortant influenza B virus of the Victoria lineage and a reasortant influenza B virus of the Yamagata lineage.

Polynucleotides of the Invention

Probes

The HA and NA polynucleotides of the invention, e.g., as shown in the sequences herein such as SEQ ID NO:1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, and fragments thereof, are optionally used in a number of different capacities alternative to, or in addition to, the vaccines described above. Other exemplary uses are described herein for illustrative purpose and not as limitations on the actual range of uses, etc. Different methods of construction, purification, and characterization of the nucleotide sequences of the invention are also described herein.

In some embodiments, nucleic acids including one or more polynucleotide sequence of the invention are favorably used as probes for the detection of corresponding or related nucleic acids in a variety of contexts, such as in nucleic hybridization experiments, e.g., to find and/or characterize homologous influenza variants (e.g., homologues to sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a polynucleotide sequence or subsequence selected, e.g., from among SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, or sequences complementary thereto. Alternatively, polynucleotide sequences that are variants of one of the above-designated sequences are used as probes. Most typically, such variants include one or a few conservative nucleotide variations. For example, pairs (or sets) of oligonucleotides can be selected, in which the two (or more) polynucleotide sequences are conservative variations of each other, wherein one polynucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of, e.g., SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite triester method described by Beaucage and Caruthers (1981) Tetrahedron Letts 22(20):1859-1862, e.g., using an automated synthesizer, or as described in Needham-Van Devanter et al. (1984) Nucl Acids Res, 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) J Chrom 255:137-149. The sequence of the synthetic oligonucleotides can be verified using the chemical degradation method of Maxam and Gilbert (1980) in Grossman and Moldave (eds.) Academic Press, New York, Methods in Enzymology 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention and/or encoded by polynucleotide sequences of the invention, e.g., selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, are favorably used to identify and isolate antibodies, e.g., from phage display libraries, combinatorial libraries, polyclonal sera, and the like.

Antibodies specific for any a polypeptide sequence or subsequence, e.g., of SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26, and/or encoded by polynucleotide sequences of the invention, e.g., selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Antibodies against specific amino acids sequences described herein (e.g., SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26) are also useful in determining whether other influenza viruses are within the same strain as the current sequences (e.g., through an HI assay, etc.). Additional details regarding production of specific antibodies are provided below.

Diagnostic Assays

The nucleic acid sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as influenza RNA in clinical specimens.

The probes of the invention, e.g., as exemplified by unique subsequences selected from, e.g., SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to nucleic acids originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the nucleic acid sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25, or a subsequence thereof etc., has been inserted, in a forward or reverse orientation. For example, the inserted nucleic acid can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or hemagglutinin or neuraminidase fragments). Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, E. coli lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Various embodiments of the current invention can comprise a number of different vector constructions. Such constructions are typically and preferably used in plasmid rescue systems to create viruses for use in vaccines (e.g., in live attenuated vaccines, in killed or inactivated vaccines, etc.). Thus, the invention includes recombinant DNA molecules having a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of a mRNA coding sequence of a negative strand RNA virus. Also, the invention includes a recombinant DNA molecule that, upon transcription yields an RNA template that contains an RNA sequence comprising the reverse complement of an mRNA coding sequence of a negative strand RNA virus, and vRNA terminal sequences. The invention also includes a recombinant DNA molecule that upon transcription yields a replicable RNA template comprising the reverse complement of an mRNA coding sequence of a negative strand RNA virus. Such above recombinant DNA molecules typically involve wherein the negative strand RNA virus is influenza (e.g., influenza A or B, etc.). Also, the RNA molecule in such embodiments is typically an influenza genome segment and the RNA template is typically an influenza genome segment. The recombinant DNA molecules typically comprise wherein the RNA template is replicable, wherein the negative strand RNA virus is influenza, and wherein the RNA template is an influenza genome segment. Thus, the nucleic acids influenza segments typically comprise HA and/or NA genes (the corresponding nucleic acid of which is, e.g., in FIG. 1, or within similar strains of the strains having the nucleic acids in, e.g., FIG. 1.

The invention also includes methods of preparing an RNA molecule comprising transcribing a recombinant DNA molecule with a DNA-directed RNA polymerase, wherein the DNA molecule comprises a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of an mRNA coding sequence of a negative strand RNA virus. The invention also includes a method of preparing an RNA molecule comprising transcribing a recombinant DNA molecule with a DNA-directed RNA polymerase, wherein the recombinant DNA molecule yields upon transcription an RNA molecule that contains an RNA sequence comprising the reverse complement of an mRNA coding sequence of a negative strand RNA virus, and vRNA terminal sequences. Furthermore, the invention includes a method of preparing an RNA molecule comprising transcribing a recombinant DNA molecule with a DNA-directed RNA polymerase, wherein the recombinant DNA molecule yields upon transcription a replicable RNA molecule comprising the reverse complement of an mRNA coding sequence of a negative strand RNA virus. Such methods typically comprise wherein the negative strand RNA virus is influenza, and wherein the RNA molecule is an influenza genome segment. Such methods preferably include wherein the DNA-directed RNA polymerase is pol I, pol II, T7 polymerase, T3 polymerase, or Sp6 polymerase. Thus, again, the influenza nucleic acid segments typically comprise HA and/or NA genes as described throughout.

Other methods within the invention include methods of constructing a DNA molecule comprising a transcription control element that binds a DNA-directed RNA polymerase that is operatively linked to a DNA sequence that encodes an RNA molecule, wherein the RNA molecule comprises a binding site specific for an RNA-directed RNA polymerase of an influenza virus, operatively linked to an RNA sequence comprising the reverse complement of an mRNA coding sequence of an influenza virus, wherein the DNA sequence comprises a nucleic acid corresponding to one or more of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof or of one or more nucleic acid sequence of a similar strain (e.g., a strain similar to such strains having the sequences found in the sequences of FIG. 1, etc.). Also, the invention includes a method of constructing a DNA molecule comprising a DNA sequence that upon transcription yields an RNA template that contains an RNA sequence comprising the reverse complement of an mRNA coding sequence of an influenza virus, and vRNA terminal sequences, wherein the DNA sequence comprises a nucleic acid corresponding to one or more of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof, or of one or more nucleic acid of a similar strain (e.g., a strain similar to such strains that have the sequences found in FIG. 1, etc.). Such methods also include wherein the RNA template is replicable. Other methods of the invention include those of constructing a DNA molecule comprising a DNA sequence that upon transcription yields a replicable RNA template comprising the reverse complement of an mRNA coding sequence of an influenza virus. These methods of the invention typically include wherein the RNA molecule is an influenza genome segment, wherein the DNA-directed RNA polymerase is pol I, pol II, T7 polymerase, T3 polymerase, or Sp6 polymerase.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) Heat stress promoters and transcription factors Results Probl Cell Differ 20:125-62; Kriegler et al. (1990) *Assembly of enhancers, promoters, and splice signals to control expression of transferred genes* Methods in Enzymol 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate nucleic acid sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortment. See, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, PNAS, 97(11):6108-6113; U.S. Published Patent Application No. 20020164770 to Hoffmann; and U.S. Pat. No. 6,544,785 issued Apr. 8, 2003 to Palese, et al. The reassortants produced can include the HA and NA genes arranged with the 6 other influenza genes from the A/Ann Arbor/6/60 donor strain, the B/Ann Arbor/1/66 donor strain (and/or derivatives and modifications thereof), the A/Puerto Rico/8/34 donor strain, etc.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a nucleic acid sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) Results Probl Cell Differ 20:125-62; Bittner et al. (1987) Methods in Enzymol 153:516-544).

Production of Recombinant Virus

Negative strand RNA viruses can be genetically engineered and recovered using a recombinant reverse genetics approach (U.S. Pat. No. 5,166,057 to Palese et al.). Such method was originally applied to engineer influenza viral genomes (Luytjes et al. (1989) Cell 59:1107-1113; Enami et al. (1990) Proc. Natl. Acad. Sci. USA 92:11563-11567), and has been successfully applied to a wide variety of segmented and nonsegmented negative strand RNA viruses, e.g., rabies (Schnell et al. (1994) EMBO J. 13: 4195-4203); VSV (Lawson et al. (1995) Proc. Natl. Acad. Sci. USA 92: 4477-4481); measles virus (Radecke et al.(1995) EMBO J. 14:5773-5784); rinderpest virus (Baron & Barrett (1997) J. Virol. 71: 1265-1271); human parainfluenza virus (Hoffman & Banerjee (1997) J. Virol. 71: 3272-3277; Dubin et al. (1997) Virology 235:323-332); SV5 (He et al. (1997) Virology 237:249-260); canine distemper virus (Gassen et al. (2000) J. Virol. 74:10737-44); and Sendai virus (Park et al. (1991) Proc. Natl. Acad. Sci. USA 88: 5537-5541; Kato et al. (1996) Genes to Cells 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention. Of course, as will be appreciated by those of skill in the art, influenza viruses in general (and those of the invention as well) are negative stranded RNA viruses. Thus, when the present invention describes influenza viruses as comprising, e.g., the sequences of FIG. 1, etc., it is to be understood to typically mean the corresponding negative stranded RNA version of the sequences. The nucleotide sequences in FIG. 1 comprise DNA versions (e.g., coding plus sense, etc.) of the genes (along with some untranslated regions in the nucleotide sequences). Those of skill in the art can easily convert between RNA and DNA sequences (e.g., changing U to T, etc.), and between complementary nucleotide sequences (whether RNA or DNA),etc. Thus, for example, those of skill in the art can easily convert from a nucleotide sequence (e.g., one given in FIG. 1 such as SEQ ID NO:1) to the corresponding amino acid sequence or to a corresponding complementary sequence (whether DNA or RNA), etc. Also, as will be evident, when such HA and/or NA sequences are described within DNA vectors, e.g., plasmids, etc., then the corresponding DNA version of the sequences are typically to be understood. Again, nucleic acids of the invention include the explicit sequences in the sequence listings herein, as well as the complements of such sequences (both RNA and DNA), the double stranded form of the sequences in the sequence listings, the corresponding RNA forms of the sequences in the sequence listings (either as the RNA complement to the explicit sequence in the sequence listing or as the RNA version of the sequence in the sequence listing, e.g., of the same sense, but comprised of RNA, with U in place of T, etc.). Thus, depending on context herein, the nucleic acid sequences of the invention can comprise the RNA versions of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 (either in positive stranded sense or in negative stranded sense).

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda*.

Most commonly, mammalian cells are used to culture the HA and NA molecules of the invention. Suitable host cells for the replication of influenza virus (e.g., with the HA and/or NA sequences herein) include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences, e.g., through production of viruses. The culture conditions, such as temperature, pH and the like, are typically those previously used with the particular host cell selected for expression, and will be apparent to those skilled in the art and in the references cited herein, including, e.g., Freshney (1994) Culture of Animal Cells, a Manual of Basic Technique, $3^{rd}$ edition, Wiley-Liss, New York and the references cited therein. Other helpful references include, e.g., Paul (1975) Cell and Tissue Culture, $5^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. in Cohen and Shafferman (eds.) Novel Strategies in Design and Production of Vaccines, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface.

For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 µg of each vector is introduced into a population of host cells with approximately 2 µl of TransIT-LT1 diluted in 160 µl medium, preferably serum-free medium, in a total volume of 200 µl. The DNA:transfection reagent mixtures are incubated at room temperature for 45 minuets followed by addition of 800 µl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 µl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 µl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) Proc Natl Acad Sci 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) J Biol Chem 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); Methods in Enzymology 153: 516-544.

Nucleic Acid Hybridization

Comparative hybridization can be used to identify nucleic acids of the invention, including conservative variations of nucleic acids of the invention. This comparative hybridization method is a preferred method of distinguishing nucleic acids of the invention. In addition, target nucleic acids which hybridize to the nucleic acids represented by, e.g., SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 5x-10x as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Tech-* niques in Biochemistry and Molecular Biology—Hybridization with Nucleic Acid Probes part I chapter 2, "Overview of principles of hybridization and the strategy of nucleic acid probe assays," (Elsevier, N.Y.), as well as in Ausubel, Sambrook, and Berger and Kimmel, all below. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., Molecular Biomethods Handbook (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid, is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., Nature Biotechnology, 19:456-460 (2001); Ling et al., *Approaches to DNA mutagenesis: an overview*, Anal Biochem 254(2): 157-178 (1997); Dale et al., *Oligonucleotide-directed random mutagenesis using the phosphorothioate method*, Methods Mol Biol 57:369-374 (1996); I. A. Lorimer, I. Pastan, Nucleic Acids Res 23, 3067-8 (1995); W. P. C. Stemmer, Nature 370, 389-91 (1994); Arnold, *Protein engineering for unusual environments*, Current Opinion in Biotechnology 4:450-455 (1993); Bass et al., *Mutant Trp repressors with new DNA-binding specificities*, Science 242:240-245 (1988); Fritz et al., *Oligonucleotide-directed construction of mutations: a gapped duplex DNA procedure without enzymatic reactions in vitro*, Nucl Acids Res 16: 6987-6999 (1988); Kramer et al., *Improved enzymatic in vitro reactions in the gapped duplex DNA approach to oligonucleotide-directed construction of mutations*, Nucl Acids Res 16: 7207 (1988); Sakamar and Khorana, *Total synthesis and expression of a gene for the a-subunit of bovine rod outer segment guanine nucleotide-binding protein (transducin)*, Nucl Acids Res 14: 6361-6372 (1988); Sayers et al., *Y-T Exonucleases in phosphorothioate-based oligonucleotide-directed mutagenesis*, Nucl Acids Res 16:791-802 (1988); Sayers et al., *Strand specific cleavage of phosphorothioate-containing DNA by reaction with restriction endonucleases in the presence of ethidium bromide*, (1988) Nucl Acids Res 16: 803-814; Carter, *Improved oligonucleotide-directed mutagenesis using M13 vectors*, Methods in Enzymol 154: 382-403 (1987); Kramer & Fritz *Oligonucleotide-directed construction of mutations via gapped duplex DNA*, Methods in Enzymol 154:350-367 (1987); Kunkel, *The efficiency of oligonucleotide directed mutagenesis*, in Nucleic Acids & Molecular Biology (Eckstein, F. and Lilley, D. M. J. eds., Springer Verlag, Berlin)) (1987); Kunkel et al., *Rapid and efficient site-specific mutagenesis without phenotypic selection*, Methods in Enzymol 154, 367-382 (1987); Zoller & Smith, *Oligonucleotide-directed mutagenesis: a simple method using two oligonucleotide primers and a single-stranded DNA template*, Methods in Enzymol 154: 329-350 (1987); Carter, *Site-directed mutagenesis*, Biochem J 237:1-7 (1986); Eghtedarzadeh & Henikoff, *Use of oligonucleotides to generate large deletions*, Nucl Acids Res 14: 5115 (1986); Mandecki, *Oligonucleotide-directed double-strand break repair in plasmids of Escherichia coli: a method for site-specific mutagenesis*, Proc Natl Acad Sci USA, 83:7177-7181 (1986); Nakamaye & Eckstein, *Inhibition of restriction endonuclease Nci I cleavage by phosphorothioate groups and its application to oligonucleotide-directed mutagenesis*, Nucl Acids Res 14: 9679-9698 (1986); Wells et al., *Importance of hydrogen-bond formation in stabilizing the transition state of subtilisin*, Phil Trans R Soc Lond A 317: 415-423 (1986); Botstein & Shortle, *Strategies and applications of in vitro mutagenesis*, Science 229:1193-1201(1985); Carter et al., *Improved oligonucleotide site-directed mutagenesis using M13 vectors*, Nucl Acids Res 13: 4431-4443 (1985); Grundström et al., *Oligonucleotide-directed mutagenesis by microscale 'shot-gun' gene synthesis*, Nucl Acids Res 13: 3305-3316 (1985); Kunkel, *Rapid and efficient site-specific mutagenesis without phenotypic selection*, Proc Natl Acad Sci USA 82:488-492 (1985); Smith, *In vitro mutagenesis*, Ann Rev Genet 19:423-462(1985); Taylor et al., *The use of phosphorothioate-modified DNA in restriction enzyme reactions to prepare nicked DNA*, Nucl Acids Res 13: 8749-8764 (1985); Taylor et al., *The rapid generation of oligonucleotide-directed mutations at high frequency using phosphorothioate-modified DNA*, Nucl Acids Res 13: 8765-8787 (1985); Wells et al., *Cassette mutagenesis: an efficient method for generation of multiple mutations at defined sites*, Gene 34:315-323 (1985); Kramer et al., *The gapped duplex DNA approach to oligonucleotide-directed mutation construction*, Nucl Acids Res 12: 9441-9456 (1984); Kramer et al., *Point Mismatch Repair*, Cell 38:879-887 (1984); Nambiar et al., *Total synthesis and cloning of a gene coding for the ribonuclease S protein*, Science 223: 1299-1301 (1984); Zoller & Smith, *Oligonucleotide-directed mutagenesis of DNA fragments cloned into M13 vectors*, Methods in Enzymol 100:468-500 (1983); and Zoller & Smith, *Oligonucleotide-directed mutagenesis using M13-derived vectors: an efficient and general procedure for the production of point mutations in any DNA fragment*, Nucl Acids Res 10:6487-6500 (1982). Additional details on many of the above methods can be found in Methods in Enzymol Volume 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, Tetrahedron Letts 22(20):1859-1862, (1981) e.g., using an automated synthesizer, as described in Needham-VanDevanter et al., Nucleic Acids Res, 12:6159-6168 (1984).

In addition, essentially any nucleic acid can be custom or standard ordered from any of a variety of commercial sources, such as The Midland Certified Reagent Company (see website for The Midland Certified Reagent Company), The Great American Gene Company (see website for The Great American Gene Company), ExpressGen Inc. (see website for ExpressGen Inc.), Operon Technologies Inc. (Alameda, CA) and many others. Similarly, peptides and antibodies can be custom ordered from any of a variety of sources, such as PeptidoGenic (available at the website for PeptidoGenic), HTI Bio-products, Inc. (see website for HTI Bio-products, Inc.), BMA Biomedicals Ltd. (U.K.), Bio.Synthesis, Inc., and many others.

The present invention also relates to host cells and organisms comprising a HA and/or NA molecule or other polypeptide and/or nucleic acid of the invention or such HA and/or NA or other sequences within various vectors such as 6:2 reassortant influenza viruses, plasmids in plasmid rescue systems, etc. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., Proc Natl Acad Sci USA 82, 5824 (1985), infection by viral vectors, high velocity ballistic penetration by small particles with the nucleic acid either within the matrix of small beads or particles, or on the surface (Klein et al., Nature 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, Gene 8:81 (1979); Roberts, et al., Nature, 328:731 (1987); Schneider, B., et al., Protein Expr Purif 6435:10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are also found in Watson et al. (1992) Recombinant DNA Second Edition Scientific American Books, NY. See, above.

Polypeptide Production and Recovery

In some embodiments, following transduction of a suitable host cell line or strain and growth of the host cells to an appropriate cell density, a selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing one or more HA and/or NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules, or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) Bioseparation of Proteins, Academic Press, Inc.; and Bollag et al. (1996) Protein Methods, $2^{nd}$ Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice $3^{rd}$ Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds.) Textbook of Influenza pp. 324-332; Merten et al. (1996) *Production of influenza virus in cell cultures for vaccine preparation*, in Cohen & Shafferman (eds.) Novel Strategies in Design and Production of Vaccines pp. 141-151, and U.S. Pat. No. 5,690,937. If desired, the recovered viruses can be stored at −80° C. in the presence of sucrose-phosphate-glutamate (SPG) as a stabilizer Alternatively, cell-free transcription/translation systems can be employed to produce polypeptides comprising an amino acid sequence or subsequence of, e.g., SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26, or encoded by the polynucleotide sequences of the invention. A number of suitable in vitro transcription and translation systems are commercially available. A general guide to in vitro transcription and translation protocols is found in Tymms (1995) In vitro Transcription and Translation Protocols: Methods in Molecular Biology Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) Solid-Phase Peptide Synthesis, WH Freeman Co, San Francisco; Merrifield J (1963) J Am Chem Soc 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc. Amino acid(s) are modified, for example, co-translationally or post-translationally during recombinant production (e.g., N-linked glycosylation at N—X—S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) Protein Protocols on CD-ROM Human Press, Towata, N.J.

Fusion Proteins

The present invention also provides fusion proteins comprising fusions of the sequences of the invention (e.g., encoding HA and/or NA polypeptides) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof Antibodies specific for the above mentioned polypeptides are useful, e.g., for diagnostic and therapeutic purposes, e.g., related to the activity, distribution, and expression of target polypeptides. For example, such antibodies can optionally be utilized to define other viruses within the same strain(s) as the HA/NA sequences herein.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) Current Protocols in Immunology Wiley/Greene, NY; Paul (ed.) (1998) Fundamental Immunology, Fourth Edition, Lippincott-Raven, Lippincott Williams & Wilkins; Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) Science 246: 1275-1281; and Ward, et al. (1989) Nature 341: 544-546. Specific monoclonal and polyclonal antibodies and antisera will usually bind with a $K_D$ of, e.g., at least about 0.1 µM, at least about 0.01 µM or better, and, typically and at least about 0.001 µM or better.

For certain therapeutic applications, humanized antibodies are desirable. Detailed methods for preparation of chimeric (humanized) antibodies can be found in U.S. Pat. No. 5,482, 856. Additional details on humanization and other antibody production and engineering techniques can be found in Borrebaeck (ed.) (1995) Antibody Engineering, $2^{nd}$ Edition Freeman and Company, NY (Borrebaeck); McCafferty et al. (1996) Antibody Engineering, A Practical Approach IRL at Oxford Press, Oxford, England (McCafferty), and Paul (1995) Antibody Engineering Protocols Humana Press, Towata, N.J. (Paul). Additional details regarding specific procedures can be found, e.g., in Ostberg et al. (1983), Hybridoma 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein such as in SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26, etc. To eliminate cross-reactivity with other homologues, the antibody or antisera is subtracted with the HA and/or NA molecules found in public databases at the time of filing, e.g., the "control" polypeptide(s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein, etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) Antibodies, A Laboratory Manual, Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about ½ signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide(s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2x the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein. However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variation" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

Conservative Substitution Groups

| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein (e.g., SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25). The unique subsequence is unique as compared to a nucleic acids corresponding to nucleic acids such as, e.g., those found in GenBank or other similar public databases at the time of filing (e.g., other known or characterized hemagglutinin and/or neuraminidase nucleic acid molecules). Alignment can be performed using, e.g., BLAST set to default parameters. Any unique subsequence is useful, e.g., as a probe to identify the nucleic acids of the invention. See, above.

Similarly, the invention includes a polypeptide (e.g., from SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26) which comprises a unique subsequence in a polypeptide selected from the sequence of HA and NA molecules disclosed herein. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above. The polynucleotides of the invention also comprise RNA (both positive sense and negative sense) versions of the sequences of the sequence listing. See above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs and/or RNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, more preferably over a region of at least about 250 residues, and most preferably the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared when the amino acids are hemagglutinin or hemagglutinin fragments or which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; over at least about 470 amino acids; or over at least about 566 amino acids contiguous when the amino acid is neuraminidase or a neuraminidase fragment.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, Proc Natl Acad Sci USA 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (see website for the National Center for Biotechnology Information). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) Proc Natl Acad Sci USA 89:10915).

In addition to calculating percent sequence identity, the BLAST algorithm also performs a statistical analysis of the similarity between two sequences (see, e.g., Karlin & Altschul, Proc Natl Acad Sci USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple nucleic acid, or amino acid, sequence alignments is the CLUSTALW program (Thompson, J. D. et al. (1994) Nucl. Acids. Res. 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) Proc. Natl. Acad. Sci. USA 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof Integrated systems can further include, e.g., gene synthesis equipment for making genes corresponding to the character strings.

Various methods known in the art can be used to detect homology or similarity between different character strings (see above), or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among four principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential gene expression, or other operations.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit typically further comprises, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like. Furthermore, the kits can comprise various vaccines (e.g., produced through plasmid rescue protocols) such as live attenuated vaccine (e.g., FluMist™) comprising the HA and/or NA sequences herein.

To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

Specific Embodiments

1. An isolated or recombinant polypeptide, which polypeptide is selected from the group consisting of:
   a) a polypeptide comprising an amino acid sequence encoded by a nucleotide sequence selected from SEQ ID NO: 1, 3, 5, 7, 9, 11, 13, 15, 17, 19, 21, 23, 25 and 27;
   b) a polypeptide comprising an amino acid sequence encoded by a nucleotide sequence selected from residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25;

c) a polypeptide comprising an amino acid sequence selected from SEQ ID NO: 2, 4, 6, 8, 10, 12, 14, 16, 18, 20, 22, 24, 26 and 28;

d) a polypeptide comprising an amino acid sequence selected from residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26;and, e) a polypeptide comprising an amino acid sequence selected from SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26 in which one, two, three, four, five, six, seven, eight, nine, ten, eleven, twelve, thirteen, fourteen or fifteen amino acid residues were substituted, inserted or deleted.

2. An isolated or recombinant polypeptide comprising a hemagglutinin or a fragment thereof, the polypeptide comprising an amino acid sequence which is substantially identical over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids contiguous of one or more polypeptide, which polypeptide is selected from the group consisting of:

a) a polypeptide comprising an amino acid sequence encoded by a nucleotide sequence selected from SEQ ID NO:1, 5, 9, 13, 17, 21 and 25; and b) a polypeptide comprising the amino acid sequence selected from SEQ ID NO:2, 6, 10, 14, 18, 22 and 26.

3. An isolated or recombinant polypeptide comprising a neuraminidase or a fragment thereof, the polypeptide comprising an amino acid sequence which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; or over at least about 470 amino acids; contiguous of one or more of the polypeptides, which polypeptide is selected from the group consisting of:

a) a polypeptide comprising an amino acid sequence encoded by a nucleotide sequence selected from SEQ ID NO:3, 7, 11, 15, 19, 23 and 27; and b) a polypeptide comprising the amino acid sequence selected from SEQ ID NO:4, 8, 12, 16, 20, 24 and 28.

4. A polypeptide comprising a sequence having at least 98%, at least 98.5%, at least 99%, at least 99.2%, at least 99.4%, at least 99.6%, at least 99.8% or at least 99.9% sequence identity to at least one polypeptide selected from the group consisting of:

a) a polypeptide comprising an amino acid sequence encoded by a nucleotide sequence selected from SEQ ID NO: 1, 3, 5, 7, 9, 11, 13, 15, 17, 19, 21, 23, 25 and 27;

b) a polypeptide comprising an amino acid sequence encoded by a nucleotide sequence selected from residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25;

c) a polypeptide comprising an amino acid sequence selected from SEQ ID NO: 2, 4, 6, 8, 10, 12, 14, 16, 18, 20, 22, 24, 26 and 28; and d) a polypeptide comprising an amino acid sequence selected from residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26.

5. A polypeptide comprising a sequence having at least 95% sequence identity to at least one polypeptide selected from the group consisting of:

a) a polypeptide comprising an amino acid sequence encoded by a nucleotide sequence selected from SEQ ID NO: 1, 3, 5, 7, 9, 11, 13, 15, 17, 19, 21, 23, 25 and 27;

b) a polypeptide comprising an amino acid sequence encoded by a nucleotide sequence selected from residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25;

c) a polypeptide comprising an amino acid sequence selected from SEQ ID NO: 2, 4, 6, 8, 10, 12, 14, 16, 18, 20, 22, 24, 26 and 28; and d) a polypeptide comprising an amino acid sequence selected from residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26.

6. The polypeptide of embodiment 1, wherein the polypeptide is immunogenic.

7. A composition comprising one or more polypeptide of embodiment 1, or a fragment thereof.

8. A polypeptide which is specifically bound by a polyclonal antisera raised against at least one antigen, which antigen comprises at least one amino acid sequence of embodiment 1, or a fragment thereof.

9. An antibody specific for the polypeptide of embodiment 1.

10. An immunogenic composition comprising an immunologically effective amount of the polypeptide of embodiment 1.

11. A reassortant influenza virus comprising a polynucleotide encoding the polypeptide of embodiment 1.

12. The virus of embodiment 11, wherein the virus is a 6:2 reassortant virus comprising 6 internal genome segments from one or more donor virus and 2 genome segments encoding surface antigens of an influenza virus, wherein at least one of the 2 genome segments comprises a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

13. The virus of embodiment 12, wherein the donor virus is A/Ann Arbor/6/60, B/Ann Arbor/1/66, or A/Puerto Rico/8/34.

14. An immunogenic composition comprising an immunologically effective amount of the reassortant influenza virus of embodiment 13.

15. An isolated or recombinant polynucleotide, which polynucleotide is selected from the group consisting of:

a) a polynucleotide comprising a nucleotide sequence of one of SEQ ID NO: 1, 3, 5, 7, 9, 11, 13, 15, 17, 19, 21, 23, 25 and 27, or a complementary sequence thereof;

b) a polynucleotide comprising a nucleotide sequence of one of residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 c) a polynucleotide sequence encoding a polypeptide comprising an amino acid sequence of any one of SEQ ID NO: 2, 4, 6, 8, 10, 12, 14, 16, 18, 20, 22, 24, 26 and 28, or a complementary polynucleotide sequence thereof;

d) a polynucleotide sequence encoding a polypeptide comprising an amino acid sequence of any one of residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26; and e) a polynucleotide comprising a nucleotide sequence of one of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 in which one, two, three, four, five, six, seven, eight, nine, ten , eleven, twelve, thirteen, fourteen or fifteen nucleotide residues were substituted, inserted or deleted, or a complementary sequence thereof.

16. The polynucleotide of embodiment 15, wherein the polynucleotide is DNA.

17. The polynucleotide of embodiment 15, wherein the polynucleotide is RNA.

18. An isolated or recombinant polynucleotide encoding the polypeptide of embodiment 2.

19. An isolated or recombinant polynucleotide encoding the polypeptide of embodiment 3.

20. An isolated or recombinant polynucleotide comprising a nucleotide sequence encoding a hemagglutinin polypeptide or a neuraminidase polypeptide, and which nucleotide sequence has at least 98%, at least 98.5%, at least 99%, at least 99.2%, at least 99.4%, at least 99.6%, at least 99.8% or at least 99.9% sequence identity to at least one polynucleotide selected from the group consisting of:

a) a polynucleotide comprising a nucleotide sequence of one of SEQ ID NO: 1, 3, 5, 7, 9, 11, 13, 15, 17, 19, 21, 23, 25, 27, or a complementary sequence thereof;

b) a polynucleotide comprising a nucleotide sequence of one of residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 c) a polynucleotide sequence encoding a polypeptide comprising an amino acid sequence of any one of SEQ ID NO: 2, 4, 6, 8, 10, 12, 14, 16, 18, 20, 22, 24, 26 and 28, or a complementary polynucleotide sequence thereof; and d) a polynucleotide sequence encoding a polypeptide comprising an amino acid sequence of any one of residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26.

21. An isolated or recombinant polynucleotide comprising a nucleotide sequence which nucleotide sequence has at least 95% sequence identity to at least one polynucleotide selected from the group consisting of:
  a) a polynucleotide comprising a nucleotide sequence of one of SEQ ID NO: 1, 3, 5, 7, 9, 11, 13, 15, 17, 19, 21, 23, 25, 27, or a complementary sequence thereof;
  b) a polynucleotide comprising a nucleotide sequence of one of residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25
  c) a polynucleotide sequence encoding a polypeptide comprising an amino acid sequence of any one of SEQ ID NO: 2, 4, 6, 8, 10, 12, 14, 16, 18, 20, 22, 24, 26 and 28, or a complementary polynucleotide sequence thereof; and
  d) a polynucleotide sequence encoding a polypeptide comprising an amino acid sequence of any one of residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26.

22. An isolated or recombinant polynucleotide comprising a nucleotide sequence encoding a polypeptide, which polypeptide comprises a hemagglutinin polypeptide or a neuraminidase polypeptide produced by mutating or recombining one or more polynucleotide sequence of embodiment 15.

23. The polynucleotide of embodiment 15, wherein the polynucleotide encodes an immunogenic polypeptide.

24. A composition comprising one or more polynucleotide of embodiment 15, or a fragment thereof.

25. An immunogenic composition comprising an immunologically effective amount of the polynucleotide of embodiment 15.

26. A reassortant influenza virus comprising a polynucleotide of embodiment 15.

27. The virus of embodiment 26, wherein the virus is a 6:2 reassortant virus comprising 6 internal genome segments from one or more donor virus and 2 genome segments encoding surface antigens of an influenza virus, wherein at least one of the 2 genome segments comprises a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

28. The virus of embodiment 27, wherein the donor virus is A/Ann Arbor/6/60, B/Ann Arbor/1/66, or A/Puerto Rico/8/34.

29. An immunogenic composition comprising an immunologically effective amount of the recombinant influenza virus of embodiment 27.

30. A vector comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

31. The vector of embodiment 30, wherein the vector is a plasmid, a cosmid, a phage, a virus, or a fragment of a virus.

32. The vector of embodiment 30, wherein the vector is an expression vector.

33. The vector of embodiment 30, wherein the vector is a component of a multi-plasmid plasmid rescue method to produce one or more reassortant virus.

34. A cell transduced by the vector of embodiment 30.

35. A virus comprising a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

36. The virus of embodiment 35, wherein the virus is an influenza virus.

37. The virus of embodiment 36, wherein the polynucleotide comprises a nucleotide sequence encoding a hemagglutinin and/or neuraminidase or a fragment thereof.

38. The virus of embodiment 36, wherein the virus is a reassortant virus.

39. The virus of embodiment 36, wherein the virus is a 6:2 reassortant virus comprising 6 internal genome segments from one or more donor virus and 2 genome segments encoding surface antigens of an influenza virus, wherein at least one of the 2 genome segments comprises a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-

1787 of SEQ ID NO:21, residues 75-1115 of SEQ ID NO:25, and residues 1116-1787 of SEQ ID NO:25 or a fragment thereof.

40. The virus of embodiment 39, wherein the at least one of the 2 genome segments encodes a hemagglutinin or neuraminidase or a fragment thereof.

41. The virus of embodiment 36, wherein the virus is a 7:1 reassortant virus comprising 6 internal genome segments and a first genome segment encoding a first surface antigen of an influenza virus from one or more donor virus and a second genome segment encoding a second surface antigen of an influenza virus comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

42. The virus of embodiment 41, wherein the second genome segment encodes a hemagglutinin or neuraminidase, or a fragment thereof.

43. The virus of embodiment 39, wherein the donor virus is a temperature-sensitive virus, a cold-adapted virus, or an attenuated virus.

44. The virus of embodiment 39 or 41, wherein the donor virus comprises A/Ann Arbor/6/60, B/Ann Arbor/1/66, or A/Puerto Rico/8/34.

45. The virus of embodiment 39 or 41, wherein the virus is a live virus.

46. A cell comprising the virus of embodiment 45.

47. A method for producing reassortant influenza viruses in cell culture, the method comprising:
introducing a plurality of vectors comprising polynucleotides corresponding to an influenza virus genome into a population of host cells, which plurality of vectors comprises polynucleotides corresponding to at least 6 internal genome segments of a first influenza strain, and at least one genome segment of a second influenza strain, wherein the at least one genome segment of the second influenza strain comprises a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof, and wherein the population of host cells is capable of supporting replication of influenza virus;
culturing the population of host cells; and
recovering a plurality of influenza viruses.

48. The method of embodiment 47, wherein the first influenza strain is an attenuated influenza virus strain, a cold-adapted influenza virus strain, or a temperature-sensitive influenza virus strain.

49. The method of embodiment 47, wherein the influenza viruses are suitable for administration in an intranasal vaccine formulation.

50. The method of embodiment 47, wherein the influenza virus genome is an influenza B virus genome.

51. The method of embodiment 47, wherein the influenza virus genome is an influenza A virus genome.

52. The method of embodiment 47, wherein the first influenza strain is A/Ann Arbor/6/60, B/Ann Arbor/1/66, or A/Puerto Rico/8/34.

53. The method of embodiment 47, wherein the plurality of vectors is a plurality of plasmid vectors.

54. The method of embodiment 47, wherein the population of host cells comprises one or more of: Vero cells, PerC6 cells, MDCK cells, 293T cells, and COS cells.

55. The method of embodiment 47, comprising recovering reassortant influenza viruses.

56. The method of embodiment 47, wherein the method does not comprise use of a helper virus.

57. The method of embodiment 47, wherein the plurality of vectors is eight vectors.

58. The method of embodiment 47, wherein the at least one genome segment encodes an immunogenic influenza surface antigen of the second influenza strain.

59. An immunogenic composition comprising a polypeptide comprising an amino acid sequence selected from SEQ ID NO:2, 4, 6, 8, 10, 12, 14, 16, 18, 20, 22, 24, 26, 28, residues 17-345 of SEQ ID NO:2, residues 346-566 of SEQ ID NO:2, residues 18-343 of SEQ ID NO:6, residues 344-565 of SEQ ID NO:6, residues 18-361 of SEQ ID NO:10, residues 16-361 of SEQ ID NO:10 and residues 362-584 of SEQ ID NO:10, residues 17-345 of SEQ ID NO:14, residues 346-566 of SEQ ID NO:14, residues 18-343 of SEQ ID NO:18, residues 344-565 of SEQ ID NO:18, residues 16-362 of SEQ ID NO:22, residues 363-585 of SEQ ID NO:22, residues 16-362 of SEQ ID NO:26 and residues 363-585 of SEQ ID NO:26.

60. An immunogenic composition comprising a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25.

61. The composition of embodiment 59 or 60, further comprising an excipient.

62. The composition of embodiment 61, wherein the excipient is a pharmaceutically acceptable excipient.

63. An immunogenic composition comprising a reassortant virus comprising a polynucleotide having a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25.

64. The composition of embodiment 63, wherein the reassortant virus is a 6:2 reassortant virus, which virus comprises 6 internal genome segments form one or more donor virus and 2 genome segments encoding surface antigens of an influenza virus, wherein at least one of the 2 genome segments comprises a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25.

65. The composition of embodiment 64, wherein the influenza donor virus strain is a cold adapted, attenuated, and/or temperature sensitive influenza virus strain.

66. The composition of embodiment 65, wherein the influenza donor virus strain is A/Ann Arbor/6/60, B/Ann Arbor/1/66, or A/Puerto Rico/8/34.

67. A live attenuated influenza vaccine comprising the immunogenic composition of embodiment 63.

68. The composition of embodiment 63, further comprising one or more pharmaceutically acceptable excipient.

69. A method of producing an influenza virus vaccine, the method comprising:
introducing a plurality of vectors comprising polynucleotides corresponding to an influenza virus genome into a population of host cells, which plurality of vectors comprises polynucleotides corresponding to at least 6 internal genome segments of a first influenza strain, and at least one genome segment of a second influenza strain, wherein the at least one genome segment of the second influenza strain comprises a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof, and wherein the population of host cells is capable of supporting replication of influenza virus;
culturing the population of host cells;
recovering a plurality of influenza viruses; and
providing one or more pharmaceutically acceptable excipient.

70. The method of embodiment 69, wherein the first influenza strain is an attenuated influenza virus, a cold-adapted influenza virus, or a temperature-sensitive influenza virus.

71. The method of embodiment 69, wherein the viruses produced are suitable for administration in an intranasal vaccine formulation.

72. The method of embodiment 69, wherein the influenza virus genome is an influenza B virus genome or an influenza A virus genome.

73. The method of embodiment 69, wherein the at least one genome segment encodes an immunogenic influenza surface antigen of the second influenza strain.

74. A method of prophylactic or therapeutic treatment of a viral infection in a subject, the method comprising: administering to the subject, a reassortant virus comprising a polynucleotide comprising a nucleotide sequence selected from SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof, in an amount effective to produce an immunogenic response against the viral infection.

75. The method of embodiment 74, wherein the subject is a mammal.

76. The method of embodiment 74, wherein the mammal is a human.

77. The method of embodiment 74, wherein the viral infection comprises a viral influenza infection.

78. The method of embodiment 74, wherein the virus is administered in vivo to the subject or in vitro or ex vivo to one or more cells of the subject.

79. The method of embodiment 74, wherein a composition comprising the reassortant virus and a pharmaceutically acceptable excipient is administered to the subject in an amount sufficient to prophylactically or therapeutically treat the viral infection.

80. A DNA molecule comprising a transcription control element that binds a DNA-directed RNA polymerase and is operatively linked to a DNA sequence that encodes an RNA molecule, wherein the RNA molecule comprises a binding site specific for an RNA-directed RNA polymerase of an influenza virus, operatively linked to an RNA sequence comprising the reverse complement of an mRNA coding sequence of an influenza virus, wherein the DNA sequence comprises a nucleic acid corresponding to one or more of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

81. A DNA molecule comprising a nucleotide sequence that upon transcription yields an RNA template that contains an RNA sequence comprising the reverse complement of an mRNA coding sequence of an influenza virus, and vRNA terminal sequences, wherein the nucleotide sequence comprises a nucleic acid corresponding to one or more of SEQ ID NO: 1, 3, 5, 7, 9, 11, 13, 15, 17, 19, 21, 23, 25, 27, residues 74-1060 of SEQ ID NO:1, residues 1061-1723 of SEQ ID NO:1, residues 81-1058 of SEQ ID NO:5, residues 1059-1724 of SEQ ID NO:5, residues 85-1116 of SEQ ID NO:9, residues 79-1116 of SEQ ID NO:9, residues 1117-1785 of SEQ ID NO:9, residues 78-1064 of SEQ ID NO:13, residues 1065-1727 of SEQ ID NO:13, residues 78-1055 of SEQ ID NO:17, residues 1056-1721 of SEQ ID NO:17, residues 78-1118 of SEQ ID NO:21, residues 1119-1787 of SEQ ID NO:21, residues 75-1115 of SEQ ID NO:25, and residues 1116-1787 of SEQ ID NO:25 or a fragment thereof.

82. The DNA molecule of embodiment 81, wherein the RNA template is replicable.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In particular, the following patent applications are incorporated by reference in their entirety for all purposes: U.S. Provisional Application Nos. 61/079,894 filed Jul. 11, 2008, 61/110,702 filed Nov. 3, 2008 and 61/178,592 filed May 15, 2009.

What is claimed is:

1. An isolated reassortant influenza virus comprising a genome segment encoding a polypeptide comprising the amino acid sequence of SEQ ID NO:18.

2. The virus of claim 1, wherein the polypeptide is encoded by the nucleotide sequence of SEQ ID NO:17.

3. The virus of claim 1, wherein the virus is a 6:2 reassortant virus comprising 6 internal genome segments from one or more donor viruses and 2 genome segments encoding surface antigens of an influenza virus.

4. The virus of claim 2, wherein the virus is a 6:2 reassortant virus comprising 6 internal genome segments from one or more donor viruses and 2 genome segments encoding surface antigens of an influenza virus.

5. The virus of claim 3, wherein the donor virus is A/Ann Arbor/6/60, B/Ann Arbor/1/66, or A/Puerto Rico/8/34.

6. The virus of claim 4, wherein the donor virus is A/Ann Arbor/6/60, B/Ann Arbor/1/66, or A/Puerto Rico/8/34.

7. The virus of claim 3, wherein the donor viruses are selected according to one or more phenotypic attributes selected from the group consisting of: attenuated, cold adapted and temperature sensitive.

8. The virus of claim 4, wherein the donor viruses are selected according to one or more phenotypic attributes selected from the group consisting of: attenuated, cold adapted and temperature sensitive.

9. An immunogenic composition comprising an immunologically effective amount of the reassortant influenza virus of claim 1.

10. A live attenuated influenza vaccine comprising the immunogenic composition of claim 9.

11. A method for producing reassortant influenza viruses in cell culture, the method comprising:

i) introducing a plurality of vectors comprising polynucleotides corresponding to an influenza virus genome into a population of host cells capable of supporting replication of influenza virus, which plurality of vectors comprises polynucleotides corresponding to at least 6 internal genome segments of a first influenza strain, and at least one genome segment of a second influenza strain, wherein the at least one genome segment of the second influenza strain comprises a nucleotide sequence encoding a polypeptide comprising the amino acid sequence of SEQ ID NO:18;

ii) culturing the population of host cells; and iii) recovering a plurality of reassortant influenza viruses comprising a polypeptide comprising the amino acid sequence of SEQ ID NO:18.

12. The method of claim 11, wherein the at least one genome segment of the second influenza strain comprises a nucleotide sequence of SEQ ID NO:17.

13. The method of claim 11, wherein the first influenza strain is an attenuated influenza virus strain, a cold-adapted influenza virus strain, a temperature-sensitive influenza virus strain or combinations thereof.

14. The method of claim 12, wherein the first influenza strain is an attenuated influenza virus strain, a cold-adapted influenza virus strain, a temperature-sensitive influenza virus strain or combinations thereof.

15. The method of claim 11, wherein the plurality of vectors is eight vectors.

16. A method of prophylactic or therapeutic treatment of an influenza viral infection in a subject, the method comprising: administering to the subject, a reassortant influenza virus comprising:

a) a polynucleotide comprising a nucleotide sequence of SEQ ID NO:17; or b) a polynucleotide sequence encoding a polypeptide comprising an amino acid sequence of SEQ ID NO:18;

in an amount effective to produce an immunogenic response against the influenza viral infection.

17. An isolated or recombinant polypeptide, which polypeptide is selected from the group consisting of:
   a) a polypeptide comprising an amino acid sequence encoded by a nucleotide sequence of SEQ ID NO:17; and
   b) a polypeptide comprising an amino acid sequence of SEQ ID NO:18.

18. An isolated or recombinant polynucleotide, which polynucleotide is selected from the group consisting of:
   a) a polynucleotide comprising a nucleotide sequence of SEQ ID NO:17, or a complementary sequence thereof; and
   b) a polynucleotide encoding a polypeptide comprising an amino acid sequence of SEQ ID NO:18, or a complementary polynucleotide sequence thereof.

19. An immunogenic composition comprising an immunologically effective amount of the polynucleotide of claim 18.

20. A vector comprising a polynucleotide of claim 18.

21. A cell comprising a vector of claim 20.

22. An immunogenic composition comprising an immunologically effective amount of the polypeptide of claim 17.

* * * * *

UNITED STATES PATENT AND TRADEMARK OFFICE
CERTIFICATE OF CORRECTION

PATENT NO. : 8,591,914 B2  Page 1 of 1
APPLICATION NO. : 13/003559
DATED : November 26, 2013
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 110 days.

Signed and Sealed this
Twenty-second Day of September, 2015

Michelle K. Lee
*Director of the United States Patent and Trademark Office*